(12) United States Patent
Hohmann et al.

(10) Patent No.: US 6,322,995 B1
(45) Date of Patent: *Nov. 27, 2001

(54) RIBOFLAVIN PRODUCTION

(75) Inventors: Hans-Peter Hohmann, Freiburg (DE);
Markus Hümbelin, Zeihen (CH);
Adolphus van Loon, Rheinfelden
(CH); Walter Schurter, Basel (CH)

(73) Assignee: F. Hoffmann-La Roche AG, Basel
(CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/899,241

(22) Filed: Jul. 23, 1997

(30) Foreign Application Priority Data

Jul. 24, 1996 (EP) .................................................. 96111905

(51) Int. Cl.[7] ................. C12P 25/00; C12N 1/21

(52) U.S. Cl. ................. 435/66; 435/252.3; 435/252.31; 435/252.32; 435/252.5; 435/253.4; 435/252.33

(58) Field of Search ............................ 435/252.3, 252.31, 435/66, 252.32, 252.5, 253.4, 252.33

(56) References Cited

U.S. PATENT DOCUMENTS 3,900,368   8/1975   Enei et al. .

FOREIGN PATENT DOCUMENTS

| 4 405 370 A | 1/1991 | (EP) . |
| 405 370 A1 | 1/1991 | (EP) . |
| 0 604 060 A | 6/1994 | (EP) . |

OTHER PUBLICATIONS

Bailey, James E., *Science*, vol. 252, pp. 1668–1675, Jun. 21, 1991.*
Derwent Abstract No. AN 85–020681/04.
Chikindas, et al., *Mol. Genet. Mik. Virusol.*, No. 2:20 (1987).
Chikindas, et al., *Mol. Genet. Mik. Virusol.*, No. 4:22 (1987).
Ishii and Shiio, *Agric. Biol. Chem.*, 36(9):1511–1522 (1972).
Ludwig, et al., *J. Biol. Chem.*, 262:1016 (1987).
Matsui, et al., *Agric. Biol. Chem.*, 43(8): 1739–1744 (1979).
Matsui, et al., *Agric. Biol. Chem.*, 46(8):2003–2008 (1982).
Morozov, et al., *Mol. Genet. Mik. Virusol.*, No. 7:42 (1984).
Morozov, et al., *Mol. Genet. Mik. Virusol.*, No. 11:11 (1984).
Morozov, et al. *Mol. Genet. Mik. Virusol.*, No. 12:14 (1985).
Richter, et al., "Biosynthesis of Riboflavin: Cloning, Sequencing, Mapping, and Expression of the Gene Coding for GTP Cyclohydrolase II in *Eschericia coli*." *Journal of Bacteriology*, vol. 175, No. 13: pp. 4045–4051 (1993).

* cited by examiner

Primary Examiner—David Guzo
(74) Attorney, Agent, or Firm—Bryan Cave, LLP

(57) ABSTRACT

The present invention provides a recombinant bacterium for the over-production of riboflavin. The recombinant bacterium has has been transformed by three or four vectors, two of which each comprise either a DNA sequence coding for the riboflavin synthesizing enzymatic activities of *Bacillus subtilis* or a DNA sequence which is substantially homologous and one or more transcription elements and a third and/or fourth vector comprising either a DNA sequence coding for the ribA gene product of *Bacillus subtilis* or a DNA sequence which is substantially homologous and optionally a transcription element whereby one or a plurality of copies of each of these vectors has/have been integrated at three or four different sites within the bacterium's chromosome.

24 Claims, 40 Drawing Sheets

FIGURE 3A

Page 2

```
   B N          N     XH   H                        S H
   S L          N     HN   N                        P B
   P A          E     NF   L                        O O
   N 3          1     11   1                        1 2
                                         RBS    ORF 6
ATTCATGAAAAAAAGGAATAACTCATATGAATGAATAGATTCATATTGGCTGGAGGTTTAGAAATGGGAAGAATAAAAACCAAGATTACCATTCTGTTAG
----.----+----.----+----.----+----.----+----.----+----.----+----.----+----.----+----.----+----.----→ 400
TAAGTACTTTTTTTCCTTATTGAGTATACTTACTTATCTAAGTATAACCGACCTCCAAATCTTTACCCTTCTTATTTTTGGTTCTAATGGTAAGACAATC i h e k k e . l i . m'n r f i l a g g l e m g r i k t k i t i l l v
       f m k k r n n s y e . i d s y w l e v . k w e e . k p r l p f c .
         s . k k g i t h m n e . i h i g w r f r n g k n k n q d y h s v s
   ----.----+----.----+----.----+----.----+----.----+----.----+----.----+----.----+----.----+----.----
   i . s f f s y s m h i f l n m n a p p k s i p l i f v l i v m r n
     n m f f l f l e y s h i s e y q s s t . f h s s y f g l n g n q .
       . e h f f p i v . i f s y i . i p q l n l f p f f l f w s . w e t l

R               A                F         BSB M   KEF N
                              S               L                O         SES N   SAO N
                              A               U                K         ACA L   PRK L
                              1               1                1         J1J 1   211 1
                                                                            /     /
TGCTTTTGCTTTTACTTGCAGGCGGTTATATGTACATAAATGATATTGAGCTGAAGGATGTTCCGACAGCAATTGGACAAACCTTGTCCTCGGAAGAAGA
----.----+----.----+----.----+----.----+----.----+----.----+----.----+----.----+----.----+----.----→ 500
ACGAAAACGAAAATGAACGTCCGCCAATATACATGTATTTACTATAACTCGACTTCCTACAAGGCTGTCGTTAACCTGTTTGGAACAGGAGCCTTCTTCT l l l l l a g g y m y i n d i e l k d v p t a i g q t l s s e e e
         c f c f y l q a v i c t . m i l s . r m f r q q l d k p c p r k k r
           a f a f t c r r l y v h k . y . a e g c s d s n w t n l v l g r r
   ----.----+----.----+----.----+----.----+----.----+----.----+----.----+----.----+----.----+----.----
   t s k s k s a p p . i y m f s i s s f s t g v s i p c v k d e s s s
     h k q k . k c a t i h v y l i n l q l i n r e e n s l g q g r f f
       a k a k v q l r n y t c l h y q a s p h e s l l q v f r t r p l l

M M  E AS      M           D           N              M
       B B  C PC      A           D           L              B
       O O  R YR      E           E           A              O
       2 2  2 11      3           1           3              2
          /
GGAATACACCATCCAGGAATATAAAGTGACGAAAATTGACGGCTCAGAGTATCATGGAGTAGCAGAAAACGGAACGAAAATCATCTTCAACGGAAAAAAA
----.----+----.----+----.----+----.----+----.----+----.----+----.----+----.----+----.----+----.----→ 600
CCTTATGTGGTAGGTCCTTATATTTCACTGCTTTTAAACTGCCGAGTCTCATAGTACCTCATCGTCTTTTGCCTTGCTTTTAGTAGAAGTTGCCTTTTTT e y t i q e y k v t k i d g s e y h g v a e n g t k i i f n g k k
         n t p s r n i k . r k l t a q s i m e . q k t e r k s s s t e k n
           g i h h p g i . s d e n . r l r v s w s s r k r n e n h l q r k k i
   ----.----+----.----+----.----+----.----+----.----+----.----+----.----+----.----+----.----+----.----
   s y v m w s y l t v f i s p e s y . p t a s f p v f i m k l p f f
     l f v g d l f i f h r f n v a . l i m s y c f v s r f d d e v s f f
       p i c w g p i y l s s f q r s l t d h l l l f r f s f . r . r f f
```

FIGURE 3B

```
  H              H      H H              BM DT      H
  S              A      S P              IB PA      S
  E              E      E H              NO NQ      E    ORF 6
  1              3      1 1              11 11      1   TRANSLATION
                                                        STOP
```

TTAAATCAGGATTTATCTGATATAAAAGAAGGTGACAAGATTAAGGCTTACTTCAGCAAATCAAAGCGGATCGACGGTTAATCAAGGTTGCAAAAGTGAA
----.----+----.----+----.----+----.----+----.----+----.----+----.----+----.----+----.----+----.----+ 700
AATTTAGTCCTAAATAGACTATATTTTCTTCCACTGTTCTAATTCCGAATGAAGTCGTTTAGTTTCGCCTAGCTGCCAATTAGTTCCAACGTTTTCACTT

```
l n q d l s d i k e g. d k i k a y f s k s k r i d g . s r l q k . m
. i r i y l i . k k v t r l r l t s a n q s g s t v n q g c k s e
k s g f i . y k r r . q d . g l l q q i k a d r r l i k v a k v n
. . . . . . . . . . . . . . . . . . . . . . . . . . . . . . . . .
n f . s k d s i f s p s l i l a . k l l d f r i s p . d l n c f h
. i l i . r i y f f t v l n l s v e a f . l p d v t l . p q l l s
i l d p n i q y l l l h c s . p k s . c i l a s r r n i l t a f t f
```

```
  H H            BM DT              H                      R   HD   BM D
  S P            IB PA              P                      S   SR   IB P
  E H            NO NQ  RHO-INDEPENDENT                    A   EA   NO N
  1 1            11 11  TRANSCRIPTION     1                1   11   11 1    P1 PROMOTER
                        TERMINATOR
```
TGATTAAAAAACATCACCTTTCGGATCGAAGGGTGATGTTTTGTTTTTCTCAAATTGTAAGTTTATTTCATTGCGTACTTTAAAAAGGATCGCTATAATA
----.----+----.----+----.----+----.----+----.----+----.----+----.----+----.----+----.----+----.----+ 800
ACTAATTTTTTGTAGTGGAAAGCCTAGCTTCCCACTACAAAACAAAAAGAGTTTAACATTCAAATAAAGTAACGCATGAAATTTTTCCTAGCGATATTAT

```
i k k h h l s d r r v m f c f s q i v s l f h c v l . k g s l . .
. l k n i t f r i e g . c f v f l k l . v y f i a y f k k d r y n n
d . k t s p f g s k g d v l f f s n c k f i s l r t l k r i a i i
. . . . . . . . . . . . . . . . . . . . . . . . . . . . . . . . .
i i l f c . r e s r l t i n q k e . i t l k n . q t s . f p d s y y
h n f f m v k r i s p h h k t k r l n y t . k m a y k l f s r . l
s . f v d g k p d f p s t k n k e f q l n i e n r v k f l i a i i
```

```
                E                                CH                      BNM
                C                                FP                      ASA
                O                                RA                      HPE
                D                                22                      223
                                                                         //
```
ACCAATAAGGACAAATGAATAAAGATTGTATCCTTCGGGGCAGGGTGGAAATCCCGACCGGCGGTAGTAAAGCACATTTGCTTTAGAGCCCGTGACCCGT
----.----+----.----+----.----+----.----+----.----+----.----+----.----+----.----+----.----+----.----+ 900
TGGTTATTCCTGTTTACTTATTTCTAACATAGGAAGCCCCGTCCCACCTTTAGGGCTGGCCGCCATCATTTCGTGTAAACGAAATCTCGGGCACTGGGCA

Page 14

```
      A     H        T           SHH   B   P    H D             F   H
      L     N        H           TAA   G   L    N D             H   N
      U     F        A           UEE   L   E    F E             U   L
      1     3        1           113   1   1    1 1             H   1
                                  //
AGCTTTTGACGAATAATCCGCGAAAAATCGCAGGCCTTGAAGGCTACGGACTCAGTATTTCAGAAAGAGTGCCGCTTCAAATGGAGGCGAAAGAACACAA
----.----+----.----+----.----+----.----+----.----+----.----+----.----+----.----+----.----+----.----+  4000
TCGAAAACTGCTTATTAGGCGCTTTTTAGCGTCCGGAACTTCCGATGCCTGAGTCATAAAGTCTTTCTCACGGCGAAGTTTACCTCCGCTTTCTTGTGTT s f . r i i r e k s q a l k a t d s v f q k a c f k w r r k n t i
    a f d e . s a k n r r p . r l r t q y f r k s a a s n g g e r t q
      l l r n n p r k i a g l e g y g i s i s e r v p l q m e a k e h n
----.----+----.----+----.----+----.----+----.----+----.----+----.----+----.----+----.----+----.----+
    l k q r i i r s f d c a k f a v s e t n . f s h r k l h l r f f v
      a k s s y d e f f r l g q l s r v . y k l f l a a e f p p s l v c
        f s k v f l g r f i s p r s p . p s l i e s l t g s . i s a f s c l

S                AH                                        H    HH      N F
      S                LA                                        A    AN      D O
      P                UE                                        N    HF      E K
      1                11         ORF 3 TRANSLATION              I    11      1 1      5-RIBOFLAVIN
                                       STOP                      RBS                    SYNTHASE GENE
TAAAAAATATTTGCAAACCAAAATGAACAAGCTAGGTCATTTACTTCATTTCTAATCACAAATATCACAAAAAAGGATGGGAATCATATGAATATCATAC
----.----+----.----+----.----+----.----+----.----+----.----+----.----+----.----+----.----+----.----+  4100
ATTTTTTATAAACGTTTGGTTTTACTTGTTCGATCCAGTAAATGAAGTAAAGATTAGTGTTTATAGTGTTTTTTCCTACCCTTAGTATACTTATAGTATG k n i c k p k . t s . v i y f i s n h k y h k k g w e s y e y h t
      . k l f a n q n e q a r s f t s f l i t n i t k k d g n h m n i i q
        k k y l q t k m n k l g h l l h f . s q i s q k r m g i i . i s y
----.----+----.----+----.----+----.----+----.----+----.----+----.----+----.----+----.----+----.----+
    i f f i q l g f h v l . t m . k m e l . l y . l f p h s d y s y . v
      y f l n a f w f s c a l d n v e n r i v f i v f f s p f . i f i m
        l f y k c v l i f l s p . k s . k . d c i d c f l i p i m h i d y

R E    N        H                   H    H S          AF   EDE  S B           H HF
          S C    S        N                   S    B B          LN   SDC  F B           I HN
          A P    E        F                   E    D V          UU   PEI  A V           N AU
          1 1    1        1                   1    2 1          1H   115  N 1           P 1H
                                                                                /
AAGGAAATTTAGTTGGTACAGGTCTTAAAATCGGAATCGTAGTAGGAAGATTTAATGATTTTATTACGAGCAAGCTGCTGAGCCGGAGCAGAAGATGCCCT
----.----+----.----+----.----+----.----+----.----+----.----+----.----+----.----+----.----+----.----+  4200
TTCCTTTAAATCAACCATGTCCAGAATTTTAGCCTTAGCATCATCCTTCTAAATTACTAAAATAATGCTCGTTCGACGACTCGGCCTCGTCTTCTACGGGA r k f s w y r s . n r n r s r k i . . f y y e q a a e r s r r c a
      g n l v g t g l k i g i v v g r f n d f i t s k l l s g a e d a l
        k e i . l v q v l k s a s . . e d l m i l l r a s c . a e q k m r c
----.----+----.----+----.----+----.----+----.----+----.----+----.----+----.----+----.----+----.----+
    l f n l q y l d . f r f r l l f i . h n . . s c a a s r l l l h a
      c p f k t p v p r l i p i t t p l n l s k i v l l s s l p a s s a s
        l s l . n t c t k f d s d y y s s k i i k n r a l q q a s c f i r
```

Page 16

```
        S           HD                                                  HD                H
        S           SR                                                  SR                P
        T           EA              B-RIBOFLAVIN SYNTHASE               EA                K
        X           11              TRANSLATION STOP                    11                1
                                            P3 PROMOTER
TTGTGCTGTTTCTGCCATTGAAATGGCAAATTTAAACCGCTCATTTGAATAATTTGCTGAAAACAGTTTAAAAATATGGCGAAAATGATATAATGTGAGA
----.----+----.----+----.----+----.----+----.----+----.----+----.----+----.----+----.----+----.----    4600
AACACGACAAAGACGGTAACTTTACCGTTTAAATTTGGCGAGTAAACTTATTAAACGACTTTTGTCAAATTTTTATACCGCTTTTACTATATTACACTCT l   c  c  f  c  h  .  n  g  k  *  k  p  l  i  .  i  i  c  .  k  q  f  k  n  m  a  k  m  i  .  c  e  k
     c  a  v  s  a  i  e  m  a  n  l  n  r  s  f  e  .  f  a  e  n  s  l  k  l  w  r  k  .  y  n  v  r
      v  l  f  l  p  l  k  w  q  i  .  t  a  h  l  n  n  l  l  k  t  v  .  k  y  g  e  n  d  i  m  .  e
    ----.----+----.----+----.----+----.----+----.----+----.----+----.----+----.----+----.----+----.----+
    n  h  q  k  q  w  q  f  p  l  n  l  g  s  m  q  i  i  q  q  f  c  n  l  f  l  a  f  l  l  y  h  s
     q  a  t  e  a  m  s  i  a  f  k  f  r  e  n  s  y  n  a  s  f  l  k  f  i  h  r  f  h  y  l  c  l
      l  t  s  n  r  g  n  f  h  c  l  .  v  a  .  k  f  l  k  s  f  v  t  .  f  y  p  s  f  s  i  i  h  s

BM  D           H           H                   H                       H           H
        IB  P           N           S                   N                       S           N
        NO  N           F           E                   L                       E           F
        11  1           3           1                   1                       1           3
                                                          RBS      ORF 2
AAACGGATCACCTATTCGTATCCGTTAATAGCAGACTGGACATTTTGGATATAGAGGGGTTTTTATGTTAATTCGTTATAAAAAATCGTTTGAAAAGATT
----.----+----.----+----.----+----.----+----.----+----.----+----.----+----.----+----.----+----.----    4700
TTTGCCTAGTGGATAAGCATAGGCAATTATCGTCTGACCTGTAAAACCTATATCTCCCCAAAAATACAATTAAGCAATATTTTTTAGCAAACTTTTCTAA t  d  h  l  f  v  s  v  n  s  r  l  d  i  l  d  i  e  g  f  l  c  .  f  v  i  k  n  r  l  k  r  l
     k  r  i  t  y  s  y  p  l  i  a  d  w  t  f  w  i  .  r  g  f  y  v  n  s  l  .  k  i  v  .  k  d  c
      n  g  s  p  i  r  i  r  .  .  q  t  g  h  f  g  y  r  g  v  f  m  l  i  r  y  k  k  s  f  e  k  i
    ----.----+----.----+----.----+----.----+----.----+----.----+----.----+----.----+----.----+----.----+
    f  v  s  .  r  n  t  d  t  l  l  l  s  s  m  k  s  i  s  p  n  k  h  .  n  t  i  f  f  r  k  f  l  n
     f  r  i  v  .  e  y  g  n  i  a  s  q  v  n  q  i  y  l  p  k  .  t  l  e  n  y  f  i  t  q  f  s
      f  p  d  g  i  r  i  r  .  y  c  v  p  c  k  p  y  l  p  t  k  l  n  i  r  .  l  f  d  n  s  f  i

X                   EAM     F  A   E       B       M                   E       A
                        N                   CFS     N  L   C       B       S                   C       L
                        F                   PLE     U  U   1       V       E                   P       U
                        3                   121     H  1   5       1       1                   1       1
                                            //
GCGATGGGGCTTCTTTCGTTTATGCCGAATGAAAAAGACCTTAAGCAGCTTCAGCAGACAATTAAGGACTACGAAACGGATACAGACCGCCAGCTCTTTC
----.----+----.----+----.----+----.----+----.----+----.----+----.----+----.----+----.----+----.----+    4800
CGCTACCCCGAAGAAAGCAAATACGGCTTACTTTTTCTGGAATTCGTCGAAGTCGTCTGTTAATTCCTGATGCTTTGCCTATGTCTGGCGGTCGAGAAAG r  w  g  f  f  r  l  c  r  m  k  k  t  l  s  s  f  s  r  q  l  r  t  t  k  r  i  q  t  a  s  s  f
     d  g  a  s  f  v  y  s  e  .  k  r  p  .  a  a  s  a  d  n  .  g  l  r  n  g  y  r  p  p  a  l  s
      a  m  g  l  l  s  f  m  p  n  e  k  d  l  k  q  l  q  q  t  i  k  d  y  e  t  d  t  d  r  q  l  f  l
    ----.----+----.----+----.----+----.----+----.----+----.----+----.----+----.----+----.----+----.----+
    r  h  p  k  k  r  k  h  r  i  f  f  v  k  l  l  k  l  l  c  n  l  v  v  f  r  i  c  v  a  l  e  k
     q  s  p  a  e  k  t  .  a  a  h  f  l  g  .  a  a  e  a  s  l  .  p  s  r  f  p  y  l  g  g  a  r  e
      a  i  p  s  r  e  n  i  g  f  s  f  s  r  l  c  s  .  c  v  i  l  s  .  s  v  s  v  s  r  w  s  k
```

| UPSTREAM FROM ribP1 | WITHIN 5' LEADER mRNA | AT 3' END OF RIB OPERON |
|---|---|---|
|     A<br>G   T<br> G•C<br> C•G<br> T•A<br> T•A<br> T•G<br> C•G<br> C•G<br> A•T<br> C•G<br> T•A<br> A•T<br> C•G<br> A•T<br> A•T<br> A•T<br>AA•TG($T_5$) |    T<br> T  A<br>T    T<br> T•A<br> T•A<br> T•A<br> A•T<br> A•T<br> G•C<br> C•G<br> C•G<br> C•G<br> C•G<br> G•C<br>AAA•T($T_5$) |   G  A<br>T    T<br> G•C<br> T•A<br> C•G<br> G•T<br> G•C<br> A•T<br> G•C<br> A•T<br> C•G<br> G•C<br> A•T<br>TA•T($T_6$) |
| #708   #742 | #1034   #1062 | #5037   #5064 |
| ΔG = -20 kcal/mol | ΔG = -26 kcal/mol | ΔG = -16.5 kcal/mol |

FIG. 9

RB-5  AATTCATGCATGGATCCGACGGTAAATAAC
AAAAGAGGGGAGGGAAACAAATGGAAGAGT
ATTATATGAAGCTGGCCTTA

RB-6  GATCTAAGGCCAGCTTCATATAATACTCTT
CCATTTGTTTCCCTCCCCTCTTTTGTTATT
TACCGTCGGATCCATGCATG

P2-A  TCGACGGATCCTTTTAGAGAGGAAGATTTG
CATGTTTCATCCGATAGAAGAAGCACTGGA
CGCTTT

P2-B  AAAGCGTCCAGTGCTTCTTCTATCGGATGA
AACATGCAAATCTTCCTCTCTAAAAGGATC
CG

P2-CII  CGATTTTTGCATAAAGCCAATGAAAATAAG
ACCCAACAAACCATTACAAAAGCCTTCTTA
AGCGAAAAGCGGTTTTAG

P2-DII  AATTCTAAAAGCCGTTTTCGCTTAAGAAGG
CTTTTGTAATGGTTTGTTGGGTCTTATTTT
CATTGGCTTTATGCAAAAAT

FIG. 18

RIBOFLAVIN PRODUCTION

BACKGROUND OF THE INVENTION

Riboflavin (vitamin $B_2$) is synthesized by all plants and many microorganisms but is not produced by higher animals. Because it is a precursor to coenzymes such as flavin adenine dinucleotide and flavin mononucleotide, that are required in the enzymatic oxidation of carbohydrates, riboflavin is essential to basic metabolism. In higher animals, insufficient riboflavin can cause loss of hair, inflammation of the skin, vision deterioration, and growth failure.

Riboflavin can be commercially produced either by a complete chemical synthesis, starting with ribose, or by fermentation with the fungi Eremothecium ashbyii or Ashbya gossypii (The Merck Index, Windholz et al., eds., Merck & Co., p. 1183, 1983). Mutants of Bacillus subtilis, selected by exposure to the purine analogs azaguanine and azaxanthine, have been reported to produce riboflavin in recoverable amounts (U.S. Pat. No. 3,900,368, Enei et al., 1975). In general, exposure to purine or riboflavin analogs selects for deregulated mutants that exhibit increased riboflavin biosynthesis, because the mutations allow the microorganism to "compete out" the analog by increased production (Matsui et al., Agric. Biol. Chem. 46:2003, 1982). A purine-requiring mutant of Saccharomyces cerevisiae that produces riboflavin has also been reported (U.S. Pat. No. 4,794,081, Kawai et al., 1988). Rabinovich et al. (Genetika 14:1696 (1978)) report that the riboflavin operon (rib operon) of B. subtilis is contained within a 7 megadalton (Md) EcoRI fragment (later referred to as a 6.3 Md fragment in Chikindas et al., Mol. Genet. Mik. Virusol. no. 2:20 (1987)). It is reported that amplification of the rib operon may have been achieved in E. coli by cloning the operon into a plasmid that conferred resistance to ampicillin and exposing bacteria containing that plasmid to increasing amounts of the antibiotic. The only evidence for rib amplification is a coincident increase in the presence of a green-fluorescing substance in the medium; the authors present a number of alternative possibilities besides an actual amplification of the operon to explain the phenomenon observed.

French Patent Application No. 2,546,907, by Stepanov et al. (published Dec. 7, 1984), discloses a method for producing riboflavin that utilizes a mutant strain of B. subtilis which has been exposed to azaguanine and roseoflavin and that is transformed with a plasmid containing a copy of the rib operon.

Morozov et al. (Mol. Genet. Mik. Virusol. no. 7:42 (1984)) describe the mapping of the B. subtilis rib operon by assaying the ability of cloned B. subtilis rib fragments to complement E. coli riboflavin auxotrophs or to marker-rescue B. subtilis riboflavin auxotrophs. Based on the known functions of the E. coli rib genes, the following model was proposed for the B. subtilis operon: ribG (encoding a deaminase)—ribO (the control element)—ribB (a synthetase)—ribF—ribA (a GTP-cyclohydrolase)—ribT/D (a reductase and an isomerase, respectively)—ribH (a synthetase).

Morozov et al. (Mol. Genet. Mik. Virusol. no. 11:11 (1984)) describe the use of plasmids containing the B. subtilis rib operon with either wild-type (ribO$^+$) or constitutive (ribO 335) operator regions to assay their ability to complement B. subtilis riboflavin auxotrophs. From the results, a revised model of the rib operon was proposed, with ribO now located upstream of all of the structural genes, including ribG, and with the existence of an additional operator hypothesized, possibly located just upstream of ribA.

Morozov et al. (Mol. Genet. Mik. Virusol. no. 12:14 (1985)) report that the B. subtilis rib operon contains a total of three different promoters (in addition to a fourth "promoter" that is only active in E. coli). The primary promoter of the operon was reported to be located within the ribO region, with the two secondary promoters reported between the ribB and ribF genes and within the region of the ribTD and ribH genes, respectively.

Chikindas et al. (Mol. Genet. Mik. Virusol. no. 2:20 (1987)) propose a restriction enzyme map for a 6.3 Md DNA fragment that contains the rib operon of B. subtilis. Sites are indicated for the enzymes EcoRI, PstI, SalI, EcoRV, PvuII and HindIII.

Chikindas et al. (Mol. Genet. Mik. Virusol. no. 4:22 (1987) report that all of the structural genes of the B. subtilis rib operon are located on a 2.8 Md BglII-HindIII fragment and that the BglII site is located between the primary promoter of the operon and the ribosomal-binding site of its first structural gene. As described infra, Applicants show that this BglII site is actually located within the most-5' open reading frame of the rib operon, so that the 2.8 Md fragment described does not contain all of the rib structural genes. Thus, in contrast to the report of Chikindas et al., the 1.3 Md BglII fragment does not contain the ribosomal-binding site of the first structural gene; insertions at this site lead to a riboflavin-negative phenotype. Consequently, any attempt to use this BglII site to engineer the rib operon in order to increase expression, for example by replacing the 5' regulatory region with a stronger promoter, would actually destroy the integrity of the first structural gene and thus the operon as well.

Chikindas et al. (Dokl. Akad. Nauk 5 SSSR 298:997 (1988)) disclose another model of the B. subtilis rib operon, containing the primary promoter, $p_1$, and two minor promoters, $p_2$ and $p_3$: ribO($p_1$)-ribG-ribB-$p_2$-ribF-ribA-ribT-ribD-$p_3$-ribH. As before, it is incorrectly reported that the 1.3 Md BglII fragment contains the entire first structural gene of the operon and that this proximal BglII site maps within the primary regulatory region.

SUMMARY OF THE INVENTION

It is therefore an object of the present invention to provide a recombinant bacterium comprising a bacterium which has been transformed by three or four vectors, two of which each comprise either a DNA sequence coding for the riboflavin synthesizing enzymatic activities of Bacillus subtilis or a DNA sequence which is substantially homologous and one or more transcription elements and a third and/or fourth vector comprising either a DNA sequence coding for the ribA gene product of Bacillus subtilis or a DNA sequence which is substantially homologous and optionally further comprising transcription element whereby one or a plurality of copies of each of these vectors has/have been integrated at three or four different sites within its chromosome. More preferably it is an object of the present invention to provide a recombinant bacterium as described above whereby the two vectors which comprise either the DNA sequence coding for the riboflavin synthesizing enzymatic activities of Bacillus subtilis or a DNA sequence which is substantially homologous further comprise two transcription elements for each vector, preferably promoters and the third and/or fourth vector comprise either the DNA sequence coding for the ribA gene product of Bacillus subtilis or a DNA sequence which is substantially homologous and a transcription element, preferably a promotor.

Furthermore it is an object of the present invention to provide a recombinant bacterium as described above whereby the two vectors which comprise either the DNA sequence coding for the riboflavin synthesizing enzymatic activities of Bacillus subtilis or a DNA sequence which is substantially homologous have been integrated at two different sites of the chromosome in a plurality of copies and the third and/or fourth vector, has/have been integrated at the third and/or fourth site as a single copy.

Furthermore it is an object of the present invention to provide a recombinant bacterium characterized therein that the additional DNA sequence coding for the ribA gene product of Bacillus substilis or a DNA sequence which is substantially homologous is not integrated at a third and/or fourth additional site in the chromosome but integrated at the same site as one of the two vectors with DNA sequences coding for the riboflavin synthesizing enzymatic activities and amplified together with this vector in this site. Such constructs can be made by one skilled in the art based upon generally available knowledge and detailed teachings as given, e.g., in EP 405 370 (EP 370), the corresponding U.S. application Ser. No. 370,378, abandoned, (US. 378) filed Jun. 22, 1989 and its continuation in part U.S. Ser. No. 07/581,048, abandoned, (US. 048) filed Sep. 11, 1990. These applications, EP 405,370, U.S. Pat. No. 370,378 and U.S. Pat. No. 581,048 are hereby incorporated by reference, the pertinent portions of which are reproduced herein.

Furthermore it is understood by one skilled in the art that for transformation the DNA sequences used need not necessarily be in the form of vectors but could also be used without additional vector DNA.

Furthermore it is an object of the present invention to provide a recombinant bacterium as described above which is E. coli or Bacillus, preferably Bacillus subtilis, Cyanobacter or Corynebacteria.

Furthermore it is an object of the present invention to provide a process for the production of riboflavin characterized therein that a recombinant bacterium as described above is grown under suitable growth conditions and the riboflavin secreted into the medium is isolated by methods known in the art. It is also an object of the present invention to provide a process for the preparation of a food or feed composition characterized therein that such a process has been effected and the riboflavin obtained thereby is converted into a food or feed composition by methods known in the art.

BRIEF DESCRIPTION OF THE FIGURES

Figure 3A:
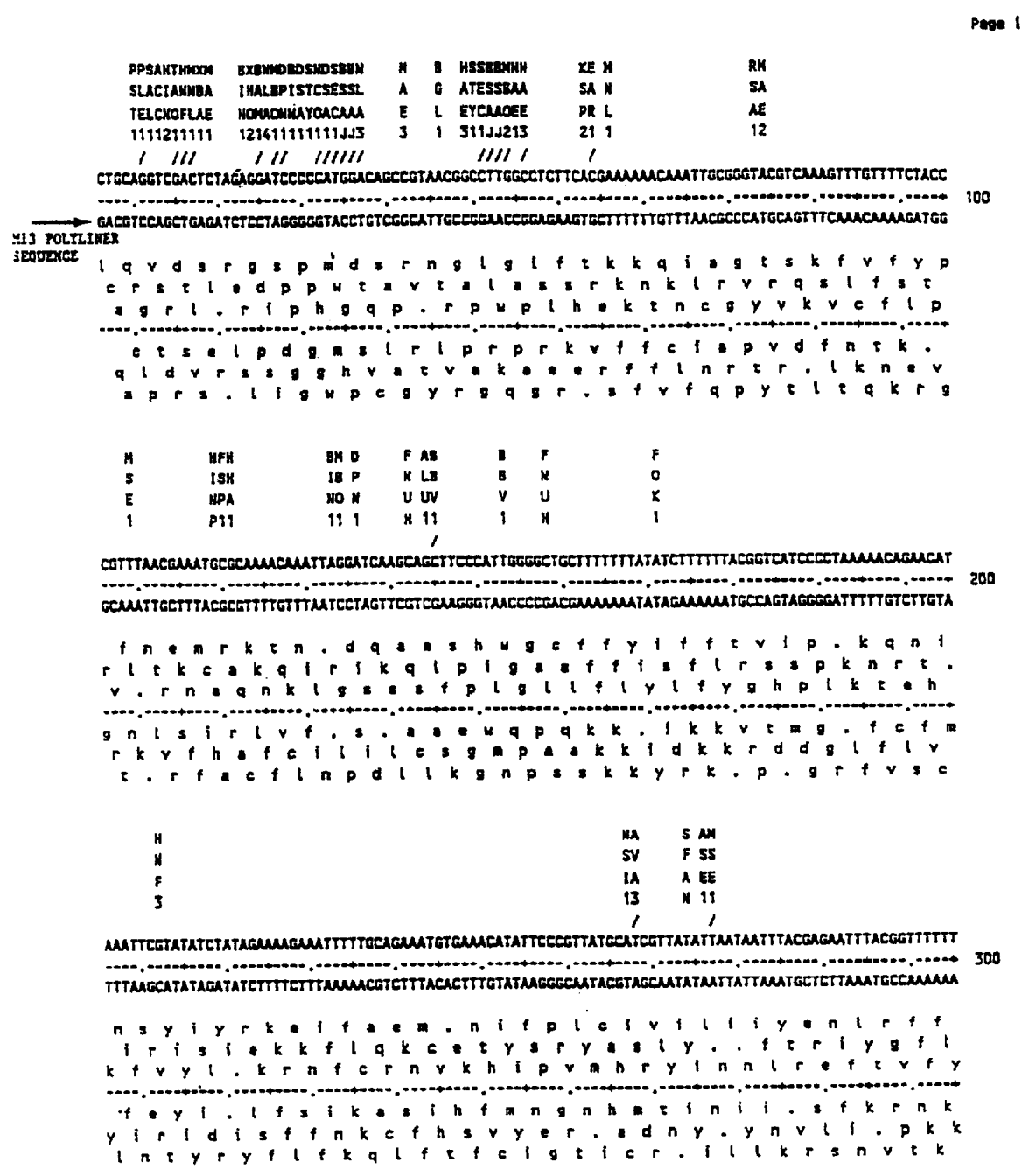
Figure 3C:
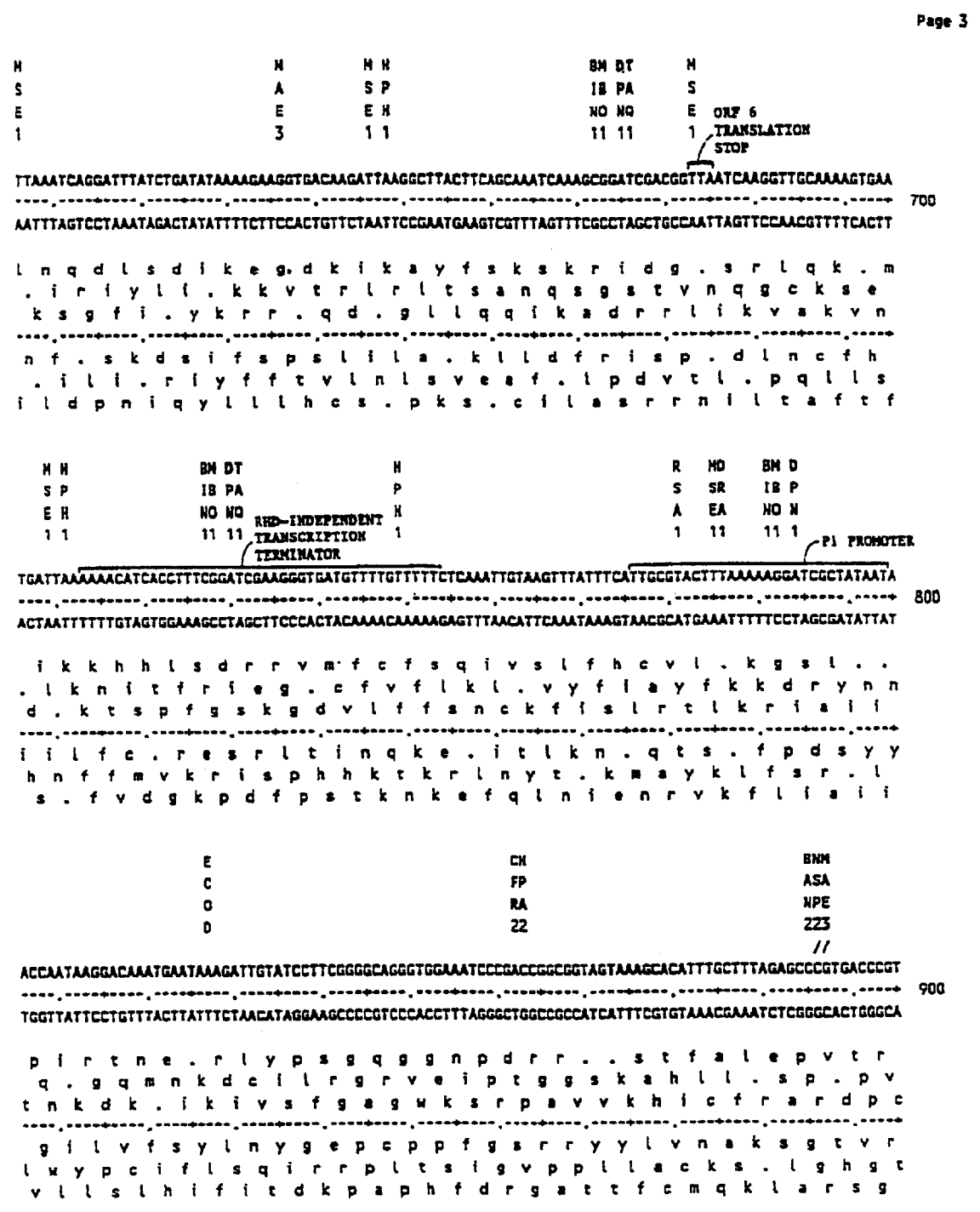
Figure 3D:
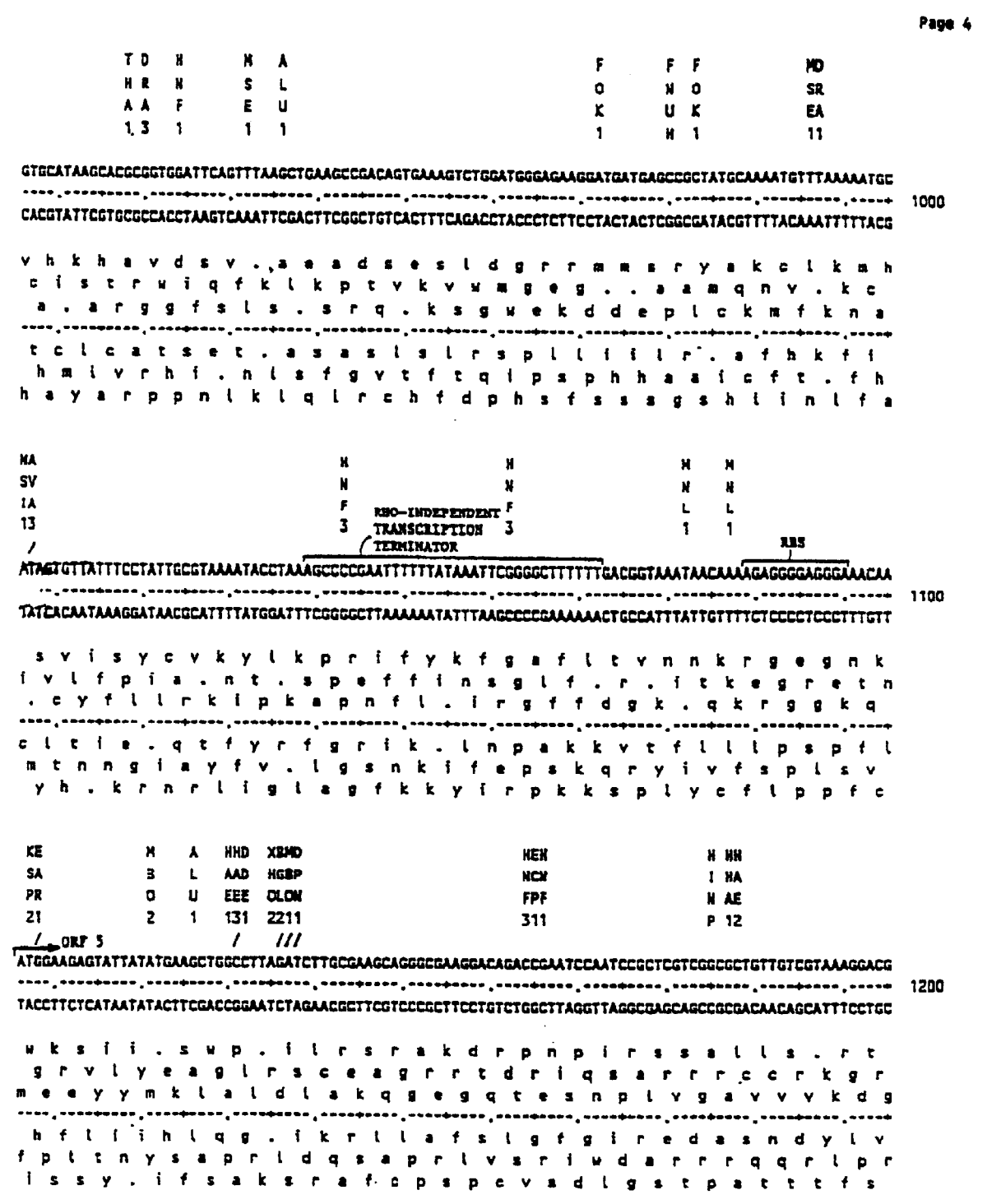
Figure 3E:
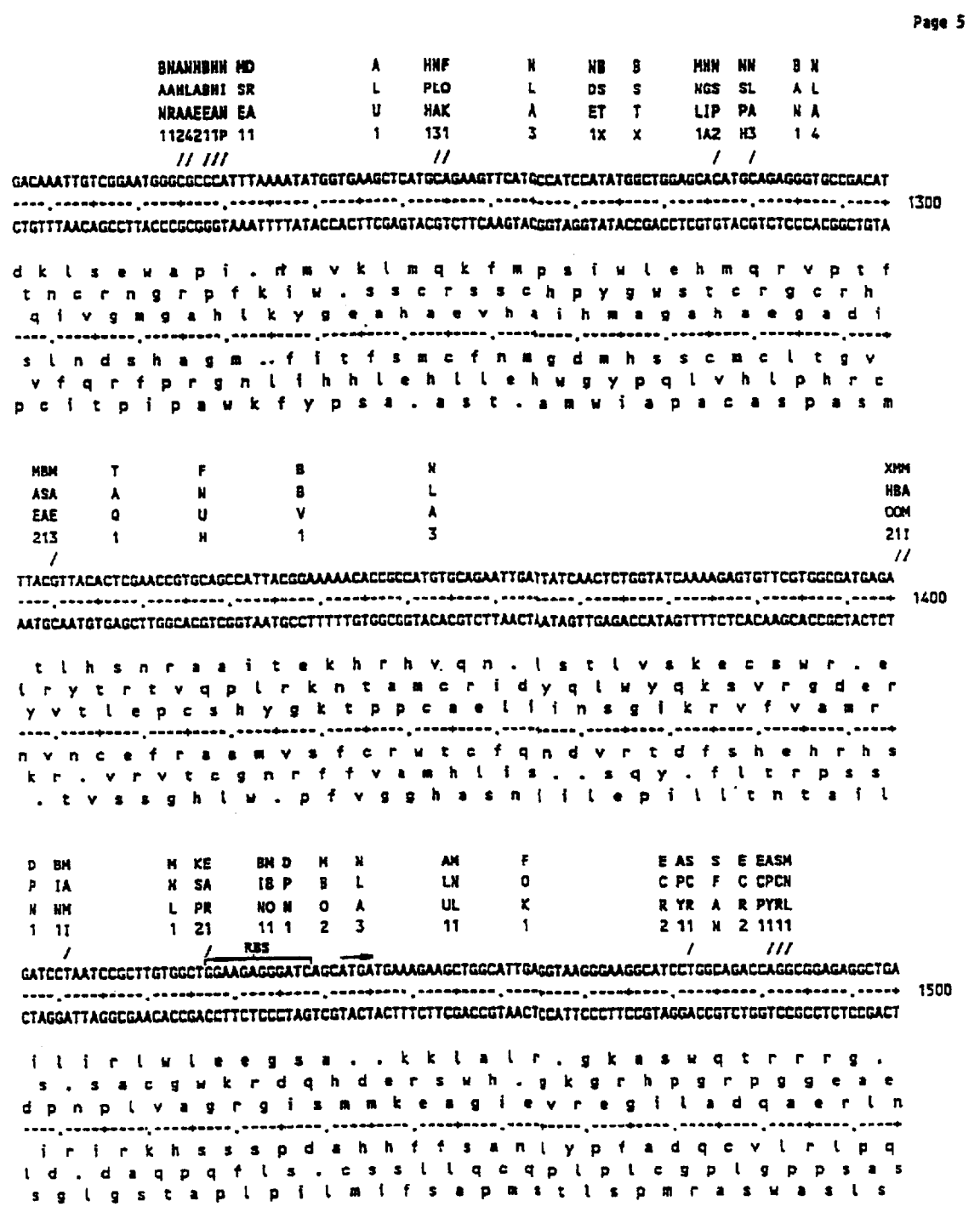
Figure 3F:
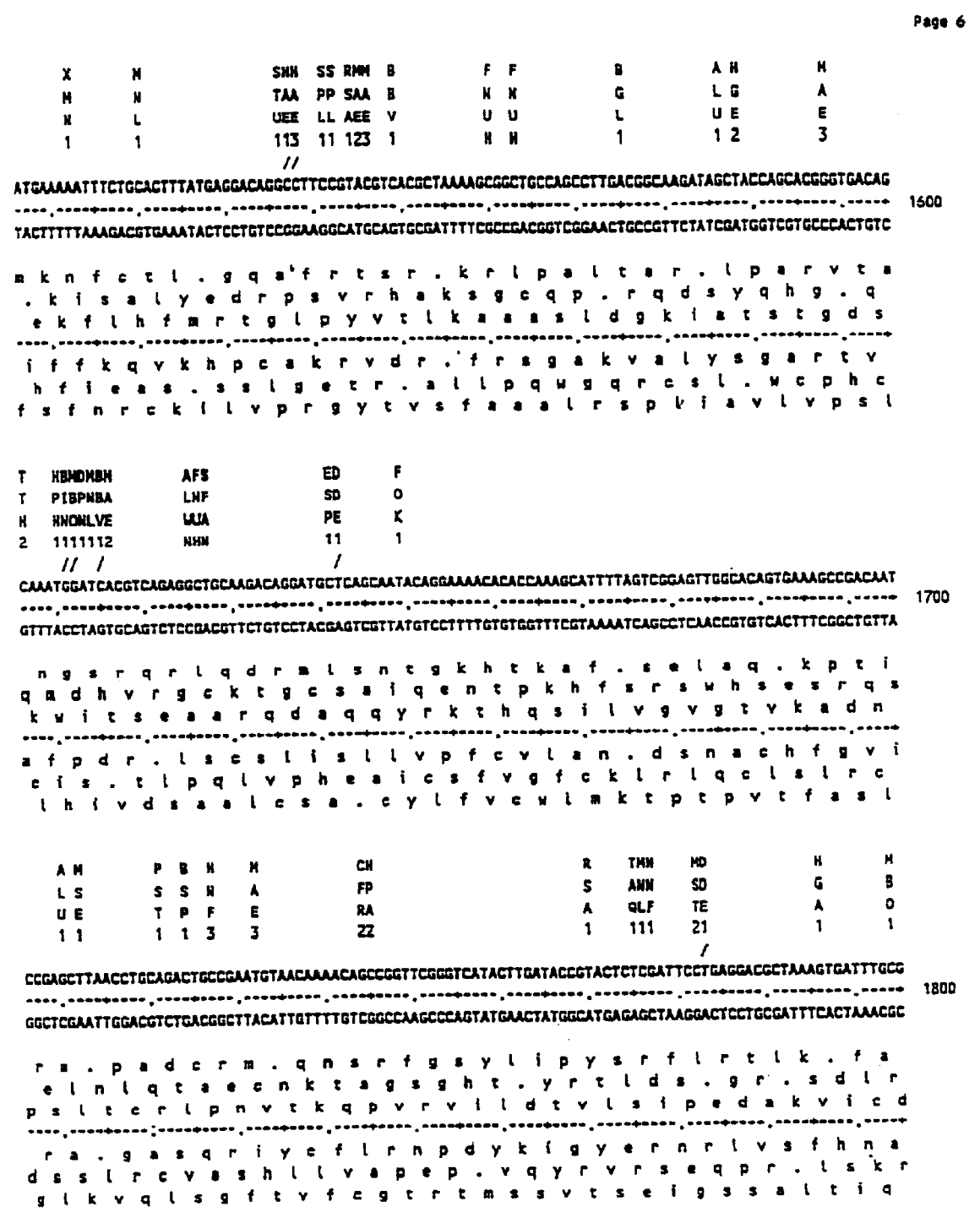
Figure 3G:
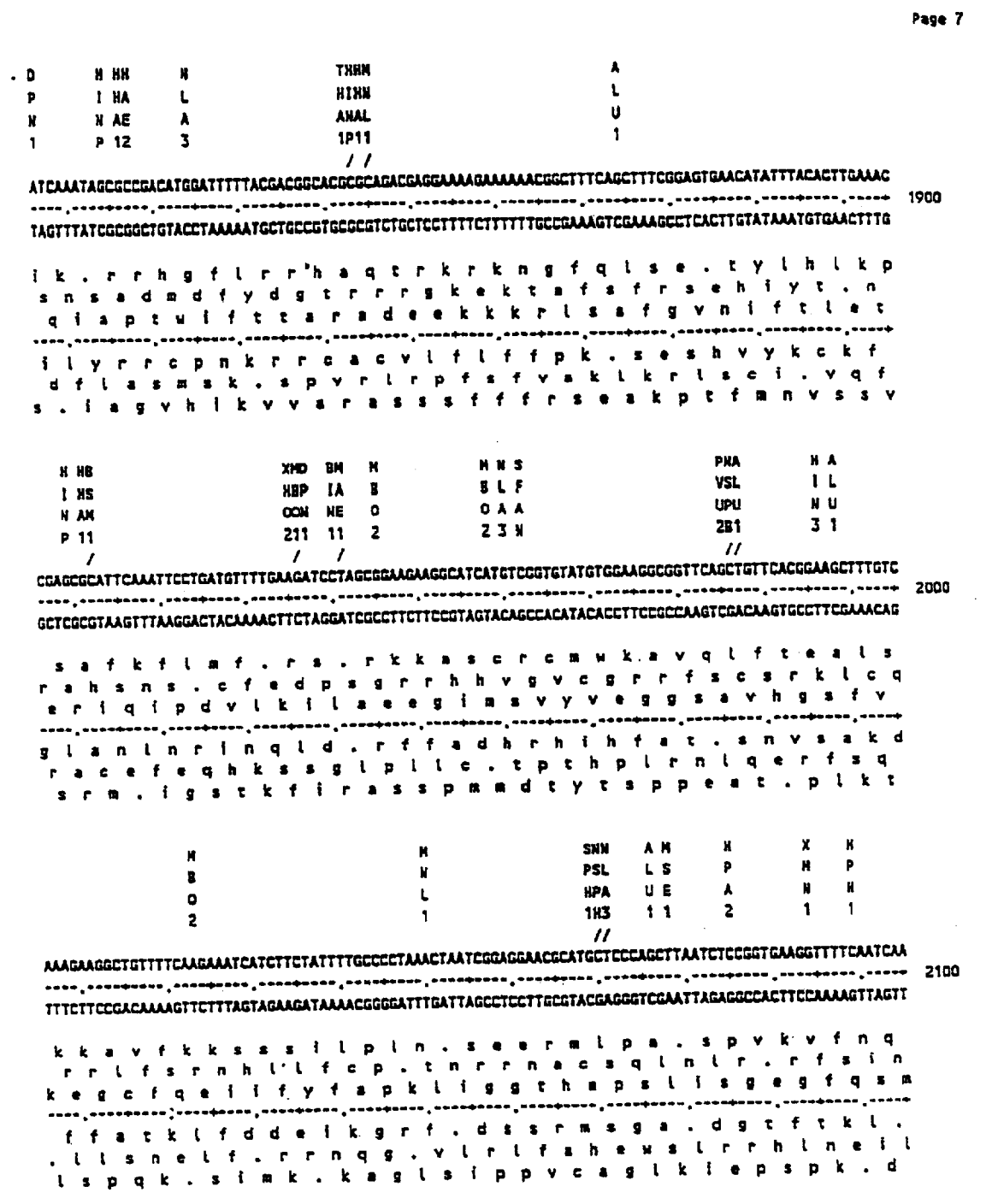
Figure 3H:
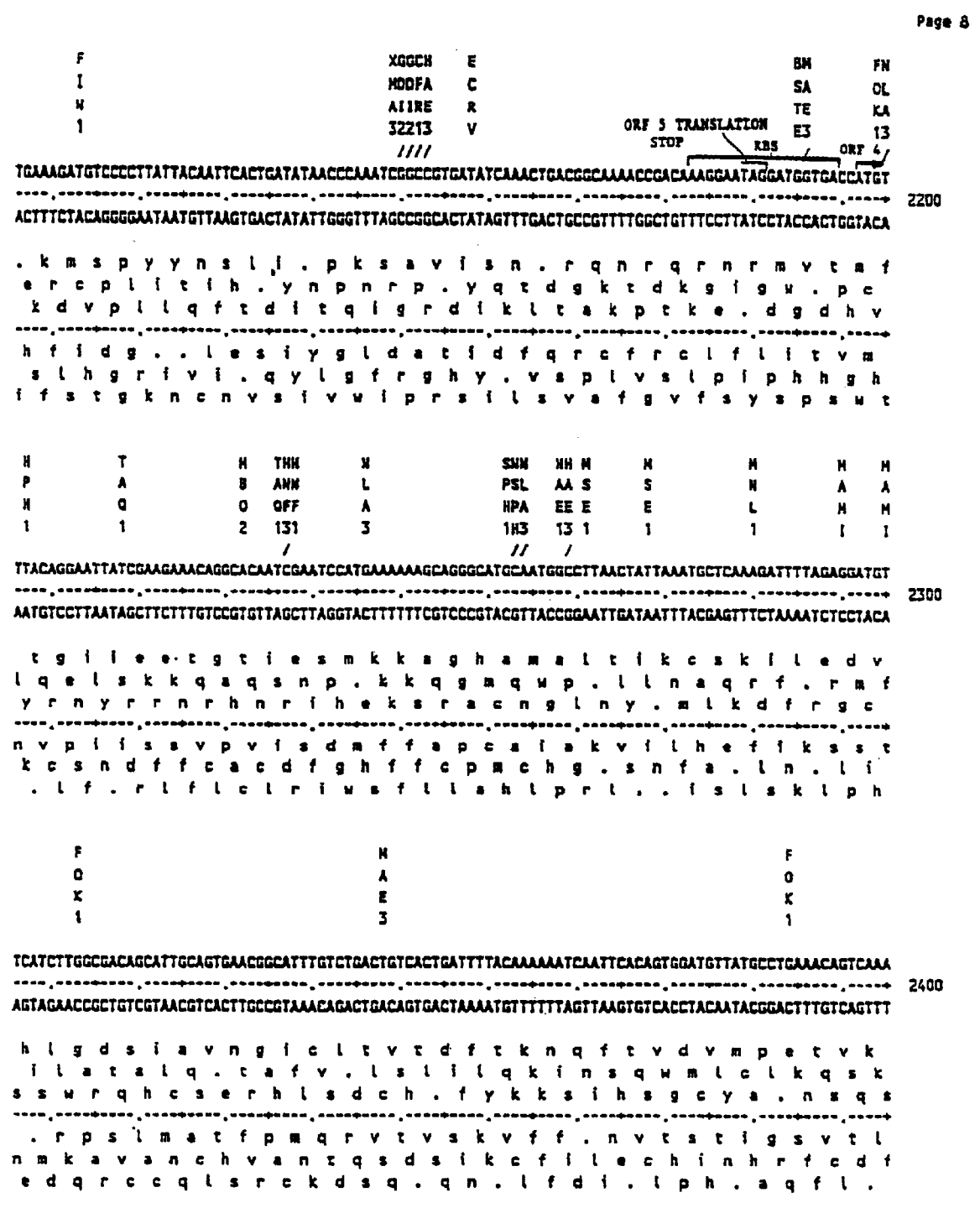
Figure 3I:
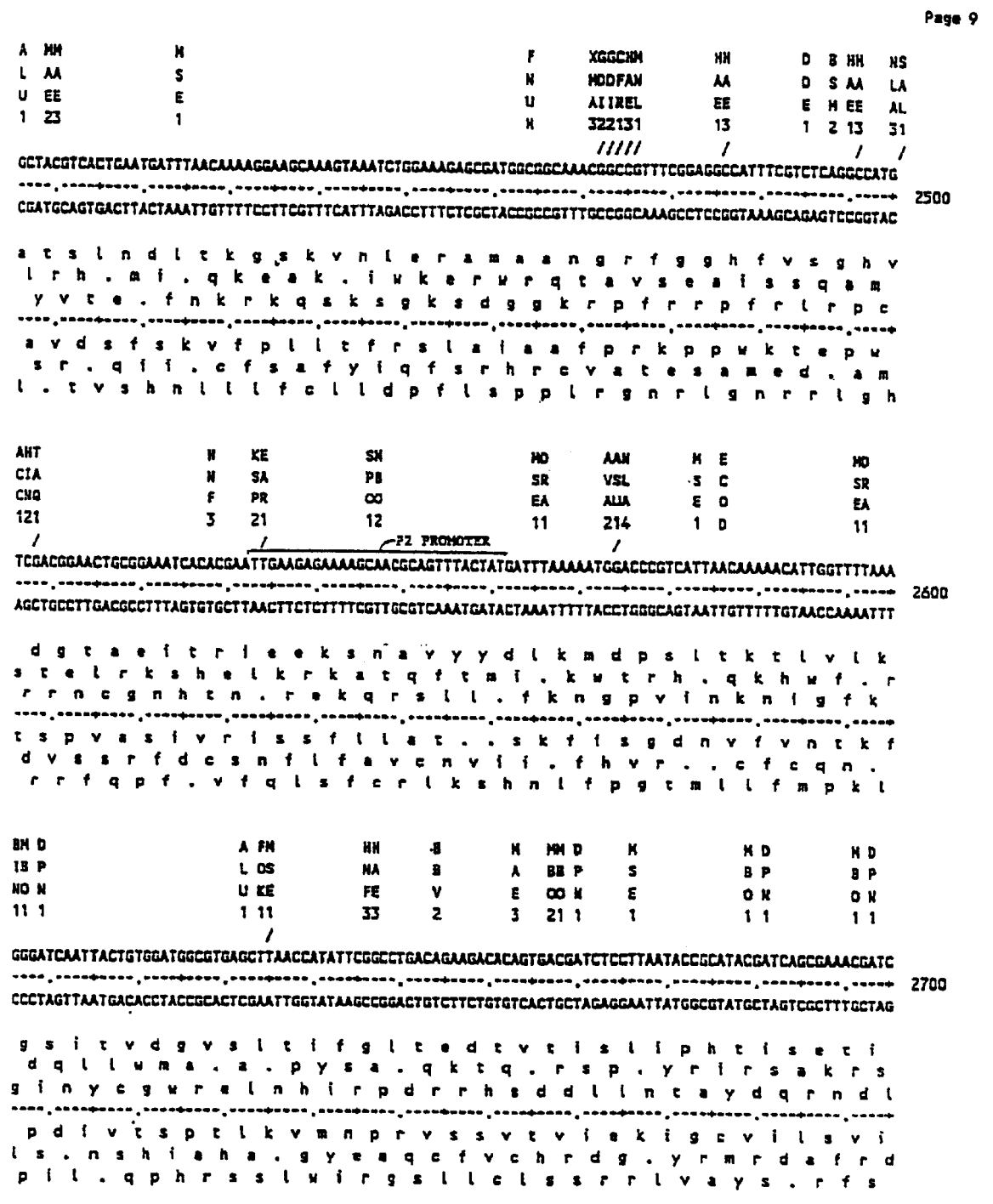
Figure 3J:
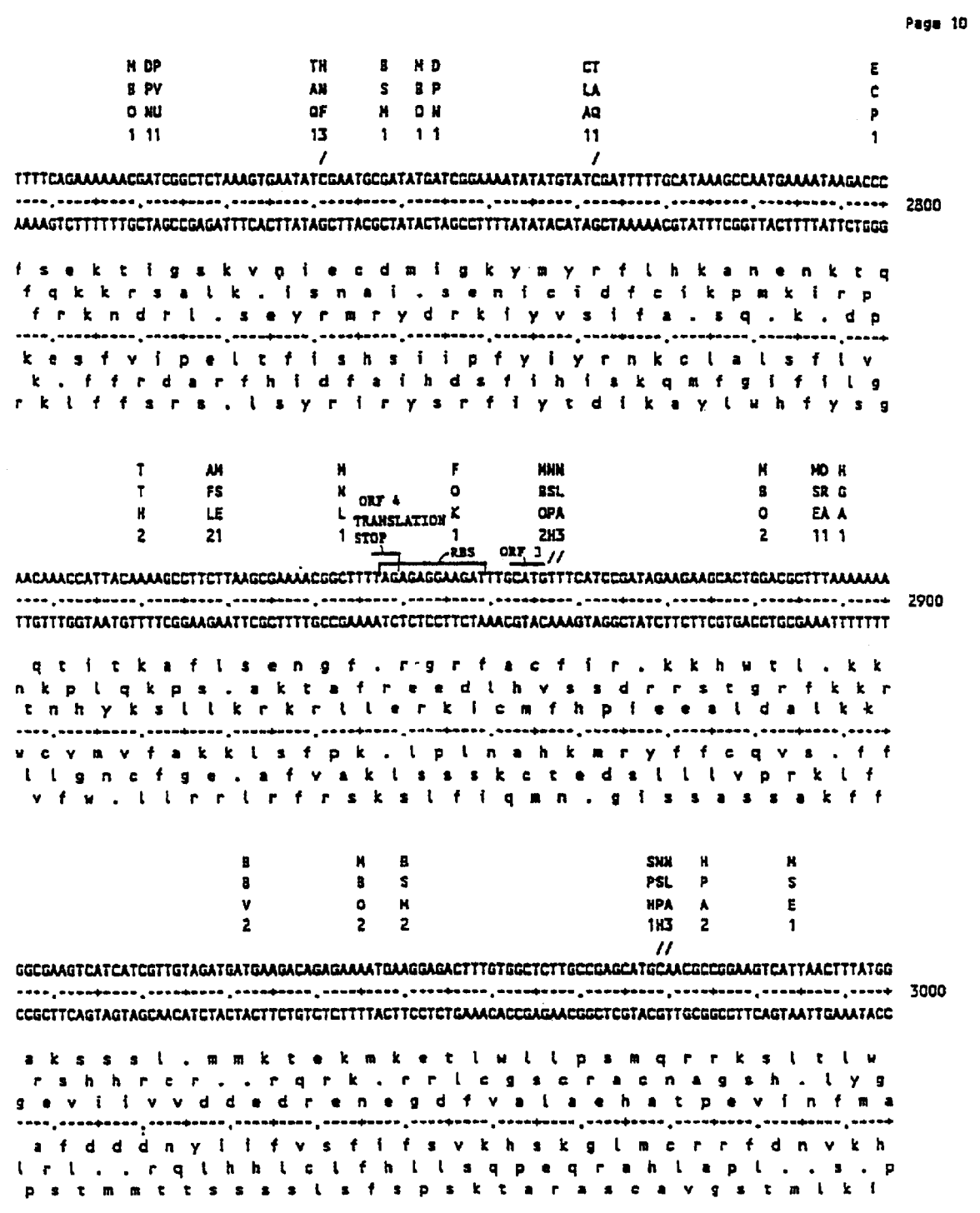
Figure 3K:
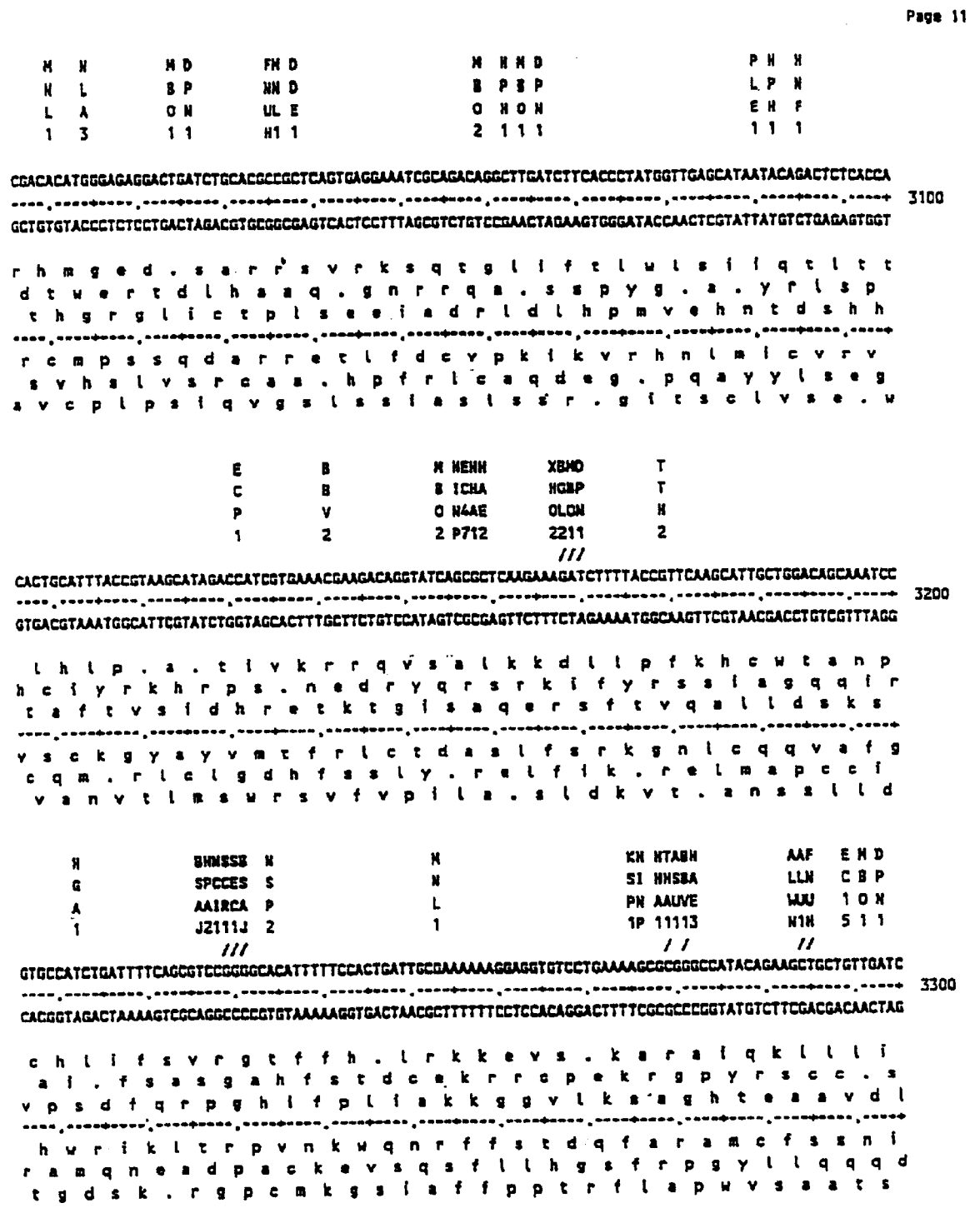
Figure 3L:
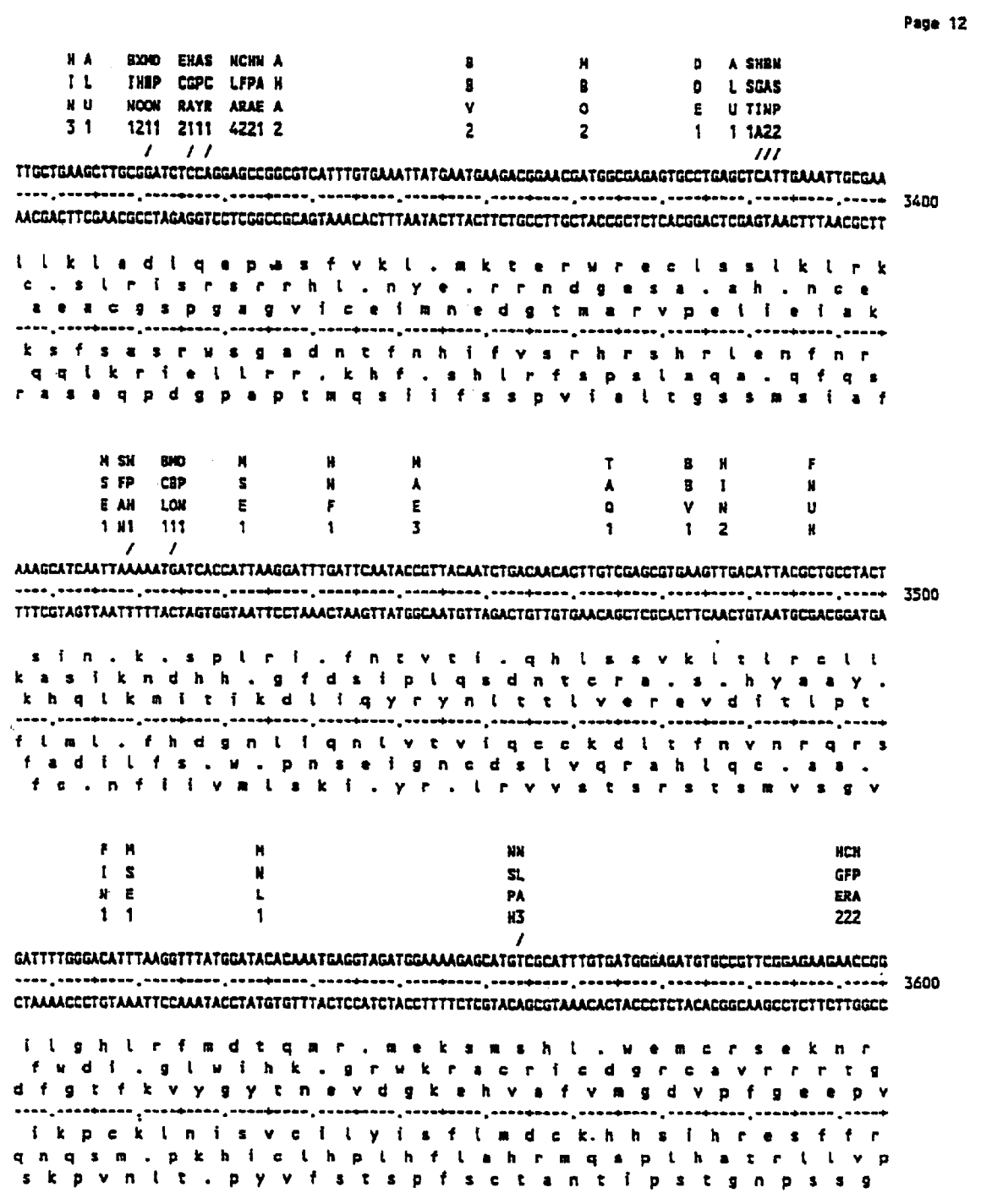
Figure 3M:
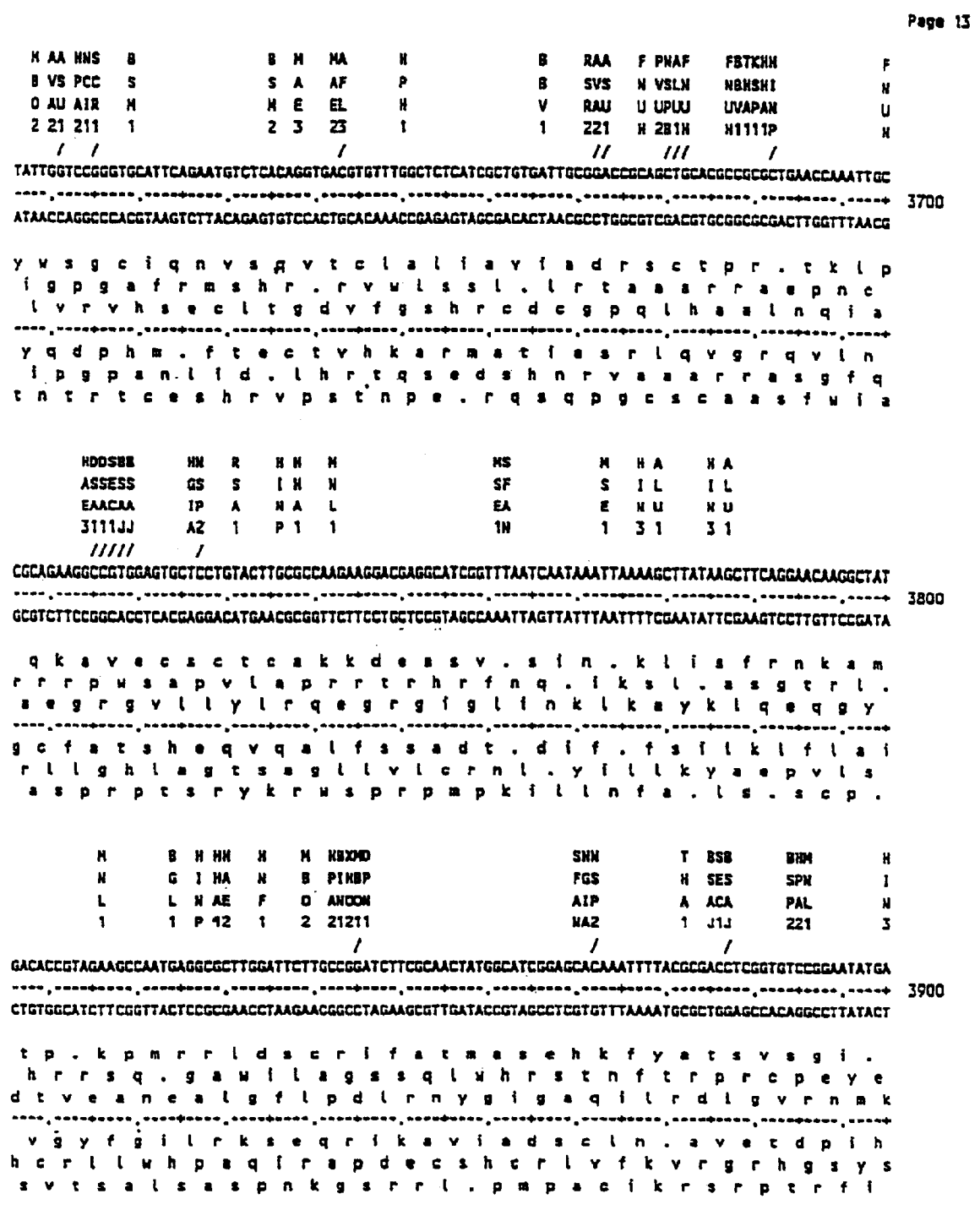
Figure 3Q:
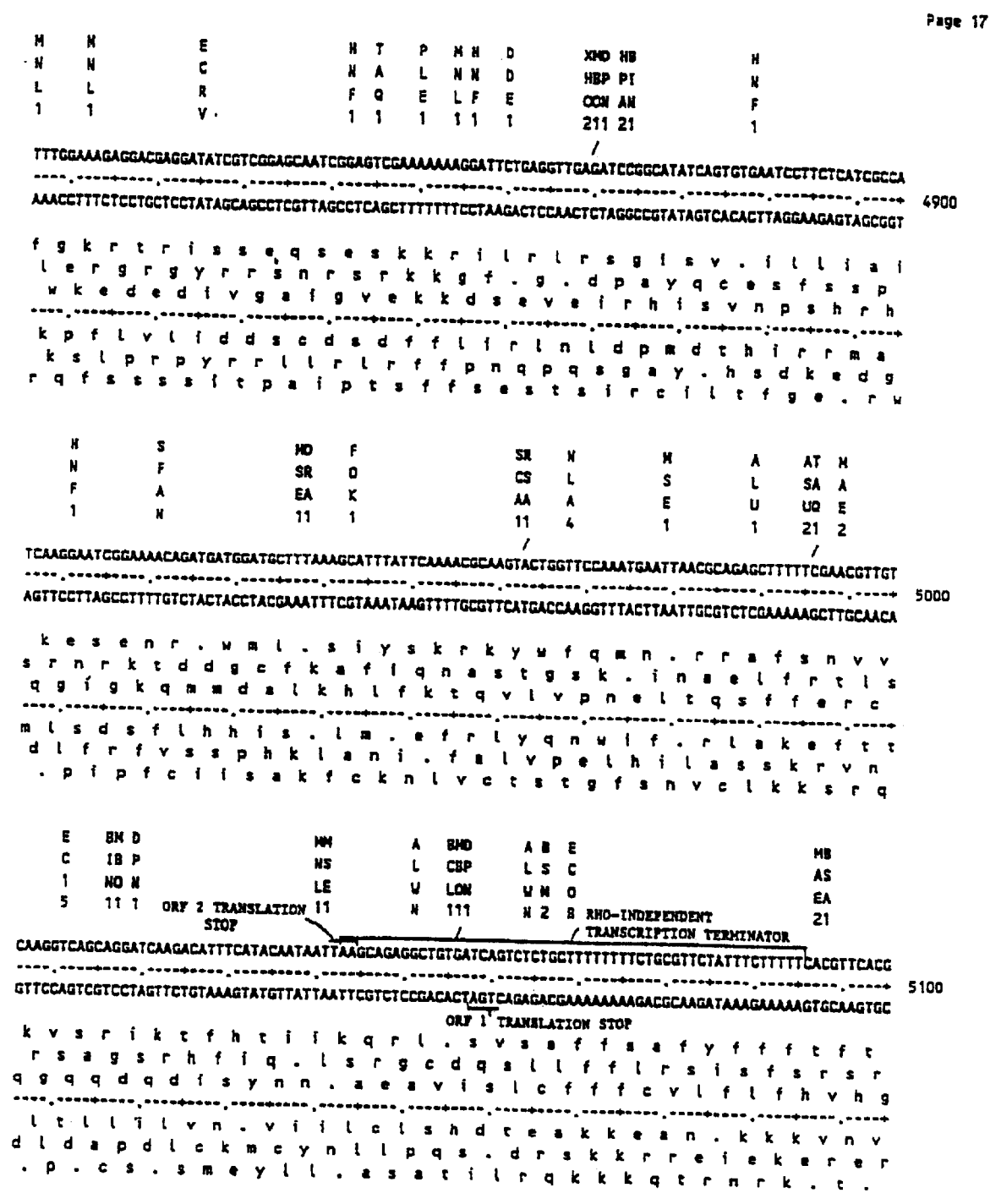
Figure 3R:
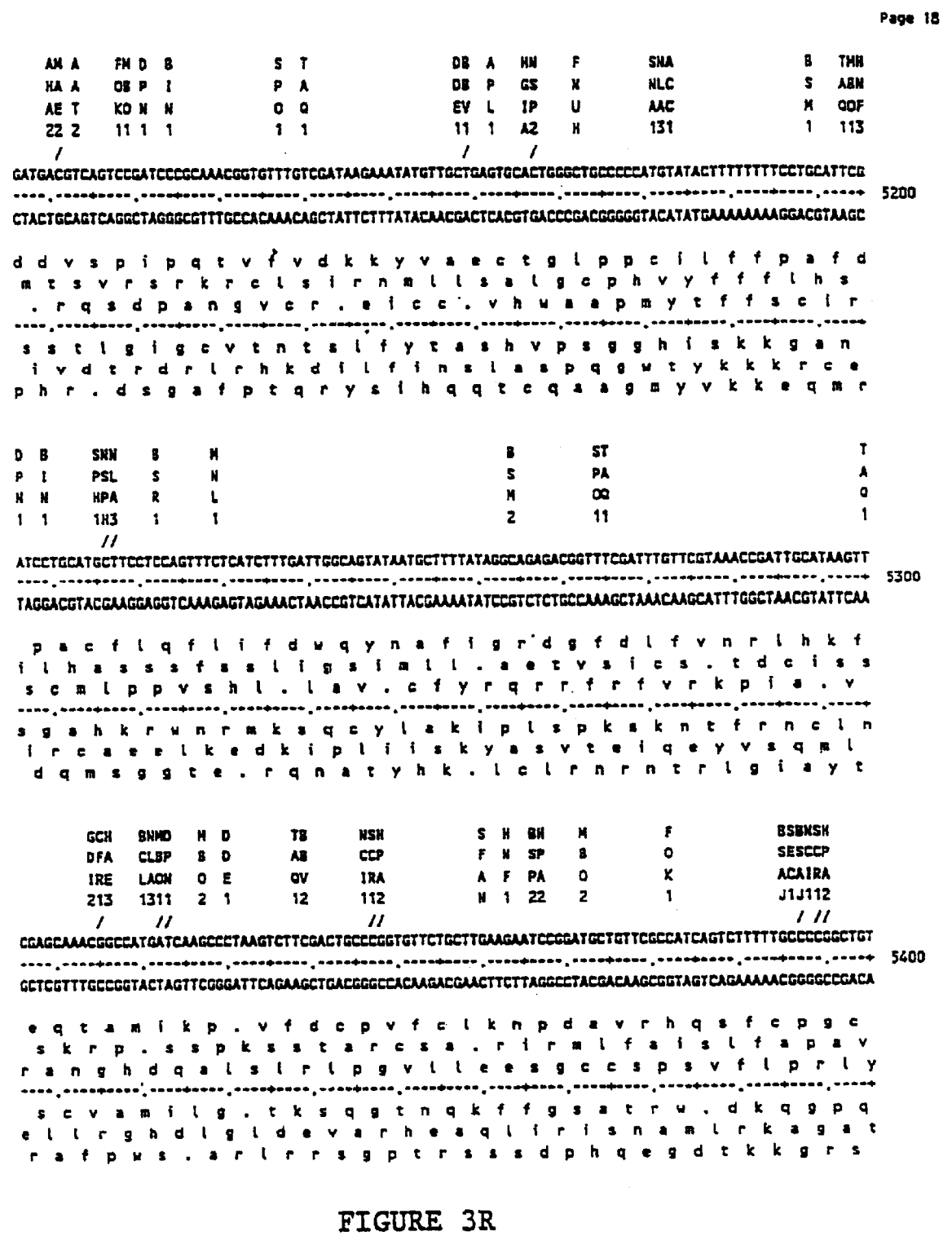
Figure 3S:
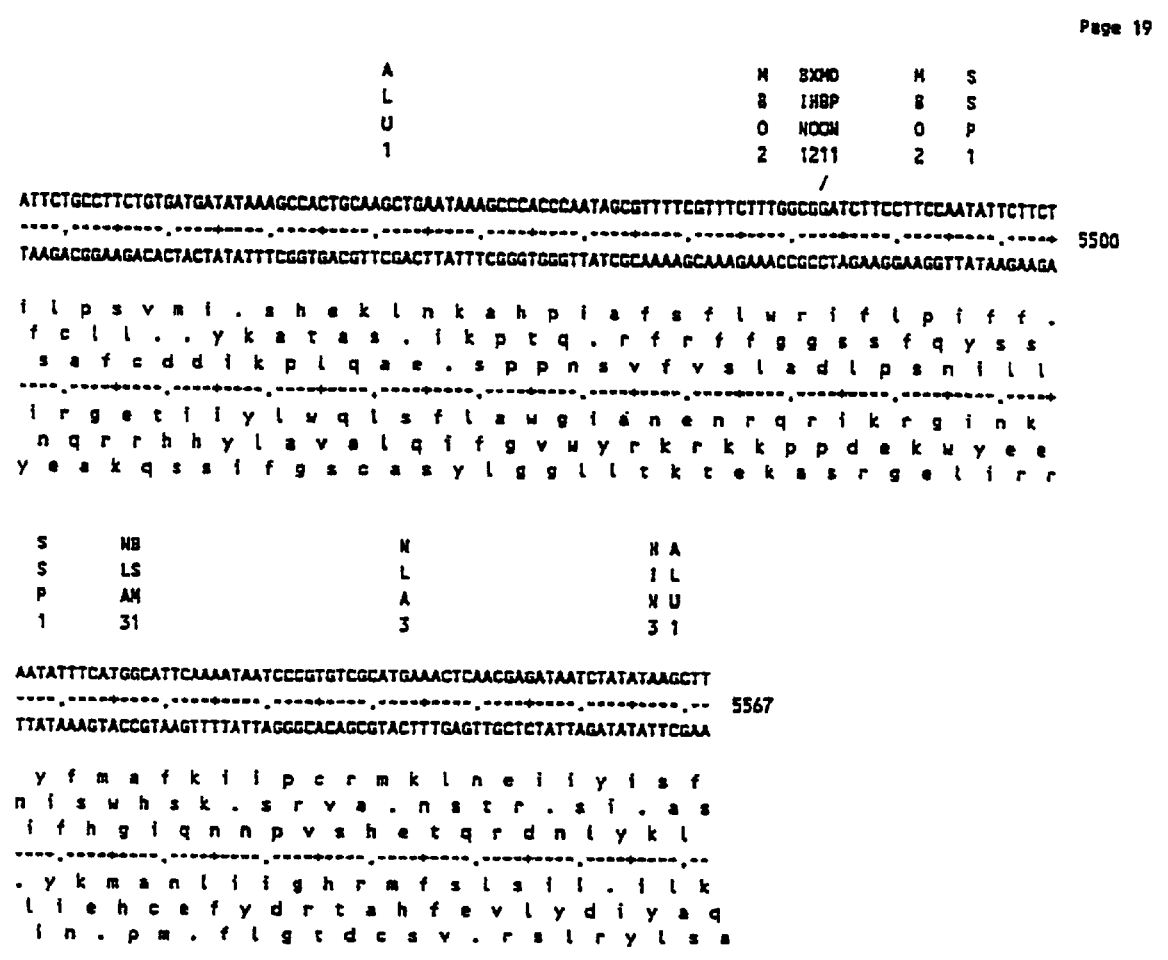

FIG. 3 (Parts A–S). The complete nucleotide and deduced amino acid sequences of the B. subtilis rib operon. The nucleotide sequence was determined by dideoxy sequencing of M13 clones. The deduced amino acid sequence is indicated by the one letter code (Lehninger, Biochemistry, 2d Ed., Worth Publishers, Inc., New York, p. 72). The complete nucleotide sequence is set forth in SEQ ID NO. 1. These deduced amino acid sequence which corresponds to a reading frame staring at nucleotide 1 is set forth in SEQ ID NOs. 2 through 74. The deduced amino acid sequence which corresponds to a reading frame starting at nucleotide 2 is set forth in SEQ ID NOs. 75 through 170. The deduced amino acid sequence which corresponds to a reading frame starting at nucleotide 3 is set forth in SEQ ID NOs. 171 through 217.

FIG. 9. Hairpin-loop structures of the possible rho-independent transcription termination sites. Their locations in the nucleotide sequence of FIG. 3 are shown below each structure. Also presented are their free energies of formation, determined according to Tinoco et al. (*Nature* (*London*) *New Biology* 246:40 (1973)). The nucleotide sequence of FIG. 9, "Upstream from ribP1" is SEQ ID NO. 218. The nucleotide sequence of FIG. 9, "Within 5' leader mRNA" is SEQ ID NO. 219. The nudeotide sequence of FIG. 9, "At 3'end of rib operon" is SEQ ID NO. 220.

FIG. 18. Various oligonucleotides used in vector construction. The nucleotide sequence of FIG. 18, "RB-5" is SEQ ID NO. 222. The nucleotide sequence of FIG. 18, "RB-6" is SEQ ID NO. 223. The nucleotide sequence of FIG. 18, "P2-A" is SEQ ID NO. 224. The nucleotide sequence of FIG. 18, "P2-B" is SEQ ID NO. 225. The nucleotide sequence of FIG. 18, "P2-CII" is SEQ ID NO. 226. The nucleotide sequence of FIG. 18, "P2-DII" is SEQ ID NO. 227.

DETAILED DESCRIPTION OF THE INVENTION

Figure 1:
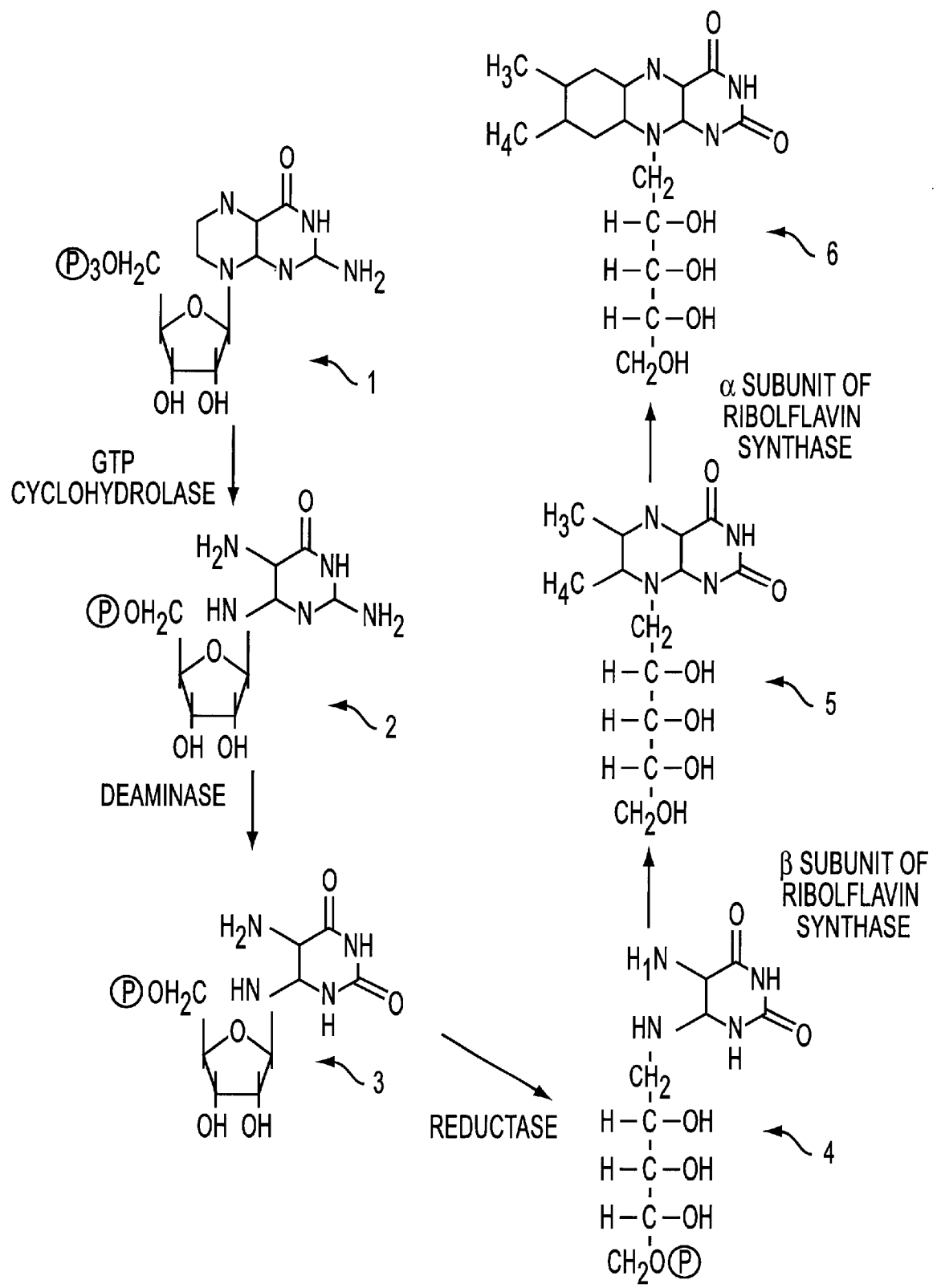
FIG. 1. The riboflavin biosynthetic pathway, modified from Keller et al., Biochem. 27:1117 (1988). The corresponding intermediates shown are those produced by E. coli (which are presumably the same as those produced by B. subtilis): structure 1, guanosine triphosphate (GTP); structure 2,2,5-diamino-6-(ribosylamino)-4(3H)-pyrimidinone-5'-phosphate; structure 3,5-amino-6-(ribosylamino)-2,4(1H, 3H)-pyrimidinedione-5'-phosphate; structure 4,5-amino-6-(ribitylamino)-2,4(1H,3H)-pyrimidinedione-5'-phosphate; structure 5,6,7-dimethyl-8-ribityllumazine; structure 6, riboflavin. The biosynthetic enzymes indicated are those encoded by B. subtilis (GTP cyclohydrolase, α and β subunits of riboflavin synthase) or those proposed to be encoded by B. subtilis (a rib-specific deaminase, and a rib-specific reductase).

DNA sequences which are useful for the purpose of the present invention comprise DNA sequences which code for the riboflavin synthesizing enzymatic activities of *Bacillus subtilis* described above and which are selected from the following DNA sequences:

(a) a DNA sequence which hybridizes under standard conditions with sequences defined above;

(b) a DNA sequence which, because of the degeneracy of the genetic code, does not hybridize with sequence (a), but which codes for polypeptides having exactly the same amino acid sequences as the polypeptides encoded by these DNA sequences; and (c) a DNA sequence which is a fragment of the DNA sequences specified in (a) or (b) and which codes for a polypeptide having the riboflavin synthesizing enzymatic activities of *Bacillus subtilis*.

"Standard conditions" for hybridization in this context the conditions which are generally used by a man skilled in the art to detect specific hybridization signals and which are described, e.g., by Sambrook et al., "Molecular Cloning" second edition, Cold Spring Harbor Laboratory Press 1989, New York, or preferably so called stringent hybridization and non-stringent washing conditions, or more preferably so called stringent hybridization and stringent washing conditions of which one skilled in the art is familiar with and which are described, e.g., in Sambrook et al. (s.a.).

DNA sequences which can be used for the purpose of the present invention are disclosed, e.g., in the specification of EP 370, US 378 and US 048 of which, the pertinent portions are hereinbelow reproduced The riboflavin biosynthetic genes from various bacteria can be cloned for use in the present invention. Yeast or bacterial cells from species including but not limited to the genus Bacillus, *E. coli* and many other gram-positive and gram-negative bacteria can potentially serve as the nucleic acid source for the molecular cloning of the rib operon. The DNA containing the fib operon may be obtained, by standard procedures known in the art, for example, from a DNA library prepared by cloning chromosomal DNA or fragments thereof, purified from the desired bacterial cell, into a suitable vector for propagation of the gene. (See, for example, Maniatis et al., 1982, *Molecular Cloning, A Laboratory Manual*, Cold Spring Harbor Laboratory, Cold Spring Harbor, N.Y.; Glover, D. M.

(ed.), 1982, *DNA Cloning: A Practical Approach*, MRL Press, Ltd., Oxford, U.K., Vol. I, II).

In the molecular cloning of the gene from chromosomal DNA, fragments are generated, some of which will encode the desired rib operon. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to agarose and polyacrylamide gel electrophoresis and density gradient centrifugation.

Once the DNA fragments are generated, DNA libraries are prepared using an appropriate cloning and/or expression vector. A large number of vector-host systems known in the art may be used. Possible vectors include, but are not limited to, plasmids or modified viruses, but the vector system must be compatible with the host cell used. For *E. coli* such vectors include, but are not limited to, bacteriophages such as λ derivatives, high-copy plasmids such as pBR322 or pUC plasmids, or low-copy plasmids derived from Pseudomonas plasmid RK2. For Bacillus such vectors include, but are not limited to, bacteriophages such as ρ11 (Dean et al., *J. Virol.* 20: 339, 1976; Kawamura et al., *Gene* 5:87, 1979) or φ105 derivatives (Iijima et al., *Gene* 2:115, 1980; Errington, *J. Gen. Microbiology* 130:2615, 1984; Dhaese et al., *Gene* 32: 181, 1984; Errington, J. in *Bacillus Molecular Biology and Biotechnology Applications*, A. T. Ganesan and J. A. Hoch, eds. (Academic Press, New York,), p. 217, 1986), high-copy plasmids such as pUB110 (Ehrlich, *Proc. Natl. Acad. Sci.* (*USA*) 74: 1680, 1977) or pBD64, or low-copy plasmids such as pE194 derivatives (Gryczan, T. J. in *The Molecular Biology of the Bacilli*, D. A. Dubnau, ed. (Academic Press, New York), pp. 307–329, 1982; Horinouchi and Weisblum, *J. Bacteriol.* 150: 804, 1982). Recombinant molecules can be introduced into host cells via transformation, transfection, protoplasting, infection, electroporation, etc.

Once the DNA libraries are generated, identification of the specific clones harboring recombinant DNA containing the a operon may be accomplished in a number of ways (as described, for example, in Maniatis et. al., supra). For example, if an amount of the operon or a fragment thereof is available from another bacterial source (e.g., from *E. coli*) and is sufficiently homologous to the riboflavin biosynthetic genes of Bacillus to hybridize thereto, that DNA can be purified and labeled, and the generated bank of DNA fragments may be screened by nucleic acid hybridization to the labeled probes (Benton, W. and Davis, R., 1977, *Science* 196:180; Grunstein, M. and Hogness, D., 1975, *Proc. Natl. Acad. Sci. U.S.A.* 72:3961). Alternatively, sequences comprising open reading frames of the endogenous rib operon, or subsequences thereof comprising about 10, preferably 15 or more nucleotides, may be used as hybridization probes. Such probes can be made synthetically, based on a portion of the nucleic acid or amino acid sequence (examples of which are provided below) of a gene product known to be encoded by the operon ("reverse genetics"). If a purified rib operon-specific probe is unavailable, cloned gene libraries of restriction fragments (from partial Sau3A-digests, for example) can be made in bacteria, especially *B. subtilis* or *E. coli*, and the rib operon-containing recombinant clones can be identified by either marker-rescue or complementation of known rib mutations.

In a preferred embodiment, the rib operon of *B. subtilis* can be isolated for use from an *E. coli* plasmid library of *B. subtilis* DNA. In particular, and as described below, the *B. subtilis* rib operon can be isolated by virtue of its homology to a radiolabelled, synthesized nucleotide probe that is derived from an internal region of a gene product known to be encoded by the operon of *B. subtilis*. Although a portion of the amino acid sequence for β-riboflavin synthase (Ludwig et al., *J. Biol. Chem.* 262:1016, 1987) can be the basis for such a probe, with the third nucleotide of each codon estimated from frequency of codon usage, a similar probe based on another region of this protein or another protein from the rib operon can be utilized and would fall within the scope of the present invention. The present invention further enables screening by use of synthetic probes which are derived from the nucleic acid sequence shown in FIG. 3.

Analogous methods to those detailed here can be used to isolate the rib operon of other bacteria, especially other Bacilli or *E. coli*. In a specific embodiment, such clones can be selected by assay for ability to hybridize to the labeled *B. subtilis* rib operon or a hybridizable portion thereof. It is well known in the art that starting from an appropriate mRNA preparation, cDNA can be prepared; such cDNA can also be used in accordance with the present invention to prepare vectors for the transformation of appropriate bacteria for riboflavin overproduction.

Once the host cells with recombinant DNA molecules that include the isolated rib operon or a portion thereof are identified, the DNA may be obtained in large quantities. This then permits the rib operon to be manipulated and its nucleotide sequence to be determined using various cloning and sequencing techniques familiar to those knowledgeable in the art.

For example, insertional mutagenesis can be used to locate and characterize the rib operon and genes thereof within a cloned piece of DNA. In a specific embodiment, rib-biosynthetic containing regions can be identified by inserting small cat (chloramphenicol acetyltransferase)-containing restriction fragments into several different restriction enzyme sites of the cloned DNA, and testing each derivative for insertional inactivation of riboflavin biosynthesis in an appropriate host (see below).

The cloned DNA corresponding to the rib operon can be analyzed by methods including but not limited to Southern hybridization (Southern, E. M., 1975, *J. Mol. Biol.* 98:503–517), Northern hybridization (see e.g., Freeman et al., 1983, *Proc. Natl. Acad. Sci. U.S.A.* 80:4094–4098), restriction endonuclease mapping (Maniatis et al., 1982, *Molecular Cloning, A Laborator Manual*, Cold Spring Harbor Laboratory, Cold Spring Harbor, N.Y.), and DNA sequence analysis. Restriction endonuclease mapping can be used to roughly determine the genetic structure of rib operon. Restriction maps derived by restriction endonuclease cleavage can be confirmed by DNA sequence analysis.

DNA sequence analysis can be performed by any techniques known in the art, including but not limited to the method of Maxam and Gilbert (1980, *Meth. Enzymol.* 65:499–560), the Sanger dideoxy method (Sanger, F., et al., 1977, *Proc. Natl. Acad. Sci. U.S.A.* 74:5463), or use of an automated DNA sequenator (e.g., Applied Biosystems, Foster City, Calif.). As an example, the DNA sequence of the rib operon of *B. subtilis* is presented in FIG. 3.

Once the nucleotide sequence of the rib operon has been determined, putative open reading frames (ORFs) can then be identified along with the deduced amino acid sequence of their encoded product. Actual identification of the encoded product can be carried out, e.g., by performing S-30 coupled in vitro transcription/translation reactions, with various ORFs used as templates. Various mutational derivatives of the ORFs can also be tested for activity in functional assays of the S-30 reaction products, in order to test the function of the encoded products.

Figure 4:
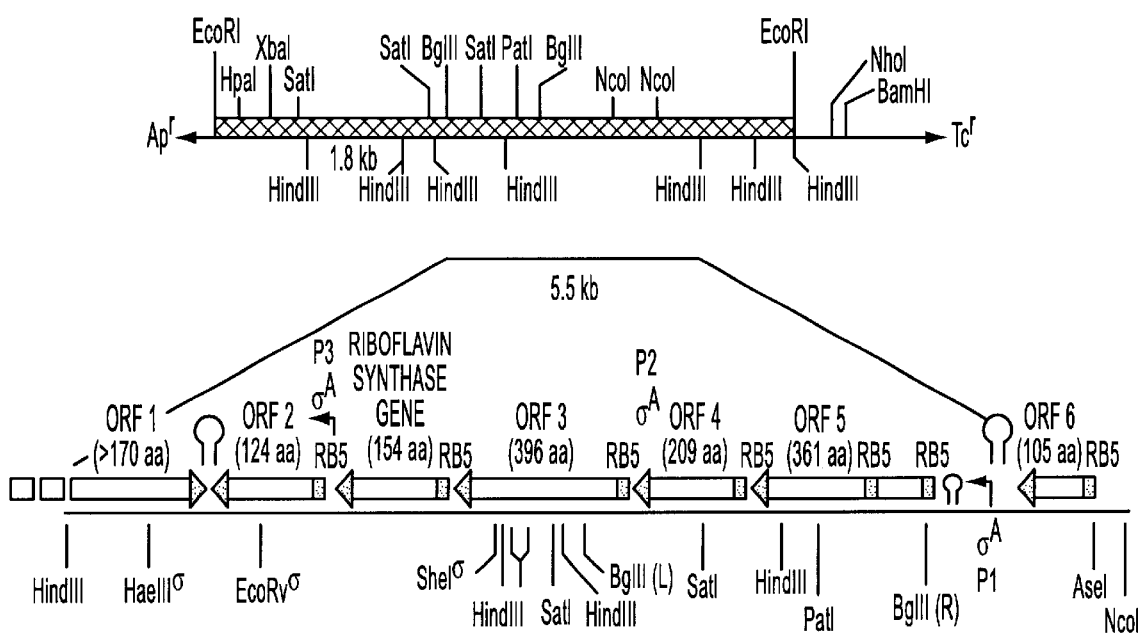
FIG. 4. A schematic representation of the rib gene cluster. The top diagram is the restriction endonuclease map of the cloned 10 kb EcoRI DNA fragment in plasmid pRF2, containing the B. subtilis rib operon. The hatched box depicts Rib+ cloned DNA, while the thin black line represents pBR322 DNA. The bottom diagram is based on the complete nucleotide sequence of the 6.0 kb fragment to which the rib operon was localized. Open reading frames are depicted by open boxes, with arrows indicating the direction of transcription, and closed boxes indicating the putative ribosome binding sites. Probable $\sigma^A$ promoter regions are shown. Tentatively identified rhoindependent transcription termination sites are indicated by a "hairpin" symbol. Not all restriction sites are indicated.

In a specific embodiment of the invention relating to the B. subtilis rib operon, and detailed in the examples below, the above-described methods were used to determine that B. subtilis riboflavin biosynthesis is controlled by a single operon of approximately 4.2 kb containing five biosynthetic genes: the β subunit of riboflavin synthase and ORFs designated 2, 3, 4, and 5 (see FIG. 4). ORFs 2, 3, 4, and 5 were subsequently shown to encode proteins with molecular weights of about 15 kd, 47 kd, 26 kd, and 44 kd, respectively. As described below, ORF 5 was shown to encode a putative rib-specific deaminase that catalyzes the reduction of a deaminated pyrimidine to a ribitylamino-linkage in an early step in riboflavin biosynthesis. Our data also indicated that ORF 4 encodes the ax subunit of riboflavin synthase and ORF 3 encodes a GTP cyclohydrolase, while ORF 2 possibly encodes a rib-specific reductase. ORF 1 and ORF 6 were found to be outside the primary transcription unit of the rib operon. The primary site for initiation of transcription of the rib operon was determined to be probably the apparent $\sigma^A$ promoter located 290 bp upstream from the first gene in the operon, ORF 5 (FIG. 4, $P_1$). The coding regions, promoters and transcription termination sites of the B. subtilis rib operon are shown in Table VI below.

The present invention encompasses the nucleotide and amino acid sequences of the genes of the rib operon, as well as subsequences thereof encoding functionally active peptides, and sequences which are substantially the same as such sequences. A functionally active peptide, as used herein, shall mean a protein or peptide which is capable of catalysing a reaction leading to riboflavin biosynthesis. A functionally active nucleic acid sequence shall mean a sequence capable of regulating riboflavin biosynthesis. A sequence substantially the same as another sequence shall mean a sequence capable of hybridizing to the complementary sequence thereof. In addition, a nucleic acid sequence not naturally controlling the expression of a second nucleic acid sequence shall mean a sequence which does not control the expression of the second sequence in the bacterium from which the second sequence is isolated.

Once the genetic structure of the rib operon is known, it is possible to manipulate the structure for optimal use in the present invention. For example, the rib operon can be engineered to maximize riboflavin production.

Depending on the host-vector system utilized, any one of a number of suitable transcription and translation elements may be used. Promoters produced by recombinant DNA or synthetic techniques may also be used to provide for transcription of the inserted sequences. When propagating in bacteria the regulatory sequences of the rib operon itself may be used. In an embodiment in which the entire rib operon, or greater than one gene thereof, is desired to be expressed as a polycistronic message, a prokaryotic host is required. In an embodiment in which a eukaryotic host is to be used, appropriate regulatory sequences (e.g., a promoter) must be placed in the recombinant DNA upstream of each gene/ORF that is desired to be expressed.

Specific initiation signals are also required for efficient translation of inserted protein coding sequences. These signals include the initiation codon (ATG, GTG or TFG) and adjacent sequences, such as the ribosome binding site (RBS). It should be noted that the RBS of a given coding sequence can be manipulated to effect a more efficient expression of that coding sequence at the translational level.

In cases where an entire open reading frame of the rib operon, including its own initiation codon and adjacent regulatory sequences, is inserted into the appropriate expression vectors, no additional translational control signals may be needed. However, in cases where only a portion of the coding sequence is inserted, or where the native regulatory signals are not recognized by the host cell, exogenous translational control signals, including the initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

In addition, a host cell strain may be chosen which modulates the expression of the rib operon gene(s) or modifies and processes the gene product(s) thereof in the specific fashion desired. Expression from certain promoters can be elevated in the presence of certain inducers; thus, expression of the genetically engineered rib operon proteins may be controlled. In one embodiment, the regulatory regions of the operon, such as the promoter and the termination/anti-termination regulatory sequences, can be manipulated or replaced with constitutive or growth-regulated promoters to deregulate the rib operon and thus increase riboflavin production. Furthermore, appropriate cell lines or host systems can be chosen to ensure the desired modification and processing of the expressed proteins. Many manipulations are possible and within the scope of the present invention.

In one specific embodiment of the invention, the 5' regulatory sequence of the B. subtilis rib operon can be removed and replaced with one or more of several B. subtilis promoters; such a construction will cause high-level expression of the rib biosynthetic genes. This approach would involve the introduction of new restriction sites within a 20–30 bp region between the end of the transcription terminator and the RBS sequence of the first gene in the operon ORF 5. Such restriction sites can be introduced by either site-directed mutagenesis or by deleting all regulatory sequences upstream from the right-most BglII ($BglII_R$) site located within the first 30 bp of ORF 5 (see FIGS. 3 and 4) and inserting at this site a synthetic oligonucleotide that finishes off the 5' end of ORF 5 (including the ribosomal-binding site) and contains new upstream restriction sites. Once these constructions are made, promoter-containing restriction fragments with ends compatible to the new restriction sites can be introduced, causing expression of the rib genes under the control of the new promoter. Both constitutive and growth-regulated B. subtilis promoters can be used, including but not limited to strong promoters from the lytic bacteriophage SPO1 genes, veg, amy (amylase), and apr (subtilisin).

In another aspect of the invention, rib operon DNA fragments which have transcriptional regulatory activity (e.g., promoters) can be used to regulate the expression of heterologous gene products.

Sequence information for such sequences can also be obtained from any known sequence data bank, e.g., the European Bioinformatics Institute (Hinxton Hall, Cambridge, GB). The DNA sequences can then be prepared on the basis of such sequence information using, e.g., the PCR method known in the state of the art and described, e.g., in the examples or other methods of molecular cloning known in the art.

Once such DNA sequences are available they can be integrated for further manipulation into suitable vectors known in the state of the art and described, e.g., in the examples. Preferred are such vectors for integration into the chromosome of the host which is preferably Bacillus and more preferably a *Bacillus subtilis* and subsequent amplification, if desired. Such vectors are described, e.g., in the Examples or known in the state of the art. Such vectors can further carry so called transcription elements, like enhancers and/or promoters, like the veg-promoter and/or natural or synthetic ribosomal binding sites and/or terminators, like, e.g., the cryT-terminator which is known in the state of the art. See, e.g., EP 370, US 378 and US 048 the pertient portions of which are herein reproduced. The desired host cells can then be transformed by such vectors by methods described, e.g., in the Examples or which are known in the state of the art and grown in a suitable medium. The riboflavin secreted into such medium can be isolated as described in the Examples or as known in the state of the art.

After the invention has been described in general hereinbefore, the following examples are intended to illustrate details of the invention, without thereby limiting it in any matter.

EXAMPLES

Example 1: Riboflavin-Overproducing *B. subtilis* Mutants

We describe in the examples herein the production of strains of *Bacillus subtilis* which overproduce riboflavin. In order to accomplish this, we used classical genetics, genetic engineering, and fermentation. Classical genetics with selection using purine and riboflavin analogs was used to deregulate the pathways for purine (riboflavin precursor) and riboflavin biosynthesis. Riboflavin production was increased further by cloning and engineering the genes of the riboflavin biosynthetic pathway (the rib operon), allowing for constitutive, high-level production of rate-limiting biosynthetic enzyme(s).

The biosynthesis of riboflavin in *B. subtilis* originates with GTP (FIG. 1). To obtain a host that overproduces riboflavin we used classical genetics to both increase the amount of GTP that the cell produces and to deregulate the riboflavin pathway. Purine overproduction in *B. subtilis* can be achieved by obtaining mutants resistant to purine analogs such as azaguanine and decoyinine, and other antagonists such as methionine sulfoxide (see e.g., Ishii and Shiio, *Agric. Biol. Chem.* 36(9):1511–1522, 1972; Matsui et al., *Agric. Biol. Chem.* 43(8):1739–1744, 1979). The riboflavin pathway can be deregulated by obtaining mutants resistant to the riboflavin analog roseoflavin (Matsui et al., *Agric. Biol. Chem.* 46(8):2003–2008, 1982). Roseoflavin-resistant strains were selected from several strains which had been previously mutagenized and which were resistant to several purine analogs. Described below are the methods used to produce a strain (RB50) which overproduces riboflavin.

8-Azaguanine-Resistant Mutants

*B. subtilis* is effectively killed by the purine analogue 8-azaguanine (Sigma Chemical Co., St. Louis, Mo.) at a concentration of 500 µg/ml, and resistant mutants appear spontaneously at a frequency of less than 1 in $10^8$. Ethyl methyl sulfonate (EMS; Sigma) at 30 µg/ml was used as a mutagen to increase the frequency of azaguanine-resistant ($Ag^r$) mutations. Mutagenesis was performed on cells from *B. subtilis* strain 168 by standard procedures (Miller, 1972, *Experiments in Molecular Genetics*, Cold Spring Harbor Laboratory, Cold Spring Harbor, N.Y.). After plating $4 \times 10^6$ mutagenized cells on minimal medium (Sloma et al., *J. Bact.* 170:5557, 1988) containing 500 µg/ml azaguanine and restreaking for single colonies, 35 $Ag^r$ colonies resulted. One mutant, RB11 ($Ag^r$-11), was used in the construction of RB50.

Decoyinine-Resistant Mutants

Decoyinine-resistant ($Dc^r$) mutations were obtained spontaneously at a frequency of 1 in $10^6$ or after EMS mutagenesis at 1 in $10^5$ by plating cells on minimal medium containing 100 µg/ml of decoyinine (Upjohn Co., Kalamazoo, Mich.). A $Dc^r$ mutant of RB11 was obtained by mutagenesis with EMS as described above. One $Dc^r$ colony, RB15 ($Ag^r$-11, $Dc^r$-15), was used in the construction of RB50.

Transfer of the Ag and Dc Mutations

These purine analog-resistant mutations were transferred to a different strain background in order to isolate them from any unwanted EMS-induced mutations and to verify that the $Ag^r$ and $Dc^r$ mutations were due to single loci. Since part of the "carbon flow" from inosine monophosphate (IMP), a riboflavin precursor, is also used for adenine nucleotide biosynthesis, a host strain was selected that was blocked in the adenosine monophosphate (AMP) pathway via the mutation pur-60, allowing more carbon material to "flow" from IMP to the guanine nucleotide precursors of riboflavin (FIG. 2). *B. subtilis* strain 1A382 (hisH2, trpC2, pur-60) was made competent (Sloma et al., *J. Bact.* 170:5557 (1988)) and transformed (by the method of Gryczan et al., *J. Bact.* 134:318 (1978)) with total DNA prepared from the $Ag^r/Dc^r$ mutant RB15. The Trp+ (tryptophan) revertant colonies were selected, with 3.3% (10/300) of those also being $Dc^r$ and 2.3% (7/300) $Ag^r$. This result was not unexpected since, due to "congression" (transformation of a second unlinked marker), a number of the Trp+ colonies should also be resistant to decoyinine or azaguanine.

One $Dc^r$ colony, RB36 (his H2, pur-60, $Dc^r$-15), one $Ag^r$ colony, RB40 (his H2, pur-60, $Ag^r$-11), and one $Dc^r/Ag^r$ colony (which was also found to be his+), RB39 (pur-60, $Ag^r$-11, $Dc^r$-15), were all selected for further study.

Methionine Sulfoxide-Resistant Mutants

Selection using high levels of methionine sulfoxide (MS; 10 mg/ml, Sigma) resulted in spontaneous mutants appearing at a sufficiently high frequency that mutagenesis with EMS was not necessary. The $Ag^r/Dc^r$ mutant, RB39, was streaked onto minimal medium containing 10 µg/ml MS. Resistant colonies were obtained and were restreaked for single resistant colonies. One strain, RB46 (pur-60, $Ag^r$-11, $Dc^r$-15, $MS^r$-46) was selected for further study.

Roseoflavin Resistant Mutants

Although many of these $Ag^r$, $Dc^r$ and $MS^r$ mutants were likely to be overproducing GTP, none of them produced levels of riboflavin detectable on plates. In order to deregulate the riboflavin biosynthetic pathway, conditions were determined to select for resistance to the riboflavin analog roseoflavin (Toronto Research Chemical). Maximum killing of cells occurred at 100 µg/ml of roseoflavin in minimal or complete medium; increasing the concentration did not result in any additional killing. Mutations to roseoflavin resistance ($RoF^r$) spontaneously occurred at a sufficiently high rate (approximately $5 \times 10^{-5}$) such that mutagenesis with EMS or other chemicals was not necessary.

Approximately 1000 $RoF^r$ colonies were obtained from each of the strains described above, 1A382, RB36, RB39, RB40 and RB46. $RoF^r$ mutants from all of these strains showed a low level of fluorescence on minimal media plates when exposed to long-wave UV light (366 nm), indicating some riboflavin production. One of the $RoF^r$ colonies obtained from RB46, RB46Y (pur-60, $Ag^r$-11, $Dc^r$-15, $MS^r$-46, $RoF^r$-46), when grown on minimal medium, produced 14 mg/l of riboflavin as determined by HPLC (described above).

Figure 5:
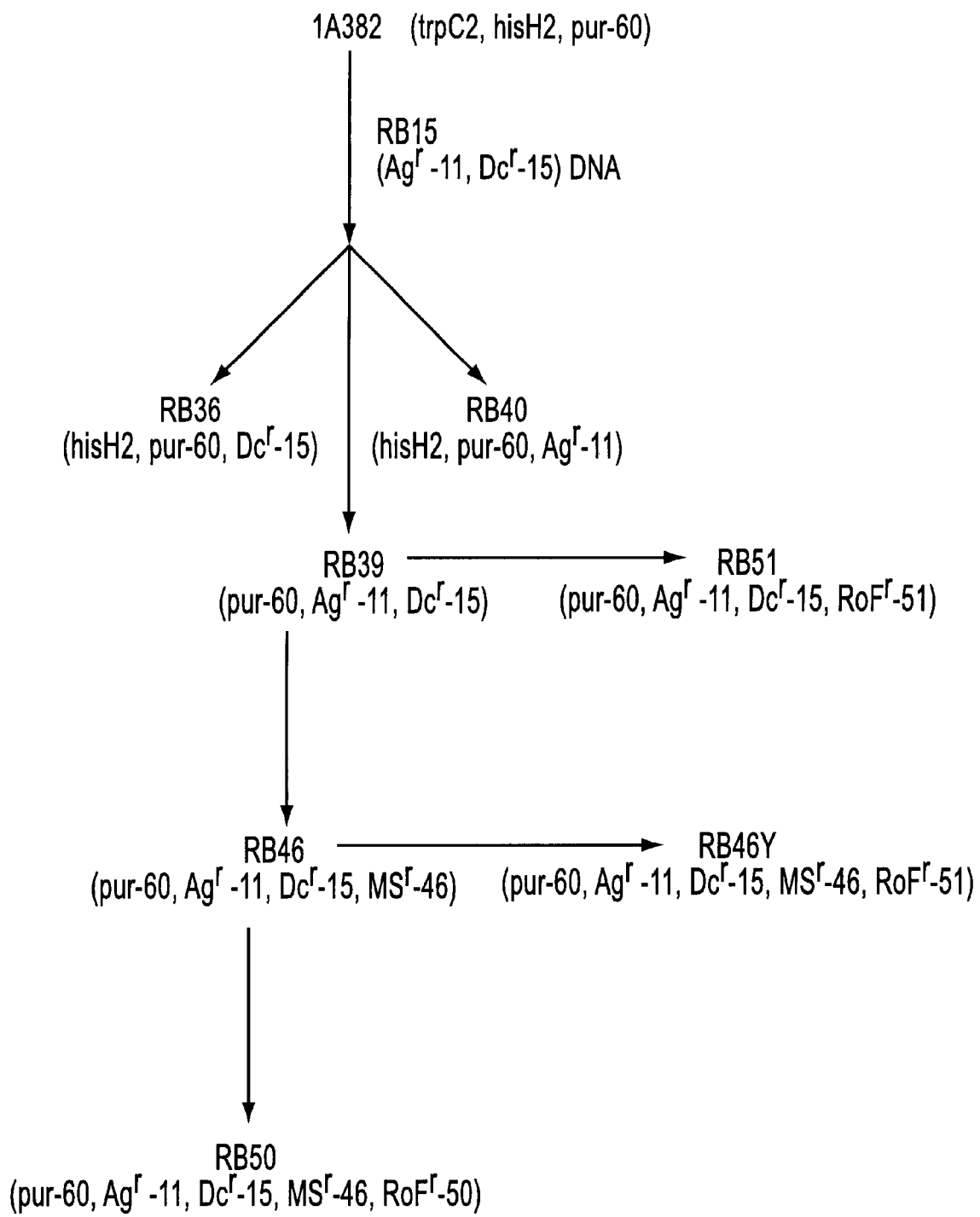
FIG. 5. Strain lineage of RB50. The lineage of the riboflavin overproducing strain of B. subtilis, RB50, is depicted. The various parent strains were exposed to riboflavin and purine analogs to select appropriate mutations.

Of all the strains treated, only RB39 and RB46 produced a significantly different phenotype when $RoF^r$ colonies were selected. Approximately 0.5% to 1.0% of the RoF$^r$ colonies of either RB39 or RB46 produced an intensely fluorescent, yellow colony. Of these colonies, RB51 (pur-60, Ag$^r$-11, Dc$^r$-15, RoF$^r$-51), arising from RB39, and RB50 (pur-60, Ag$^r$-11, Dc$^r$-15, MS$^r$-46, RoF$^r$-50), arising from RB46, produced a stable, fluorescent-yellow phenotype which correlated with a higher level of riboflavin production, as determined by HPLC. When grown in minimal medium, both RB50 and RB51 produced higher levels of riboflavin in their supernatants than the other RoF$^r$ strains, about 40 mg/l and 30 mg/l, respectively. The lineage of RB50 is depicted in FIG. 5.

Because intensely fluorescent (and thus riboflavin overproducing) colonies could be obtained in non-MS$^r$ strains such as RB51, it appeared that this mutation in general might not be contributing significantly to the higher production phenotype. Both of the other mutations, Ag$^r$ and Dc$^r$ (Ag$^r$-11 and Dc$^r$-15 in RB39), appear to be necessary to produce high levels of riboflavin since no intensely fluorescent RoF$^r$ colonies could be found in strains containing only the Ag$^r$-11 (from RB40) or Dc$^r$-15 (from RB36) mutation alone.

guaC Mutations

Figure 2:
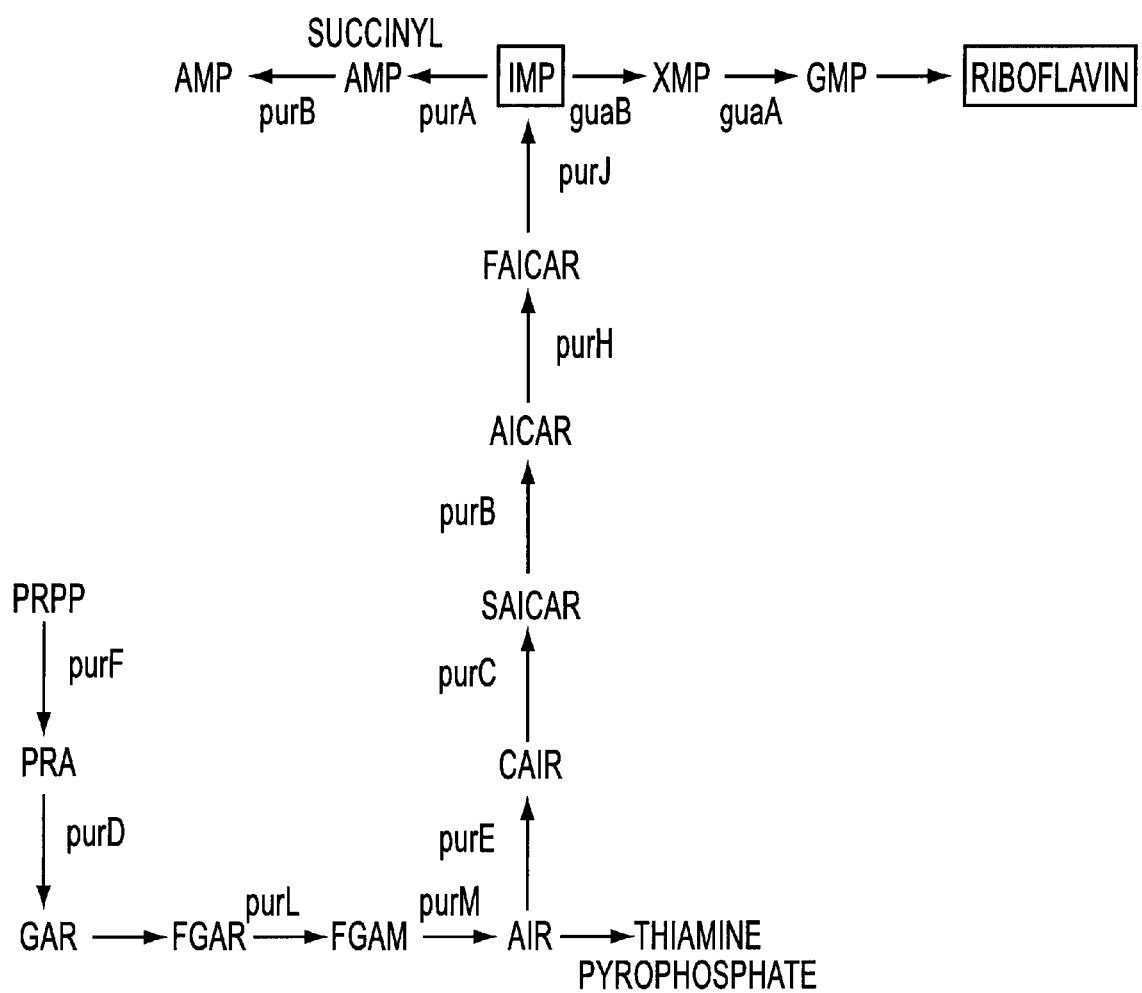
FIG. 2. Schematic representation of purine biosynthesis. The purine biosynthetic pathway, including the portion responsible for riboflavin biosynthesis, is depicted. The individual enzymes of the pathway are identified by their gene symbols (E. coli nomenclature). Abbreviations are as follows: PRPP, phosphoribosylpyrophosphate; GAR, glycinamide ribonucleotide; pur, GAR formyltransferase; PRA, phosphoribosylamine; purA, adenylosuccinate synthetase; purB, adenylosuccinate synthetase; FGAR, forinylglycinamide ribonucleotide; SAICAR, aminoimidazolesuccinocarboxamide ribonucleotide; purC, SAICAR synthetase; FGAM, formylglycinamidine ribonucleotide; purD, GAR synthetase; AIR, aminoimidazole ribonucleotide; purE, AIR carboxylase; CAIR, carboxyaminoimidazole ribonucleotide; purF, PRPP amidotransferase; AICAR, aminoimidazolecarboxamide ribonucleotide; purH, AICAR formyltransferase; purJ, inosine monophosphate (MIMP) cyclohydrolase; FAICAR, formamidoimidazolecarboxamide ribonucleotide; purL, FGAR amidotransferase: guaA, guanosine monophosphate (GMP) synthetase; purM, AIR synthetase; guaB, IMP dehydrogenase.

Another possibly important mutation for achieving overproduction of GTP, and thus riboflavin, is guaC3, which prevents the conversion of GMP back into IMP (see FIG. 2). To construct a strain containing guaC3 that overproduces riboflavin, competent B. subtilis strain 62121 cells (guaC3, trpC2, metC7) (Endo et al., J. Bact. 15: 169, 1983) were transformed with RB50 DNA and selected for Dc$^r$ on plates containing 100 μg/ml of decoyinine. Thousands of Dc$^r$ colonies resulted. Of 200 colonies which were patched onto Dc$^r$ plates, one was found that exhibited the riboflavin overproduction phenotype (based on UV fluorescence), and was RoF$^r$. This colony was designated RB52 (guaC3, trpC2, metC7, Dc$^r$-15, RoF$^r$-50) and was reserved for subsequent study.

Other Analog-Resistant Mutants

Finally, because mutants resistant to several additional purine analogs also have been reported to be altered in purine metabolism, such mutations were assayed in order to investigate their effect on riboflavin-overproducing strains. It was determined that 500 g/ml of 8-azaxanthine, 1 mg/ml of 6-thioguanine, or 2 mg/ml of sulfaguanidine (Sigma) effectively kills wild-type B. subtilis. The azaguanine-resistant, riboflavin-overproducing strains RB50::[pRF8]$_{90}$ and RB53::[pRF8]$_{90}$ (see below) were found to be already resistant to azaxanthine. Although separate azaguanine- and azaxanthine-resistant mutations with different properties have been described previously, in this case the Ag$^r$-11 and Ag$^r$-53 mutations appear to also convey azaxanthine resistance.

HPLC Analysis of riboflavin in crude supernatants of B. subtilis

Accumulation of riboflavin in B. subtilis cultures was quantitated by reverse-phase HPLC. Riboflavin standards (Sigma Chemical Co., St. Louis, Mo.) or cell-free supernatants from strains to be tested were fractionated over a 4.6 mm×250 mm Vydac C$_{18}$ column equilibrated with 1% ammonium acetate (pH 6.0). At injection, the column was developed with a linear gradient of methanol and monitored for riboflavin at 254 nm. Authentic riboflavin (i.e. riboflavin "standard") elutes at the mid-point of the gradient.

Example 2: Cloning B. subtilis Rib Operon

Our general strategy to isolate a restriction fragment containing the rib operon was to screen a "mini" E. coli plasmid library of B. subtilis DNA by hybridization with a synthetic oligonucleotide probe, the DNA sequence of which was partially derived from the published amino acid sequence for the β subunit of riboflavin synthase (Ludwig et al., J. Biol. Chem. 262:1016, 1987). A summary of the protocol is presented in FIG. 6.

A synthetic, 54-base "guess-a-mer" oligonucleotide probe was used for this screening based on amino acids 84–102 of the 240 amino acid riboflavin synthase protein, sequenced by Ludwig et al. (J. Biol. Chem. 262:1016–1021, 1987). The third nucleotide of each codon in the probe was chosen according to estimates made of the most frequent codon usage of B. subtilis, based upon, for example, some of the sequences available in GenBank® (Los Alamos Nat. Lab, Los Alamos, N. Mex.). The probe consisted of the following sequence:
5'-GGAGCTACAACACATTATGATTATGTTTGCAATGA AGCTGCTAAAGGAATTGCF-3' (SEQ ID NO. 230). To test the specificity of the probe, the $^{32}$P-labelled 54-mer DNA was hybridized to nylon filters containing EcoRI-digested chromosomal DNA (Southern, J. Mol. Biol. 98:503, 1975) isolated from wild-type and the mutant B. subtilis strains. The probe strongly hybridized to a single 9–10 kb fragment of EcoRI-digested B. subtilis (rib$^+$ met$^-$) DNA, which is in good agreement with the predicted size of the rib-containing fragment (Osina et al., FEBS. Lett. 196:75, 1986). A labelled fragment of the identical size was detected when the probe was hybridized to two mutant strains, RB46 (pur-60, Ag$^r$-11, Dc$^r$-15, MS$^r$-46) and RB50 (pur-60, Ag$^r$-11, Dc$^r$-15, MS$^r$-46, RoF$^r$-50), the latter being a riboflavin overproducer. These hybridization experiments were repeated using HindHIII-cut chromosomal DNA, which resulted in the probe identifying a smaller, single fragment of approximately 1.8 kb; this latter result was useful in determining the general location of the rib biosynthetic operon within the cloned DNA.

Isolation of Plasmids pRF1, pRF2 and pRF3, Containing Wild-type Rib Biosynthetic Genes A "mini" gene library of 9–11 kb EcoRI fragments from B. subtilis strain 168 (rib$^+$) DNA was prepared using pRK290, a low-copy number vector derived from the Pseudomonas replicon RK2 (Ditta et al., Plasmid 3:149, 1985). EcoRI fragments (size 9–11 kb) of B. subtilis (rib$^+$ met$^-$) DNA were isolated by sucrose (10–40%) rate-zonal centrifugation. A four-fold excess of these fragments (0.22 μg) was ligated to EcoRI-cut pRK290 (0.26 μg), that had been dephosphorylated with calf intestinal alkaline phosphatase (CIAP), at a total DNA concentration of 10 μg/ml. Approximately 10 ng of ligated DNA was transformed into E. coli DH5 (F-, endA1, hsdR11 [r$_k$-, m$_k$+], supE$_{44}$, thi-1, λ-, recA1, gyrA96, relA1), resulting in tetracycline-resistant (Tc$^r$) colonies at a frequency of 7.7×10$^4$/μg of DNA. To determine the fraction of transformants containing insert DNA of 9–11 kb, plasmid mini-lysates were prepared from several Tc$^r$ transformants, and their DNA was analyzed by restriction enzyme digestion. About 40% of the Tc$^r$ transformants were found to contain single EcoRI-generated inserts of 9–11 kb.

Approximately 1140 of the Tc$^r$ colonies were screened with the $^{32}$P-labelled 54-mer probe specific for the riboflavin synthase gene. One colony gave a positive signal. Plasmid DNA, designated pRF1, was isolated from this clone and tested for Rib$^+$-marker rescue activity by transforming the DNA into B. subtilis 1A210 that contains the riboflavin-deficient mutation rib-2, and selecting for Rib$^+$ prototrophic colonies. pRF1 transformed 1A210 to Rib$^+$ prototrophy at a high frequency. Plasmid DNA from a randomly chosen Tc$^r$ transformant failed to rescue this marker.

Restriction enzyme analysis revealed that pRF1 actually contained two EcoRI-fragment inserts, of 10 kb and 11 kb. To determine which fragment contained the rib operon, EcoRI-digested pRF1 was probed with the $^{32}$P-labelled, 54-mer riboflavin synthase probe. The results indicated that only the smaller, 10 kb fragment cross-reacted with the probe. Moreover, when the 10 kb EcoRI fragment was recloned into the EcoRI site of pBR322, recombinant plasmids pRF2 and pRF3 resulted, representing the two possible orientations of insertion. Both plasmids were found to rescue the rib-2 mutation of *B. subtilis* 1A210 to prototrophy at a high frequency.

Isolation of Plamsids pRF6 and pRF7
Containing Rib Biosynthetic Genes
From RoF$^r$-*B. subtilis* Strain RB50

RB50 is one of the RoF$^r$ mutants of *B. subtilis*, produced as described above, that is deregulated for riboflavin biosynthesis. It has been reported that approximately 80% of RoF$^r$ mutations reside within the rib operon at the rib locus (Stepanov, et al., *Genetika* (USSR) 13:490, 1977). Like the wild-type rib operon, rib genes in RB50 were also contained on a 9–10 kb EcoRI fragment; thus this fragment was cloned using the protocol outlined in FIG. 6, with pBR322 used as the cloning vector. Size-selected 9–11 kb EcoRI fragments (0.1 μg) from RB50 were prepared as before and ligated to a two-fold excess of ends of EcoRI-cut, dephosphorylated pBR322 DNA (0.34 μg) at a total DNA concentration of 22 μg/ml. Approximately 9 ng of ligated DNA was transformed into *E. coli* DH5, resulting in ampicillin-resistant (Ap$^r$) colonies at a frequency of 3.5×10$^5$/μg of DNA.

Restriction enzyme analysis of plasmid DNA isolated from a sampling of 12 Ap$^r$ colonies revealed that 50% contained plasmids with 9–11 kb EcoRI inserts. Approximately 1140 Ap$^r$ colonies were screened with the $^{32}$P-labelled 54-mer probe specific for the riboflavin synthase gene by colony hybridization. Six colonies gave positive signals. Plasmids pRF6 and pRF7, isolated from two of these six colonies, were identified by restriction enzyme analysis as containing inserts with the same orientation as pRF2 and pRF3, respectively. In addition, both plasmids were able to marker-rescue the rib-2 mutation at high frequencies.

Example 3: Introducing Rib$^+$ DNA Into *B. subtilis*

Figure 6:
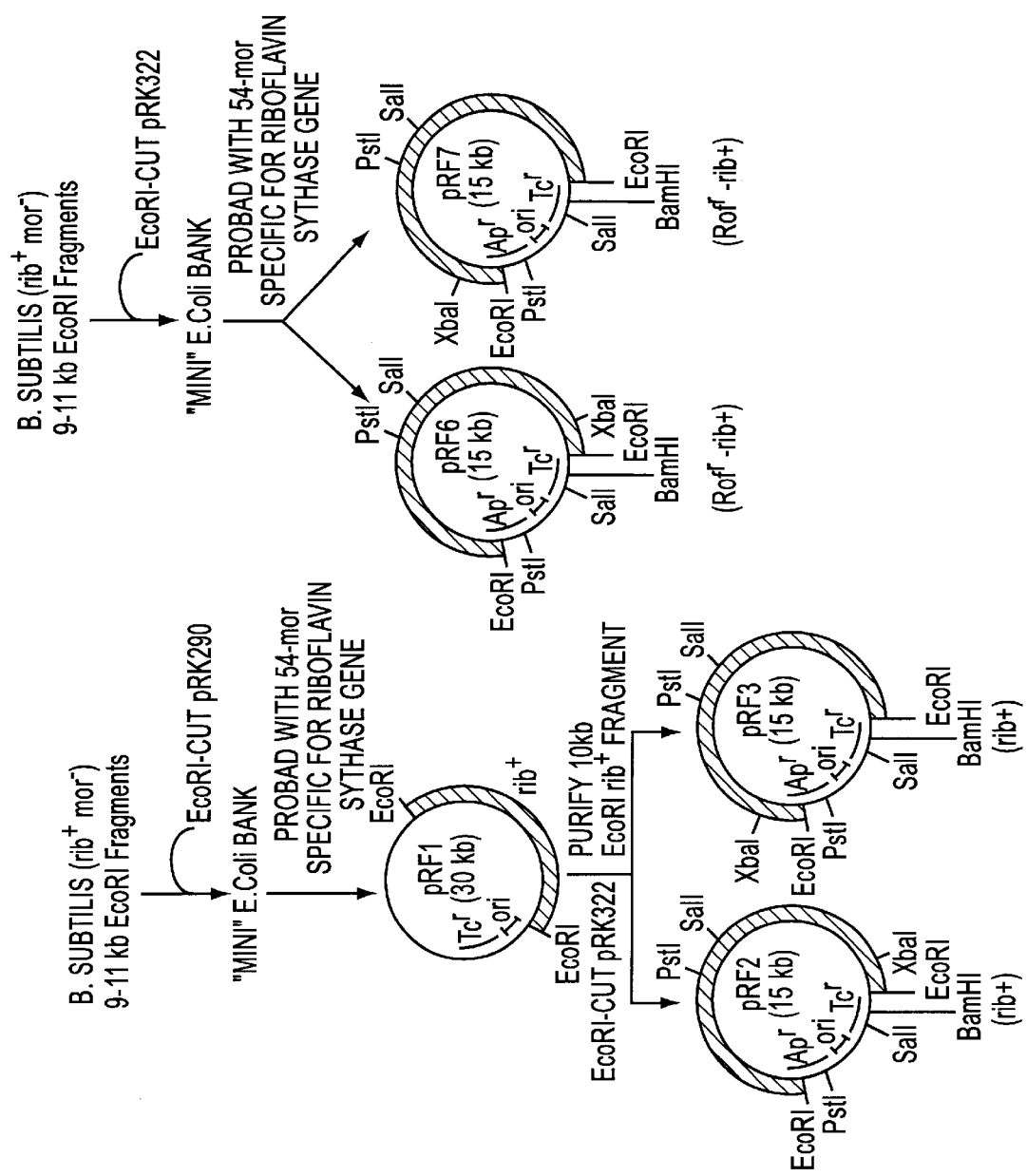
FIG. 6. Origins of rib+ recombinant plasmids. A schematic diagram of the production of the rib operon-containing recombinant plasmids pRF1, pRF2, pRF3, pRF6 and pRF7 is presented. A library of size-selected, 9–11 kb fragments of B. subtilis DNA was used to produce a gene library in E. coli plasmid vectors. Clones were selected by hybridization to the 54-mer probe specific for the β subunit of the riboflavin synthase gene.

As described supra, the rib operon from both a wild-type strain and a RoF$^r$ mutant of *B. subtilis* were cloned as identical 10 kb EcoRI fragments into the EcoRI site of the *E. coli* replicon pBR322; the derivation of these recombinant plasmids is schematically diagrammed in FIG. 6. To introduce the 10 kb EcoRI fragment containing the rib operon into *B. subtilis* in multiple copies, and thus further increase riboflavin production, we constructed a plasmid vector which would allow integration into the *B. subtilis* chromosome. The integrated DNA was amplified by selecting colonies that would grow at high drug concentrations of chloramphenicol.

Construction of and Transformation with
Integrational rib Plasmids pRF4 and pRF8

To construct the integrational vector, the drug-resistance gene chloramphenicol acetyltransferase (cat), which is selectable in *B. subtilis*, was introduced into pRF2 and pRF6, the pBR322 vectors with the 10 kb fragment from wild-type or RoF$^r$ *B. subtilis* strains, respectively. The plasmids pRF2 and pRF6 were digested with , which cuts the plasmids uniquely within the pBR322 sequence, and dephosphorylated with CIAP. The cleaved DNA was ligated to a 1.3 kb BamHI fragment containing the cat gene (Youngman et al., *Plasmid* 12: 1–9, 1984), and the ligated DNAs then transformed into *E. coli* DH5 cells (Hanahand, *J. Mol. Biol.* 166: 557, 1983). Approximately 80–90% of the Ap$^r$ transformants were chloramphenicol resistant (Cm$^r$); restriction analysis of the isolated plasmids (Maniatis et al.) confirmed that plasmid DNA from the Cm$^r$ colonies contained the 1.3 kb fragment. The plasmid containing the wild-type riboflavin fragment and the cat gene was designated pRF4; the plasmid containing the cloned riboflavin fragment from the RoF$^r$ strain was called pRF8. (Since the RoF$^r$ mutation was subsequently shown to be outside the rib operon, these plasmids are presumably identical).

The plasmids pRF4 and pRF8 were transformed into four different *B. subtilis* strains: the riboflavin overproducer RB50 (Ag$^r$-11, Dc$^r$-15, MS$^r$-46, RoF$^r$-50), the RB50 parent RB46 (Ag$^r$-1, Dc$^r$-15, MS$^r$-46), the RB50 parent 1A382, and IS75, a common laboratory strain. Competent IS75 and 1A382 cells were transformed with pRF4 or pRF8; these same plasmids were introduced into RB46 and RB50 by transformation of protoplasts (Chang and Cohen, *Mol. Gen. Genet* 168:111–115, 1979). The pRF4 or pRF8 DNA integrated into each of these four strains was amplified by selecting for colonies that grew at higher chloramnphenicol concentrations. In each strain, we were able to obtain colonies that grew in up to 60 μg/ml of chloramphenicol.

Figure 7:
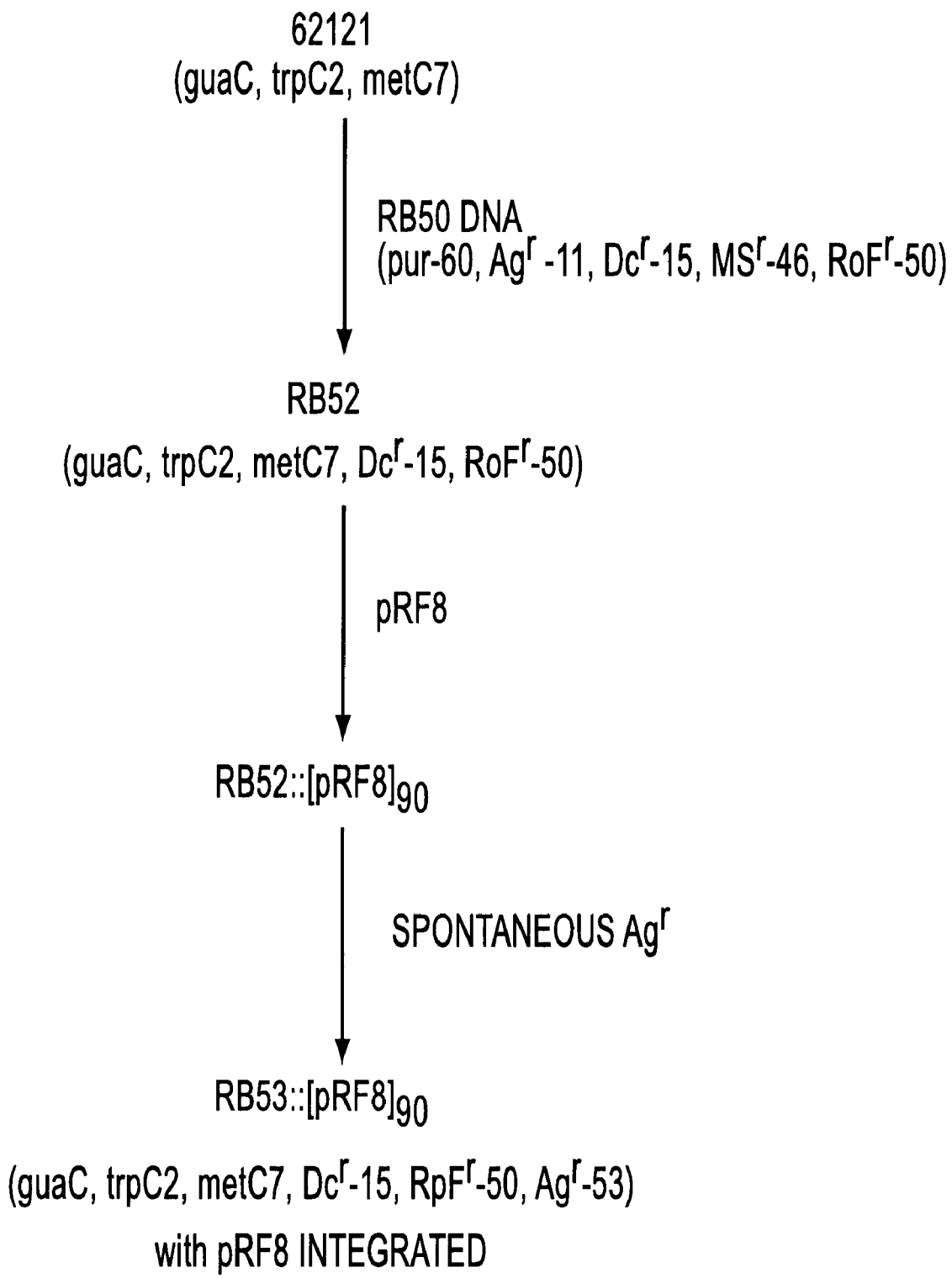
FIG. 7. The strain lineage of B. subtilis RB53::[pRF8]$_{90}$. Plasmid pRF8 was integrated into the chromosome of the intermediate strain RB52 and amplified; the resulting strain was exposed to the purine analog azaguanine.

In addition, RB52 (guaC3, trpC2, metC7 Dc$^r$-15, RoF$^r$-50), produced by transforming the guaC3 *B. subtilis* strain 62121 with DNA from RB50, was made competent and transformed with pRF8. The integrated plasmid in one of the many Cm$^r$ colonies that resulted was amplified using 90 μg/ml of chloramphenicol. The resulting cells, RB52::[pRF8]$_{90}$, were grown to mid-log phase and plated on minimal media containing 500 μg/ml azaguanine. Approximately 20 Ag$^r$ colonies resulted. One such colony seemed to produce a more intense fluorescence. The lineage of this strain, RB53::[pRF8]$_{90}$, is given in FIG. 7.

Example 4: Riboflavin Overproduction by Strains Containing pRF4 or pRF8

RB50 containing pRF4 or pRF8 displayed the riboflavin overproduction phenotype (yellow and UV-fluorescent colonies). Amplification of the rib$^+$ DNA in a wild-type strain or the parent strains of RB50 did not yield yellow or UV-fluorescent colonies, a finding that indicates that the RoF$^r$ mutation (which deregulates the biosynthesis of riboflavin) is required for chromosomal amplification of wild-type DNA to cause riboflavin overproduction. A series of shake flask fermentations were performed in 25 ml of riboflavin minimal medium (RMM, in Table I) in a 300 ml baffled flask (Bellco) to measure the production of riboflavin from RB50 that contained the integrated and amplified rib operon.

TABLE I

| COMPOSITION OF MEDIA | |
|---|---|
| RMM | g/l |
| Sodium glutamate | 2.0 |
| Casamino acids (Difco) | 0.2 |
| Yeast extract (Difco) | 0.2 |
| KH$_2$PO$_4$ | 6.0 |
| K$_2$HPO$_4$ | 14.0 |
| (NH$_4$)$_2$SO$_4$ | 2.0 |
| Sodium citrate | 1.0 |
| MgSO$_4$.7H$_2$O | 0.2 |

TABLE I-continued

COMPOSITION OF MEDIA

| RMM | g/l |
|---|---|
| Adenosine | 0.05 |
| (adjusted to pH 7.0 and autoclaved) | |
| Maltose | 15.0 |
| (added as sterile 20% solution after autoclaving) | |

The fermentations were run with strrrns RB46, RB50 and RB50 containing pRF4 amplified by selection for resistance to 30 μg/ml of chloramphenicol (RB50::[pRF4]$_{30}$) and 90 μg/ml of chloramphenicol (RB50::[pRF4]$_{90}$). At 24 and 48 hours, supernatant samples were removed and measured for riboflavin content by reverse-phase HPLC.

As shown in Table II, RB50::[pRF4]$_{30}$ produced 0.3 g/l of riboflavin, and RB50::[pRF4]$_{90}$ produced 0.7 g/l of riboflavin, in 48 hours, which is significandy more than that produced by the strains without rib amplification, such as RB46 and RB50.

TABLE II

QUANTITATIVE ANALYSIS OF RIBOFLAVIN-
CONTAINING SUPERNATANTS FROM *B. SUBTILIS*

| Strain | Culture Time (hours) | Riboflavin* (g/l) |
|---|---|---|
| RB46 | 24 | 0.009 |
| RB50 | 24 | 0.02 |
| RB50::[pRF4]$_{30}$ | 24 | 0.1 |
| RB50::[pRF4]$_{90}$ | 24 | 0.4 |
| RB46 | 48 | 0.007 |
| RB50 | 48 | 0.05 |
| RB50::[pRF4]$_{30}$ | 48 | 0.3 |
| RB50::[pRF4]$_{90}$ | 48 | 0.7 |

*Riboflavin was measured using an HPLC assay.

The dramatic increase in riboflavin production resulting from amplification of rib genes in the deregulated host argues that information encoded by the cloned DNA is rate-limiting for riboflavin biosynthesis.

Example 5: Mapping the RoF$^r$-50 Mutation

The RoF$^r$-50 mutation in RB50 appeared to be critical to the riboflavin-overproduction phenotppe. To identify and possibly move the mutation into different strain backgrounds it was necessary to map the location of the RoF$^r$-50 mutation on the *B. subtilis* chromosome. Since pRF4 and pRF8 gave very similar levels of riboflavin production in all strain backgrounds, it seemed unlikely that the RoF$^r$-50 mutation was located on the cloned 10 kb EcoRI, rib-containing fragment. More likely, the RoF$^r$-50 mutation is an unlinked repressor-type mutation, possibly in ribC, a repressor mutation which has been reported to map in the lys-aroD region of the *B. subtilis* chromosome (Chernk et al., *Genetika* (USSR) 15:1569, 1979). To determine whether the RoF$^r$-50 mutation was linked or unlinked to the riboflavin operon, competent *B. subtilis* 1A210 (rib-2) cells were transformed with RB50 DNA, selecting for rib$^+$. Thousands of rib$^+$ colonies resulted, and 200 colonies were patched onto tryptose blood agar base containing 100 g/ml of roseoflavin. No RoF$^r$ colonies resulted, and none of the colonies exhibited the riboflavin overproduction phenotype, confirming that the RoF$^r$-50 mutation is not located in the rib operon.

Example 6: Locating rib$^+$ Biosynthetic Genes Using CAT Insertional Mutagenesis FIG. 4 contains a restriction map of the rib-containing 10 kb EcoRI fragment of pRF2, prepared according to standard procedures. Restriction enzyme sites for XbaI, BglII, SstI, HpaI and NcoI are unique to the insert DNA, whereas SalI and PstI cut once in the insert and once in the vector, the insert does not contain any BamHI, XhoI or NheI restriction sites. Restriction enzyme HindIII cleaves the insert at multiple sites; the 54-mer probe specific for the riboflavin synthase gene hybridized to an approximately 1.8 kb HindIII fragment, suggesting that the rib operon must also reside in the general area surrounding the SalI and left-most BglII (BglII$_L$) sites.

In general, to determine the boundaries of the rib operon, small cat-containing restriction fragments were used to construct insertions and deletions in the rib$^+$-cloned DNA fragment of pRF2.

*E. coli* plasmid pEcc1 served as the primary source of restriction fragments bearing a cat gene which confers chloramphenicol-resistance in both *E. coli* and *B. subtilis*. This plasmid, a derivative of pMI1101 (Youngman et al., Plasmid 12:1–9, 1984) in which a non-essential region of the plasmid was removed by standard recombinant DNA techniques, contains a 1.3 kb cat-containing fragment flanked by the "polylinkers" of M13mp7, and therefore is capable of generating cat cassettes with either SmaI, EcoRI, SalI, or BamHI ends. To generate SstI or XbaI-ended fragments containing the cat gene, the 1.3 kb cat-containing BamHI fragments of pEcc1 was isolated, the ends modified with HindIII linkers, and the modified fragment cloned into the HindIII site within the polylinker region of pIC10R, generating plasmid pEcc4.

Integrative plasmid derivatives were first constructed in *E. coli* and then transferred to the rib chromosomal locus of *B. subtilis* by DNA transformation. This was done by linearizing the plasmid by a restriction enzyme cut outside the cloned DNA insert, transforming competent *B. subtilis* strain 1A382 or PY79 (SPβ$^c$, SPβ$^c$ rib$^+$) cells with this cut DNA, and selecting for Cm$^r$. Because the pBR322 replicon is unable to replicate in *B. subtilis*, and the cat gene is bounded on both sides by sequences homologous to the rib$^+$ locus, the cat-containing insertion or deletion can only be inserted into the chromosome by a double-crossover recombination event to yield Cm$^r$ transformants. To determine whether the insertion or deletion inactivated riboflavin synthesis, Cm$^r$ colonies were assessed for growth on minimal medium agar plates with or without the presence of riboflavin (Rib phenotype).

Figure 8:
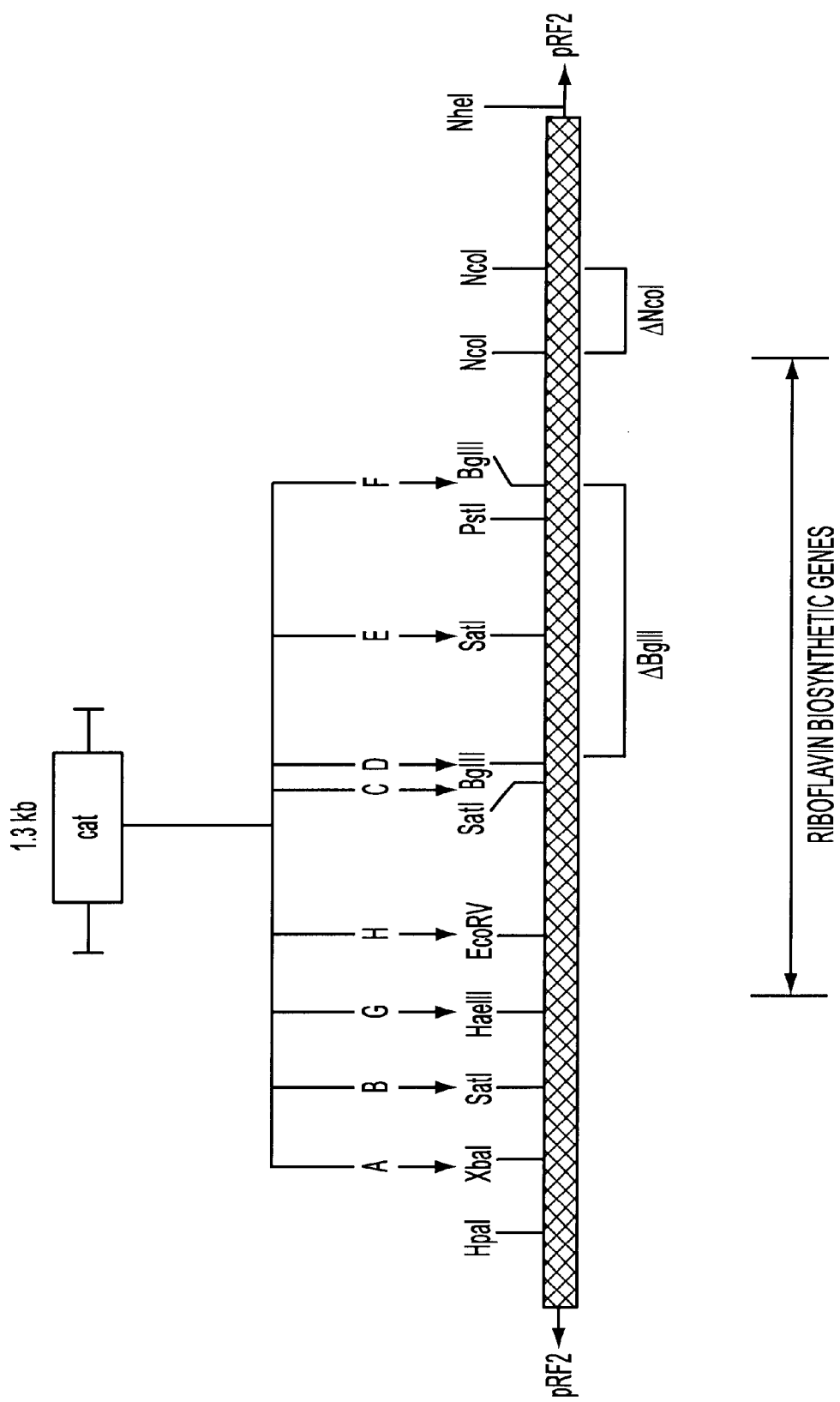
FIG. 8. Identification of regions essential for riboflavin biosynthesis using insertions and deletions. A diagram is presented of the 10 kb cloned EcoRI DNA fragment with the regions essential for riboflavin biosynthesis indicated. Insertions and deletions at the indicated restriction sites enabled the localization of the rib operon. Not all restriction sites are indicated.

As diagrammed in FIG. 8, cat-containing restriction fragments were inserted by ligation into the individual restriction sites for XbaI, SstI, SalI and BglII of pRF2, inserted between the pair of BglII or NcoI sites (generating deletions removing either a 2.0 kb BglII fragment or a 0.8 kb NcoI fragment) or inserted into single HaeIII and EcoRV sites of the approximately 1.8 kb HindIII fragment that hybridized to the rib-specific DNA probe, according to standard techniques. The results are shown in Table III.

TABLE III

CHARACTERIZATION OF INSERTION AND
DELETION DERIVATIVES OF rib$^+$ DNA

| Insertion derivative[a] | *B. subtilis*[b] Riboflavin Phenotype |
|---|---|
| A(XbaI) | |
| r | + |
| l | ND |

TABLE III-continued

CHARACTERIZATION OF INSERTION AND DELETION DERIVATIVES OF rib+ DNA

| Insertion derivative[a] | B. subtilis[b] Riboflavin Phenotype |
|---|---|
| B(SstI$_L$) | |
| r | + |
| l | ND |
| C(SstI$_R$) | |
| r | — |
| l | — |
| D(BglII$_L$) | |
| r | — |
| l | — |
| E(SalI) | |
| r | — |
| l | — |
| F(BglII$_R$) | |
| r | — |
| l | — |
| G(HaeIII) | |
| r | ND |
| l | + |
| H(EcoRV) | |
| r | + |
| l | ND |
| Deletion derivative | |
| BgI | |
| r | — |
| l | — |
| Nco | |
| r | + |
| l | + |

[a] "r" (right) and "l" (left) identify the transcriptional orientation of the inserted cat gene relative to the restriction map in FIG. 8.
[b] B. subtilis strain 1A382 (rib+, trpC2, pur-60, hisH2) or PY79 (SP β$^c$, rib+)

As summarized in FIG. 8 and Table III, insertions into the SalI, either BglII, or the "right most" SstI (SstI$_R$) sites, or deletion of the 2.0 kb BglII fragment, all generated Cm$^r$ colonies that could not produce riboflavin (Rib⁻), indicating that the rib operon was centrally located within the cloned DNA. Significantly, removal of the 0.8 kb NcoI fragment apparently had no effect on riboflavin production (Rib+), suggesting that one end of the rib gene cluster was located to the left of the "left most" NcoI (NcoI$_L$) site. The other end of the rib operon was initially determined to map within the approximately 1.8 kb HindIII fragment because the two insertions at sites within the fragment, EcoRV and HaeIII, as well as sites distal to the fragment, XbaI and SstI$_L$, all generated Cm$^r$ colonies that produced riboflavin.

Example 7: Nucleotide Sequence of the Rib Operon

Based on the cat-insertional mutagenesis of the cloned 10 kb DNA fragment, the entire rib operon was localized within a 6.0 kb region bounded by the SstI$_L$ and NcoI$_L$ sites.

This 6.0 kb region of pRF2 containing the rib operon and flanking regions was sequenced by the dideoxy method of Sanger et al. (*Proc. Natl. Acad. Sci. USA* 74:5463, 1977). Briefly, M13 clones for sequencing were prepared either by subcloning specific restriction fragments into M13, by using the exonuclease activity of T4 DNA polymerase to generate a series of overlapping deletions (Dale et al., *Plasmid* 13:31, 1985), or by "shot-gun" cloning random fragments, from sonicated restriction fragments, into M13. In some cases, the nucleotide sequence across a restriction site juncture of adjacent fragments was also determined by primer extension sequencing. Approximately 5500 bp were sequenced on both strands and analyzed for sequences resembling typical open reading frames with gram positive-bacteria ribosome binding sites, gram-positive promoters and rho-independent transcription termination sites.

Analysis revealed six complete, non-overlapping open reading frames (FIG. 3): ORF 2 (124 amino acids), the gene coding for the β subunit of riboflavin synthase (154 amino acids), ORF 3 (398 amino acids), ORF 4 (215 amino acids), ORF 5 (361 amino acids) and ORF 6 (105 amino acids). Each ORF was preceded by a strong Bacillus ribosome binding site (RBS) with calculated thermostability ranging from ΔG=−16 to −22 kcal/mol, and all of them were oriented in the same transcriptional direction. In addition, within the coding region of ORF 5, a second RBS site and ATG start codon were identified, potentially encoding a smaller protein of 248 amino acids. However, based on S-30 in vitro coupled transcription/translation reactions (see below), ORF 5 appears to encode only a 361 amino acid protein. Finally, part of another coding region, ORF 1, encoding the last 170 amino acids of a protein and oriented in the opposite direction, was also identified.

Based on the following observations, riboflavin biosynthesis in Bacillus is controlled by a single operon containing 5 genes: the β riboflavin synthase gene, ORF 2, ORF 3, ORF 4, and ORF 5, of which at least four, the β-riboflavin synthase gene, ORF 3, ORF 4 and ORF 5, unambiguously encode biosynthetic enzymes, with the remaining one, ORF 2, possibly encoding a biosynthetic enzyme.

1. ORF 3, ORF 4 and ORF 5 overlap restriction enzyme sites where insertion cat-containing restriction fragments caused inactivation of riboflavin production in *B. subtilis* (FIGS. 4 and 8).
2. ORF 1 overlaps a restriction enzyme site(s) where insertion of cat-containing restriction fragments did not cause inactivation of riboflavin production in a rib+ *B. subtilis* strain (Table III and FIG. 8), nor did it cause reduction of riboflavin production in the deregulated, RoF$^r$ *B. subtilis* strain RB52.
3. ORF 2 also overlaps a restriction enzyme site, EcoRV, where insertion of cat-containing restriction fragments did not cause inactivation of riboflavin production in a rib+ *B. subtilis* strain (Table III and FIG. 8). However, such an insertion did cause a detectable reduction of riboflavin production in the deregulated, RoF$^r$ *B. subtilis* strain RB52, indicating that the mutated ORF 2 gene product was partially inactive for riboflavin production. The results suggest that ORF 2 does encode a rib-specific enzyme.
4. Two DNA sequences capable of forming stem-loop structures indicative of rho-independent transcriptional termination sites were identified within the intercistronic gaps between ORF 1 and ORF 2 and between ORF 5 and ORF 6 (FIGS. 4 and 9). Removal of structures between ORF5 and ORF 6 enhances expression of riboflavin. The structures impart riboflavin sensitivity to lacZ-fusion constructs; thus, they can be used to impart such sensitivity to any other gene to which they are fused at the 5' end upstream of the promoter.

5. A DNA sequence, TTGCGT-(17 bp)-TATAAT, (SEQ ID NO. 231) resembling the promoter recognized by the $\sigma^A$ (vegetative form) of *B. subtilis* RNA polymerase was identified approximately 290 bp upsteam from ORF 5, oriented in the same transcriptional direction as ORF 5 (FIG. 4). A transcriptional fusion of this promoter ($P_1$, on a 1.1 kb BglII-NcoI restriction fragment) to a promoterless *E. coli* lacZ gene ($P_1$-lacZ) displayed riboflavin-regulated expression of β-galactosidase activity in a rib$^+$, *B. subtilis* strain (62121) and high-level, constitive (unregulated) expression of β-galactosidase activity in a rib$^+$, RoF$^r$ *B. subtilis* strain (RB52) only when the promoter was oriented in the same transcriptional direction as the gene, as shown in Table IV. Primer extension analysis was used to confirm the start site. Transcriptional and Northern analyses were used to show a polycistronic RNA of 4.2 kb encompasses the entire rib operon.

TABLE IV

RIBOFLAVIN-REGULATED EXPRESSION OF $P_1$-LacZ TRANSCRIPTIONAL FUSIONS

| Strain (integrated plasmid) | β-Galactosidase Specific Activity (Miller Units) | |
|---|---|---|
| | + Riboflavin (2 μg/ml) | − Riboflavin |
| *B. subtilis* 62121 ($P_1$-lacZ$^a$) | 1.3 | 4.2 |
| *B. subtilis* RB52 ($P_1$-lacZ$^a$) | 31 | 38 |
| *B. subtilis* 62121 ($P_1$-lacZ$^b$) | <0.1 | <0.1 |
| *B. subtilis* 62121 | <0.1 | <0.1 |

$^a P_1$ and lacZ oriented in the same direction
$^b P_1$ and lacZ oriented in opposite directions Based on these results, this $\sigma^A$ promoter, $P_1$, is a primary promoter for transcription of ORF 5, ORF 4, ORF 3, β-riboflavin synthase gene and ORF 2.

6. A second DNA sequence, TTGAAG-(17 bp)-TACTAT, (SEQ ID NO. 232) resembling a promoter recognized by the $\sigma^A$ (vegetative form) of *B. subtilis* RNA polymerase was identified within the 3' end of ORF 4, approximately 295 bp upstream from ORF 3 and oriented in the same transcriptional direction as ORF 3 (FIG. 4). Integration into *B. subtilis* by a Campbell-type recombination event of an *E. coli* plasmid containing this promoter sequence on a 0.7 kb SalI-BglII restriction fragment did not cause inactivation of riboflavin production in *B. subtilis*, results which indicated that this second sequence ($P_2$) has promoter activity and thus may actually control transcription (in addition to the $\sigma^A$ $P_1$ promoter) of ORF 3, the β subunit riboflavin synthase gene and ORF 2. LacZ fusions and Northern analysis confirmed the existence of this promoter.

7. A third DNA sequence, TTGAAT-(18 bp)-TAAAAA, (SEQ ID NO. 233) possibly resembling the promoter recognized by the $\sigma^A$ (vegetative form) of *B. subtilis* RNA polymerase was identified within the intercistronic region between the β subunit of the riboflavin synthase gene and ORF 2, approximately 83 bp upstream of ORF 2 and oriented in the same transcriptional direction (FIG. 4). This $\sigma^A$ promoter, $P_3$, may also control transcription of ORF 2, in addition to $P_1$ and $P_2$.

8. In vitro-coupled transcription/translation analysis of S-30 reactions of the cloned DNA confirmed that ORF 2, ORF 3, ORF 4, and ORF 5 all actually encoded proteins of the size predicted from their respective sequences.

9. Three of the five presumed enzymatic steps in riboflavin biosynthesis were assigned to specific coding regions by comparing predicted amino acid sequences or molecular weights of their products to published protein sequences, using GenBank®, or known protein sizes.

a. The putative protein encoded by the open reading frame between ORF 2 and ORF 3 almost identically matched the published 154 amino acid sequence of the β subunit for the riboflavin synthase enzyme (Ludwig et al., *J. Biol. Chem.* 262:1016, 1987). Only one amino acid difference was detected: lysine was substituted for glycine at residue 65. This enzyme is reported to catalyze the formation of 6,7-dimethyl-8-ribityllumazine from 5-amino-6-ribitylamino-2,4 (1H,3H)-pyrimidinedione-5'-phosphate (FIG. 1, structures 5 and 4, respectively) and 3,4-dihydroxybutanone-4-phosphate.

b. A 39% identity in an 88-amino acid overlap was identified between the putative product of ORF5 and deoxycytidylate deaminase, a 188 amino acid protein encoded by the *E. coli* bacteriophage $T_2$ (Maley et al., *J. Biol. Chem.* 258:8290, 1983). Based on this result, ORF 5 most likely encodes the rib-specific deaminase that catalyzes the formation of 5-amino-6-(ribosylamino)-2,4(1H,3H-3H)-pyrimidinedione-5'-phosphate from 2,5-diamino-6-(ribosylamino)-4 (3H)-pyridinone-5-phosphate (FIG. 1, structures 3 and 2, respectively).

c. The predicted molecular weight of the ORF 4 gene product (26,000 Da) was in good agreement with the molecular weight of the α-subunit for riboflavin synthase (23,000 Da; Bacher et al., *J. Biol. Chem.* 255:632, 1980). Based on this result, ORF 4 encodes the α-subunit for riboflavin synthase, which catalyzes the final step of the biosynthetic pathway: dismutation of 6,7-dimethyl-8-ribityllumazine to riboflavin (FIG. 1, structures 5 and 6, respectively) and 5-amino-6-ribitylamino-2,4(1H,3H)-pyrimidinedione.

10. The remaining enzymatic steps in riboflavin synthesis were tentatively assigned to coding regions by aligning the position of ORFs to a physical map of rib mutations in the operon (Morozov et al., *Mol. Genet. Mik. Virusol.* no. 7:42 (1984)). Mutations for defective GTP cyclohydrolase were reported to map to the 0.5 kb HindIII fragment. Since ORF 3 encompasses this restriction fragment, we concluded that ORF 3, at least in part, encodes this enzymatic function, which catalyzes the formation of 2,5-diamino-6-(ribosylamino)-4(3H)-pyrimidinone-5'-phosphate from GTP (FIG. 1, structures 2 and 1, respectively). In addition, the biosynthetic gene encoding a rib-specific reductase was reported to be contained entirely within the approximately 1.8 kb HindIII fragment. Since this fragment contains only two complete coding regions, the β subunit of the riboflavin synthase gene and ORF 2, we speculate that ORF 2 encodes the reductase, which catalyzes the formation of 5-amino-6-(ribitylamino)-2,4(1H,3E)-pyrimidinedione-5'-phosphate from 5-amino-6-(ribosylamino)-2,4(1H,3H) pyrimidinedione-5'-phosphate (FIG. 1, structures 4 and 3, respectively).

In addition, a similar rho-independent transcription termination site was detected in the apparent leader region of the operon, downstream of the putative $\sigma^A$ $P_1$ promoter but just upstream of the first coding region of the operon, ORF 5 (FIGS. 4 and 9). This potential terminator structure may be involved in regulation of the rib operon by a termination/anti-termination mechanism. In addition, a roseoflavin-resistant ($R_OF^R$) dependent regulatory region is present on a 0.7 kb SalI-BglII restriction fragment of ORF3.

Assignment of rib ORFs to Protein Products

One method for confirming whether the rib-specific ORFs encode proteins is to "visualize" the size and number of proteins synthesized from the cloned DNA in an S-30 in vitro coupled transcription/translation reaction using pRF2 and its various derivatives as templates. The S-30 fraction kit (New England Nuclear, used according to manufacturer's specifications) is especially efficient in translating B. subtilis genes due to the presence of their strong ribosome binding sites.

Using the cloned 10 kb EcoRI fragment of pRF2 or pRF4 as templates, we expected to detect five putative rib-specific proteins: β riboflavin synthase, 14.7 kilodaltons (kd) (Ludwig et al., J. Biol. Chem. 262:1016, 1987); and the proteins from ORF 2, 13.6 kd; ORF 3, 43.7 kd; ORF 4, 23 kd; and ORF 5, 39.7 kd. We also expected to detect at least two other proteins, encoded by ORF 6 (11.6 kd) and ORF 1 (at least 18.7 kd), as well as any additional proteins encoded by genes present in the unsequenced regions of the 10 kb cloned DNA fragment. In addition, vector-associated proteins, including the bla and cat antibiotic resistance gene products, were also expected (the tet gene is not strongly expressed in S-30 reactions).

Figure 10:
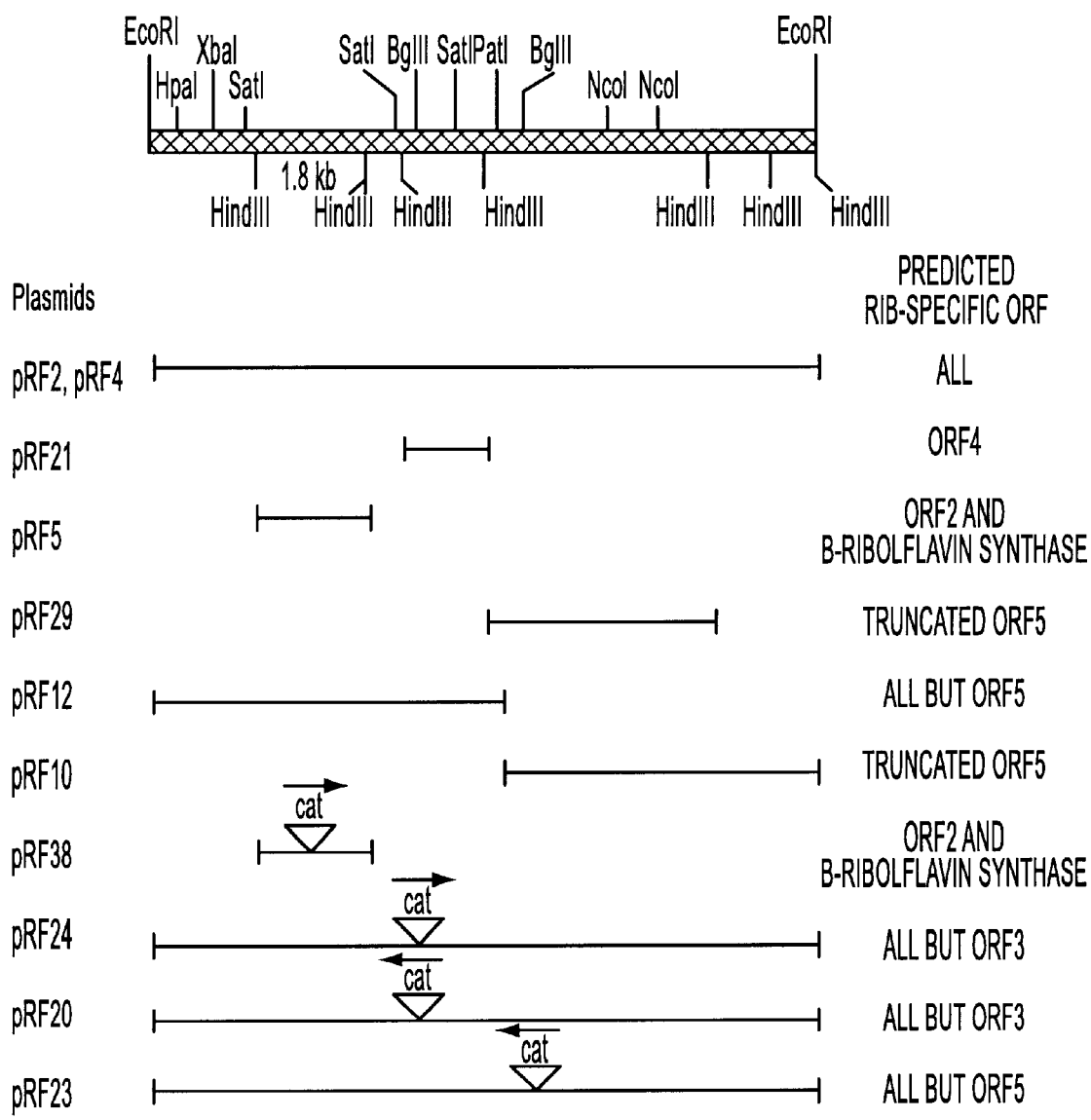
FIG. 10. Structure of various plasmid derivatives used in S-30 in vitro coupled transcription/translation reactions. A schematic diagram is shown of the rib operon regions contained in the plasmid derivatives used in the S-30 reactions, as well as the open reading frames predicted to be expressed.

Excluding the bla- and cat-specific proteins (32 kd and 18 kd, respectively) and other vector-associated proteins, a total of six major $^{35}$S-labelled proteins were detected, with molecular weights of 47 kd, 44 kd, 38 kd, 26 kd, 20 kd and 15 kd, on a 15%-SDS polyacrylamide gel of the S-30 reactions with pRF2 or pRF4. To assign these protein products to their corresponding rib-specific ORFs, S-30 reactions were repeated using various available deletion derivatives, cat-insertion derivatives, and subcloned fragments of the 10 kb EcoRI cloned DNA (FIG. 10). The results are shown in Table V.

TABLE V

RIB-SPECIFIC PROTEINS OBSERVED IN S-30 REACTIONS

| Plasmid | 47,000 Daltons (ORF 3) | 44,000 Daltons (ORF 5) | 26,000 Daltons (ORF 4) | 15,000 Daltons (ORF 2) |
|---|---|---|---|---|
| pRF2 | + | + | + | + |
| pRF4 | + | + | + | + |
| pRF21 | − | − | + | − |
| pRF5 | − | − | − | + |
| pRF29 | − | − | − | − |
| pRF12 | + | − | + | + |
| pRF10 | − | − | − | − |
| pRF38 | − | − | − | − |
| pRF24/pRF20 | − | + | + | + |
| pRP23 | + | − | + | + |

Based on these results, protein products were assigned to ORF 3 (47 kd); ORF 5 (44 kd); ORF 4 (26 kd); and ORF 2 (15 kd), with molecular weights in close agreement with the predicted sizes.

The assignment of products to ORF 2 and the β riboflavin syntnmase gene were less straightforward than the assignments to the other ORFs. Since the S-30 reaction of pRF2 produce a 15 kd protein which was close to the predicted size of the proteins encoded by either gene, it was first assumed that this protein band actually contained both protein species. However, the cat insertion into ORF 2 in plasmid pRF38 completely removed this protein band, replacing it with a much smaller protein of 6 kd, which is in close agreement with the predicted size of the truncated ORF 2. Based on these results, the 15 kd protein appears to be generated only by ORF 2. It is not clear why the β riboflavin synthase protein is not visualized on the gels of the S-30 reactions. Taken in total, however, the results confirmed the existence of five rib-specific coding regions: ORF 5, ORF 4, ORF 3, ORF 2 and the β riboflavin synthase gene.

In addition, ORF 1 appeared to encode a 38 kd protein, while no product was identified for ORF 6.

Regulatory Mechanisms of the Rib Operon

In B. subtilis, a recurring pattern of gene organization and regulation for biosynthetic pathways has been observed by several investigators. The nucleotide sequences of the tryptophan biosynthetic pathway (Henner et al., Gene 34:169, 1984) and the de novo purine nucleotide pathway (Ebbole and Zallin, J. Biol. Chem. 262:8274, 1987) of B. subtilis both contain clustered, overlapping genes transcribed as a polycistronic message and regulated at least in part by a novel transcription termination/anti-termination mechanism, involving a repressor protein which can be encoded by a gene unlinked to the biosynthetic operon (Zalkin and Ebbole, J. Biol. Chem. 263:1595, 1988). Since we found that the organization of the rib biosynthetic and regulatory genes is strikingly similar to those of the B. subtilis trp and pur pathways, we hypothesized that the rib operon might be regulated, at least in part, in a similar manner.

Briefly, the key characteristics of the transcription termination/anti-termination model include (Shimotsu et al., J. Bacteriol. 166:461, 1986): (i) the presence of a long 5' leader sequence that precedes the first gene in the operon; (ii) the presence in the RNA leader of two or more overlapping dyad symmetries that have the potential to form mutually exclusive RNA stem-loops, one structure functioning as a rho-independent transcription terminator and the other as an "anti-terminator" (blocking the formation of the rho-independent transcription terminator); (iii) under repressive conditions, the repressor protein, activated by the end product of the pathway, binds to the nascent mRNA at a site which prevents formation of the anti-terminator, thus allowing formation of the terminator which terminates transcription; (iv) under depressive conditions, binding of the unactivated repressor is precluded, resulting in the formation of the anti-terminator causing read-through transcription into the coding region of the operon.

As discussed above, the most likely site for initiation of transcription in the rib operon is a $\sigma^A$ promoter, $P_1$, located about 290 bp upstream from the first gene in the operon. Preliminary analysis of the RNA leader sequence indicated that it contained most, if not all, of the structures required for regulation by the termination/anti-termination model. Within this region, a stem-loop structure followed by a string of thymidines resembling a rho-independent transcription terminator was identified approximately 50 bp upstream of ORF 5; this sequence has the potential to form a hairpin with a ΔG of −26 kcal/mol (FIG. 9). In addition, several potential stem-loop structures with ΔG's ranging from −13 to −16 kcal/mol were located within the rib 5' leader that could possibly qualify as the anti-terminator sequence.

In addition to the primary site for the initiation of transcription, usually located upstream from the first gene in the operon, there exist in some biosynthetic pathways secondary promoter sites located within the internal regions of the operon. The possibility of there being a second promoter site within the rib locus was also suggested by previous R-loop heteroduplex studies of the rib operon (Osina et al., *FEBS Letters* 196:75–78, 1986), showing two or more sites for the initiation of mRNA synthesis. Our preliminary analysis of the intercistronic gaps of the rib operon did not detect such secondary promoter sites. However, when this analysis was extended to all of the sequences within the operon, another $\sigma^A$ promoter, $P_2$, was identified within the 3' end of ORF 4, just downstream from the SalI restriction site (FIG. 4) Thus it is possible that the expression of ORF 2, ORF 3, and the β-subunit for riboflavin synthase is also under the control of this secondary promoter. In addition, a possible third $\sigma^A$ promoter, $P_3$, was identified just upstream of ORF 2. Therefore ORF 2 is possibly also under the control of this additional promoter.

The location of putative coding regions, promoters and transcription termination sites on the DNA sequence of the 5.5 kb *B. subtilis* rib-specific region is shown in Table VI.

TABLE VI

CODING REGIONS, PROMOTER, AND TRANSCRIPTION TERMINATION SITES OF THE *B. SUBTILIS* RIB OPERON

|  |  | bp Number[a] |
|---|---|---|
| Coding Regions | ORF 6 | 364–678 |
|  | ORF 5 | 1101–2183 |
|  | ORF 4 | 2197–2841 |
|  | ORF 3 | 2859–4052 |
|  | βriboflavin-synthase gene | 4088–4549 |
|  | ORF 2 | 4665–5036 |
|  | ORF 1 | 5567–5057[b] |
| $\sigma^A$ Promoters | $P_1$ | 771–799 |
|  | $P_2$ | 2528–2556 |
|  | $P_3$ | 4545–4574 |
| rho-Independent Termination Sites | Upstream from 5' promoter | 708–748 |
|  | Within 5' leader RNA | 1034–1067 |
|  | At 3' end of rib operon | 5038–5090 |

[a]of FIG. 3.
[b]Coding region oriented in opposite direction.

Example 8: Construction of Vectors Containing a Modified Rib Operon

The above functional analysis of the rib operon of *Bacillus subtilis* for the first time delimiting the regulatory regions and open reading frames in the nucleodde sequence permits construction of new vectors which are useful for increasing the yield of riboflavin production. The knowledge of the location of the specific genes required for riboflavin biosynthesis, of the location of transcriptional control regions, and other relevant regions (e.g., RBS) in those genes allows changes in such regions to be made. There follow a few examples of such manipulations.

Construction of an integration plasmid with a rib operon on a smaller DNA fragment The integrating vector used to construct the riboflavin overproducing strain RB50::[pRF8] contains a 10 kb EcoRI fragment including the rib operon. Since the rib operon appears to occupy less than 6 kb of DNA a new integration vector was constructed (pRF40) containing the, rib operon on a smaller DNA fragment. The smaller size of this clone allows higher amplification of rib genes resulting in higher yields of riboflavin.

Figure 12:
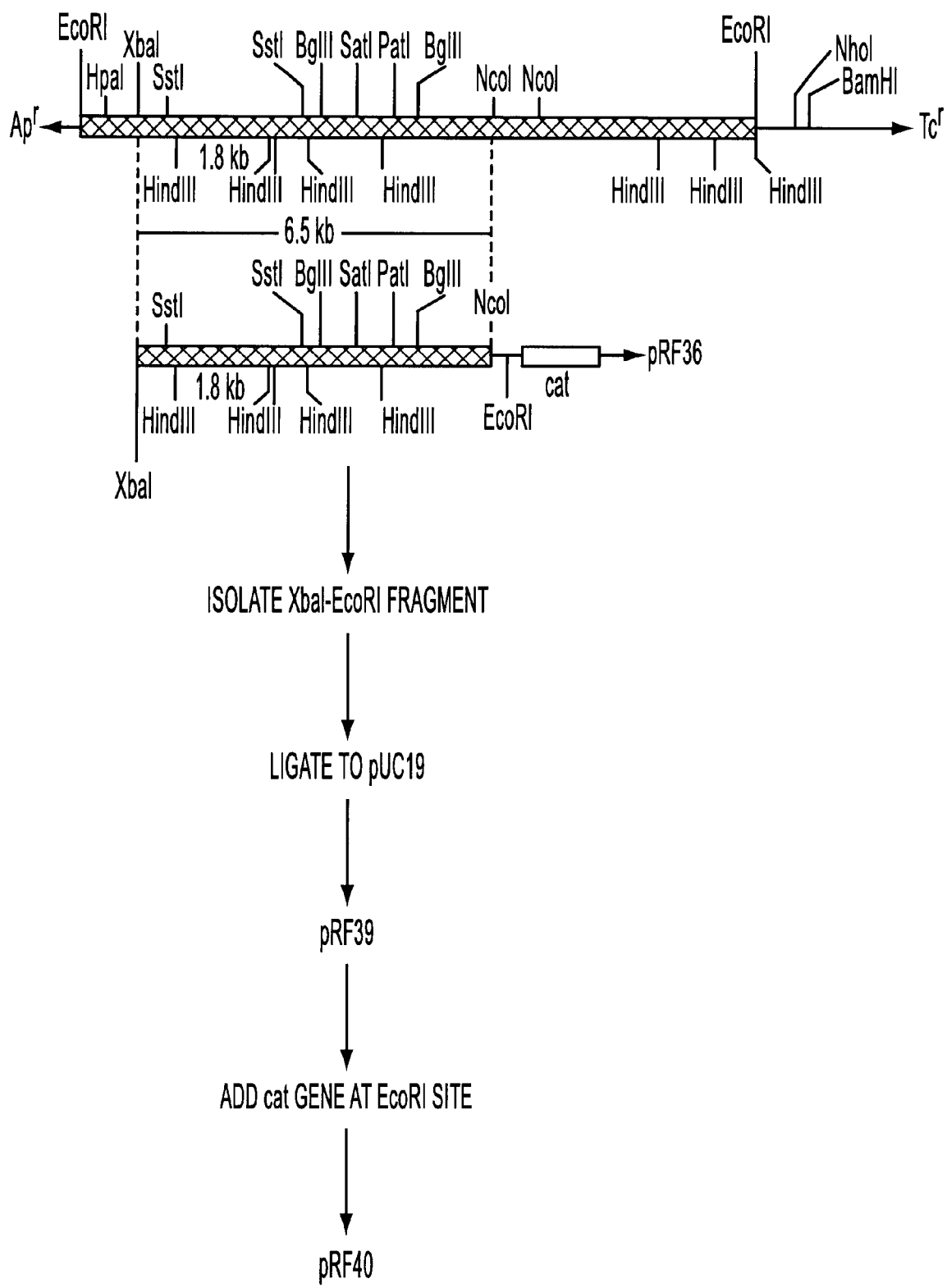
FIG. 12. Construction of pRF40.
Figure 14:
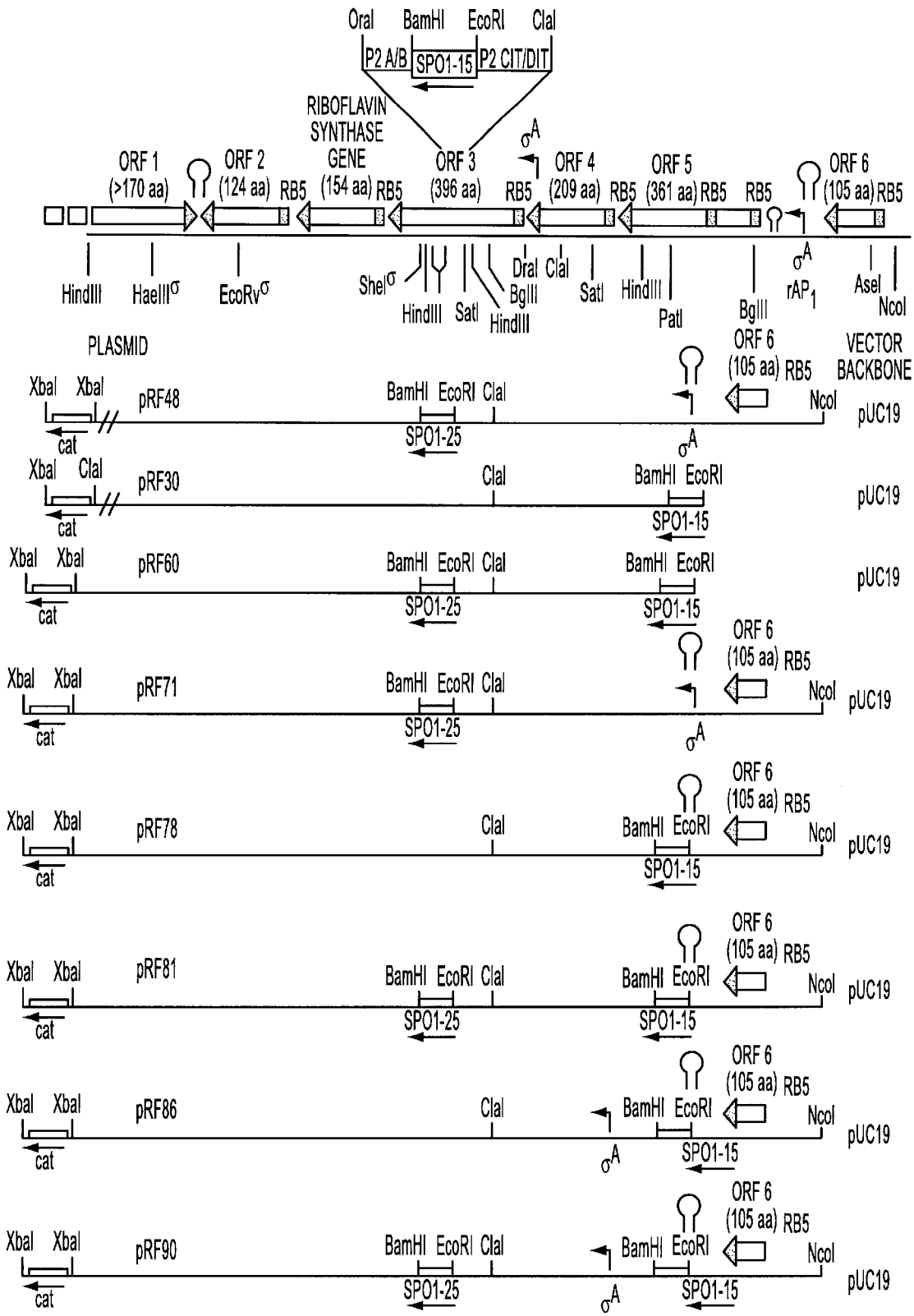
FIGS. 14, 15, and 16. Structure of various vectors.

Referring to FIG. 12, pRF40 was constructed from pRF36 which is a plasmid in which the 0.8 kb NcoI fragment of pRF2 is replaced with a cat gene. The rib operon is contained on a 6.5 kb XbaI-EcoRI fragment. This fragment was isolated and ligated to pUC19 (Yanisch-Perron et al., 33 *Gene* 103, 1985; available from New England Biolabs, Boston, Mass., and Bethesda Research Laboratories, Maryland) digested with XbaI and EcoRI. The ligated DNA was transformed into DH5α*E. coli* and plated onto LB plates containing 40 μg/ml X-gal and 50 μg/ml ampicillin. Analysis of miniprep DNA prepared from white colonies indicated that pRF39 contained the 6.5 kb XbaI-EcoRI fragment.

pRF39 was digested with EcoRI, treated with CIAP, and then ligated to a 1.6 kb EcoRI fragment containing the cat gene. The ligated DNA was then transformed into DH5α*E. coli* and appropriate colonies selected for plating onto LB+10 μg/ml chloramphenicol; two colonies were chloramphenicol-resistant. Analysis of miniprep DNA prepared from these colonies confirmed the presence of the cat gene. One of these plasmids is pRF40 (FIG. 14).

Construction of plasmids containing transcriptionally modified rib operon

As described above, it is useful to replace the promoter and operator regions of the riboflavin operon with promoters allowing constitutive expression of the riboflavin biosynthetic genes. Plasmids containing such constructs can then be used to produce bacterial strains which will produce increased levels of riboflavin. A few examples, not limiting in the invention, are provided below.

Figure 13:
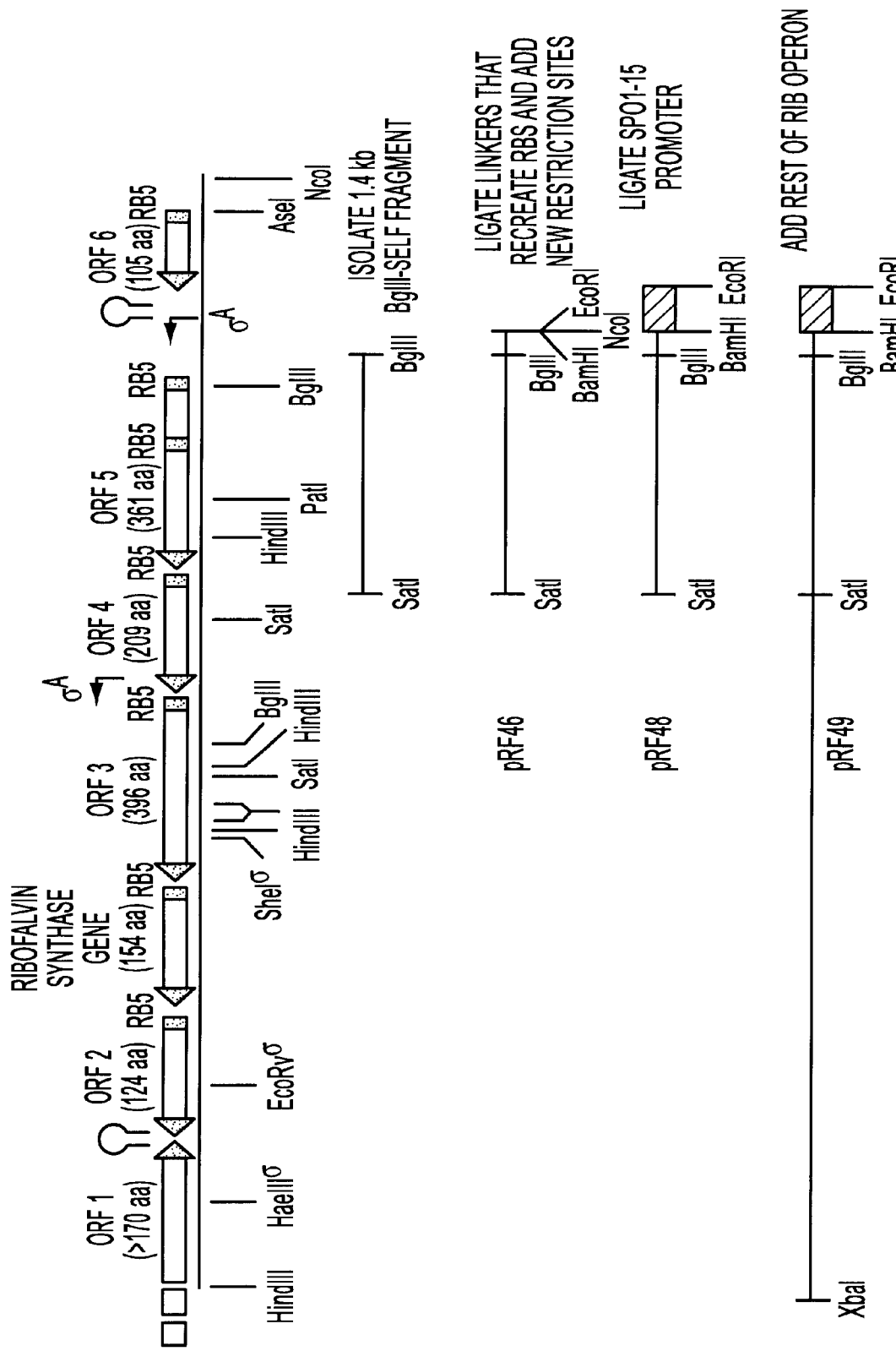
FIG. 13. Construction of pRF50.

Referring to FIG. 13, the riboflavin promoter and regulatory region were removed and replaced with an SPO1 promoter. We took advantage of the BglII site located at position 1130 at the start of ORF3. Oligonucleotides were synthesized (RB5 and RB6, see FIG. 18) that recreated the DNA sequence 5' to the BglII site (the first few amino acids of ORF5 and the SD sequence) up to position 1058. Reconstruction of the 5'-end of the operon stopped before any of the proposed DNA regulatory structures (FIG. 13). At their 5' ends the oligonucleotides contained BamHI, NsiI, and EcoRI restriction sites, allowing for placement of various promoters 5' to the rib operon. Because of the various restrictions sites in the rib operon it was; necessary to construct the operon with the new promoters in several steps, as follows.

A 1.4 kb SalI-BglII fragment was isolated from pRF36 (FIG. 13). This fragment was ligated with the two oligonucleotides and EcoRI-SalI-digested pUC19. The ligated mixture was then transformed into *E. coli* DH5α cells and plated onto LB containing 50 μg/ml ampicillin and 40 μg/ml X-gal. Minipreps were prepared from Ap[r] white colonies; one plasmid having the desired structure is pRF46 (FIG. 13).

pRF46 was digested with BamHI and SalI and the 1.4 kb fragment isolated. This fragment was then ligated with the 400 bp EcoRI-BamHI fragment of pNH202 (pUC8 containing the SPO1-15 promoter, Lee and Pero, *J. Mol. Biol.*, 152:247–265, 1981) and pUC19 cut with SalI and EcoRI. The ligated DNA was then transformed in DH5α*E. coli*, which were plated onto LB+ampicillin+X-gal. Miniprep DNA was prepared from white colonies; and pRF48 had the desired structure (FIG. 13).

pRF48 was digested with EcoRI and SalI and the 1.8 kb fragment isolated. This fragment was ligated with the 4.0 kb XbaI-SalI fragment (containing the rest of the rib operon) from pRF2 and XbaI, EcoRI-cut pUC19. The ligated mixture was then transformed into *E. coli* DH5α cells which were plated on LB+ampicillin+X-gal. Miniprep DNA was prepared from white colonies; pRF49 had the desired structure, and supernatants from culture containing this plasmid was yellow, indicating riboflavin production (FIG. 13).

To place the cat gene in pRF49, to allow selection in *B. subtilis*, the plasmid was digested with XbaI and ligated to a 1.3 kb cat-containing XbaI fragment from pEcc4. The ligated DNA was transformed in *E. coli* DH5 cells. Hundreds of Ap$^r$ colonies resulted, and the colonies were patched onto plates containing LB+10 μg/ml chloramphenicol. Approximately 10% of the colonies grew on the chloramphenicol plates, indicating the presence of the cat gene. One cat-containing plasmid is called pRF50 (FIG. 14).

The above example shows placement of a new promoter upstream of ORF5. We found that it is also useful to place a promoter after P$_2$ between ORF3 and ORF4 in order to further increase riboflavin production. An example of such construction now follows.

Figure 15:
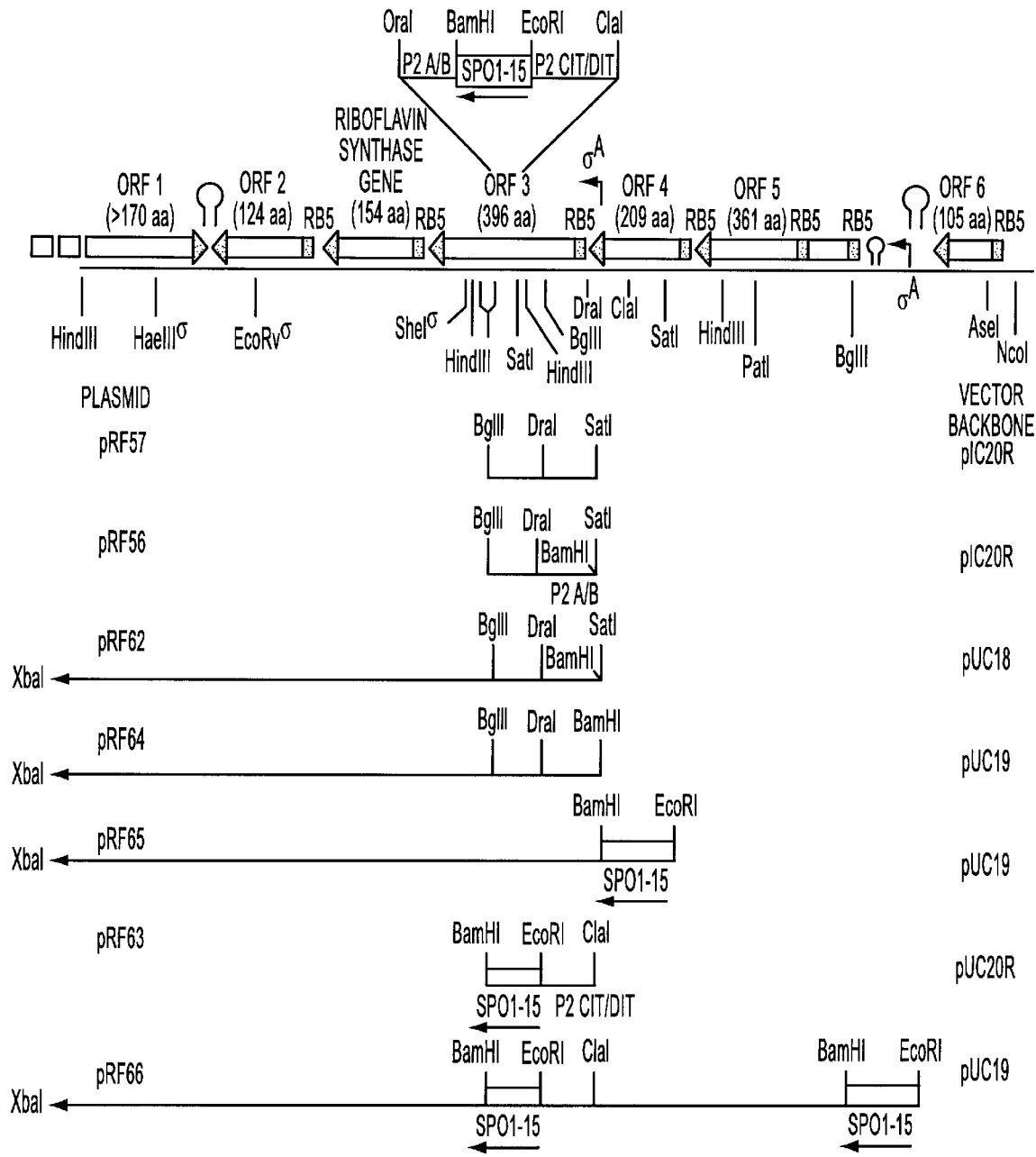

Referring to FIGS. 14 and 15, to place a copy of the SPO1-15 promoter upstream of ORF3 we made use of the restriction sites adjacent to the ORF4-ORF3 junction. The ClaI site at position 2767 is located at the end of ORF4 and is unique in the rib operon. Another useful restriction site near the beginning of ORF3 is the DraI site at position 2892. Oligonucleotides were synthesized that recreated the sequence from the above-mentioned DraI site past the start of ORF3 and placed a unique BamHI site before the beginning of ORF3 (linkers P2-A and P2-B, FIG. 18). Another set of oligonucleotides recreated the sequence from the ClaI site past the end of ORF4 and placed an EcoRI site at that location (linkers P2-CII and P2-DII, FIG. 18). The SPO1-15 promoter, located on a EcoRI-BamHI fragment, was then be placed between the BamHI and EcoRI sites created by the oligonucleotides. The entire operon was put together with this additional SPO1-15 promoter as follows.

Referring to FIG. 15, the 750 bp SalI-BglII fragment containing the ORF4-ORF3 function was subcloned to pIC2OR (Marsh et al., *Gene* 32:481–485, 1984). The resulting plasmid, pRF57, was then digested with DraI and BglII, and the predicted 270 DraI-BglII fragment was isolated. This fragment and linkers P2-A and P2-B were ligated to pIC2OR cut with SalI and BglII. The linkers placed BamHI and SalI sites upstream of the 5' end of ORF3. (The SalI site was chosen for convenience since BglII and BamHI sites are compatible and will be removed later.) The ligation was transformed into *E. coli* DH5α cells. Plating onto LB medium+Amp and X-gal resulted in white colonies; pRF58 had the desired structure. The 330 bp BglII-SalI fragment from pRF58 was isolated and ligated with 3.3 kb BglII-XbaI fragment containing the 3'-end of the rib operon from pRF36 (FIG. 12) and pUC19 cut with XbaI and SalI. The ligated DNA was then transformed into *E. coli* DH5α cells, resulting in white colonies; pRF62 (FIG. 15) had the desired structure. For convenience, the 3.6 kb BamHI-XbaI fragment was isolated from pRF62 and subcloned into BamHI-, XbaI-cut pUC19 (pRF64, FIG. 15). This plasmid now contained the 3.6 kb 3'-end of the rib operon with an engineered BamHI site preceding ORF3.

To place the SPO1-15 promoter in front of the 3'-half of the rib operon containing the last three open reading frames, we digested pRF64 with EcoRI and BamHI and ligated it to a 400 bp EcoRI-BamHI fragment containing the SPO1-15 promoter. The ligated DNA was transformed into *E. coli* DH5 cells and miniprep DNA was prepared; pRF65 has the desired structure.

The SPO1-15 promoter was than engineered to place a ClaI site upstream of the promoter to reconstruct the end of ORF4. The EcoRI-BamHI fragment from pNH202 containing the SPO1-15 promoter was ligated with linkers P2-CII and P2-DII and pCI2OR-digested with BamHI and ClaI. The ligated DNA was then transformed into *E. coli* DH5α cells.

White colonies resulted and miniprep analyses indicated that pRF63 had the desired structure. The 470 bp CarI-BamHI fragment was isolated then from pRF63 and ligated to the 2 kb EcoRI-ClaI fragment from pRF49 containing the SPO1-15 promoter and the 5'-end of the rib operon and pRF64 (FIG. 15), containing the SPO1 promoter and the 3'-end of the operon, digested with EcoRI and BamHI. The ligated DNA was then transformed into *E. coli* DH5α cells. Miniprep DNA was prepared; pRF66 had the desired structure. In addition, *E. coli* containing pRF66 produced small amounts of riboflavin on LB medium+ampicillin plates, confirming that the operon was still intact The last step was to ligate the cat gene into the unique XbaI sites of pRF66 as described above. The resulting plasmid, pRF69 (FIG. 15) contained the cat gene in the same direction as the rib operon.

Figure 16:
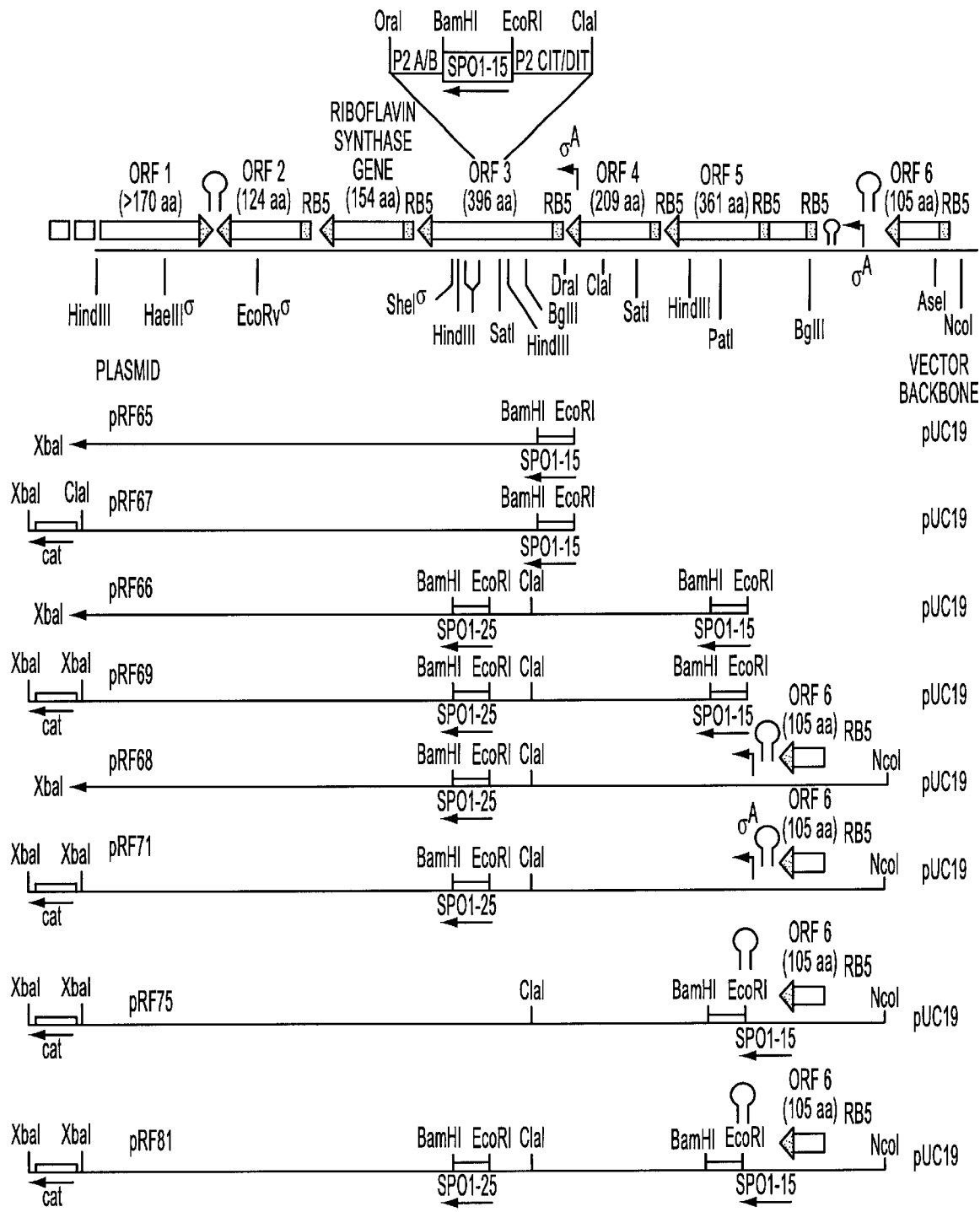

To construct a plasmid containing the entire operon with the natural or wild-type ribP$_1$ promoter and the SPO1-15 promoter after ribP$^2$, the 6.3 kb EcoRI-BamHI fragment of pRF64, the 2.75 kb EcoRI-ClaI fragment of pRF36, and the 470 bp ClaI-BamHI fragment of pRF63 were ligated and tranformed into *E. coli* DH5α cells. About 50% of the Ap$^r$ colonies were yellow, indicating ribflavin production. Miniprep DNA was prepared from yellow colonies and pRF68 had the desired structure (FIG. 16). A cat gene was added to pRF68 at the XbaI site, as discussed above, to generate pRF71 (FIG. 16). This plasmid contained the cat gene in the same direction as the rib operon.

As another example of the construction of useful plasmids in this invention, there now follows an example in which one or more promoters can be introduced within the riboflavin operon without prior removal of existing DNA sequences.

As an example, a prototype modified operon was constructed in pRF78, which contains a single copy of the SPO1-15 promoter inserted within a 30 bp non-essential region located between ribP$_1$ and a putative rho-independent transcriptional termination site (FIG. 14), an inactivated ribP$_1$ promoter to prevent possible transcriptional interference of the SPO1-15 promoter, an active ribP$^2$ promoter, the five structural genes encoding rib biosynthetic enzymes, and approximately 1.5 kb of flanning DNA nucleotide sequences downstream from the end of the riboflavin operon.

Figure 17:
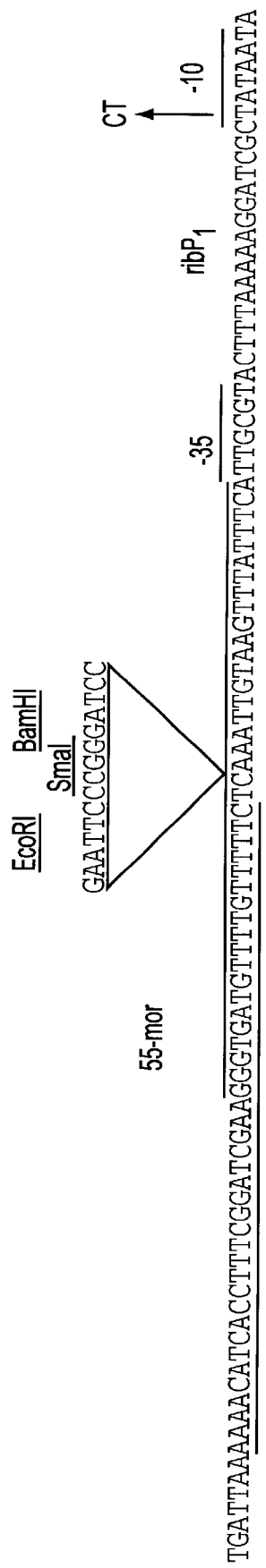
FIG. 17. 55-mer used in plasmid construction (SEQ ID NO. 221).

Referring to FIG. 14, the 1.7 kb NcoI-PstI fragment of pRF2, a fragment that contains the 5' promoter region of the rib operon and flanking regions, was first subcloned into mp19, a derivative of the *E. coli* bacteriophage vector M13 (United States Biochemical Catalog, 60–61, 1987; available from New England Biolabs, Massachusetts). One recombinant phage, M1.7, was recovered and standard DNA sequence analysis of the promoter region revealed a spontaneous mutation of the −10 region of the ribP$_1$ promoter, a TA-to-CT change, which mays inactivate the promoter Single stranded DNA was prepared and annealed to a synthetically-generated 55 bp DNA oligomer (see FIG. 17), containing a combination of restriction enzymes sites, 5'-EcoRI-SmaI-BamHI-3', flanked on either side by additional sequences homologous to the DNA region upstream from ribP$_1$. Double-stranded DNA molecules were synthesized using standard site-directed mutagenesis (SDM) protocols. These DNA molecules were introduced into the *E. coli* host TG-1 (available from Amersham Corp. Illinois) by transfection to generate recombinant phage plaques. One recombinant phage was found to contain the desired modified DNA sequence, as determined by standard DNA sequence analysis.

The modified rib promoter region was then rejoined to the rib structural genes of the operon using a pair of unique NsiI restriction enzymes sites 750 bp apart that flank the ribP$_1$ region and surrounding sequences. Double-stranded DNA molecules of the phage recombinant were prepared, digested with NsiI, the 750 bp fragment isolated, and the fragment ligated to dephosphorylated, 8.7 kb NsiI fragment of pRF39ΔR1 (a plasmid derived from pRF39, FIG. 12, that contains the wild-type rib operon). The ligated DNA molecules were introduced into E. coli DH5α cells by transformation, selecting for ampicillin-resistance, which resulted in the recovery of an Ap$^r$ colony harboring the desired recombinant plasmid, pRF75.

The SPO1-15 promoter was next inserted upstream from ribP$_1$ by digesting pRF75 with a combination of EcoRI and BamHI enzymes, ligating the cut DNA to purified 400 bp EcoRI-BamHI SPO1-15-containing restriction fragment, and introducing the ligated DNA into E. coli DH5α cells by transformation, selecting for ampicillin-resistance. One Ap$^r$ colony was found to harbor the recombinant plasmid, pRF77, containing the desired SPO1-15-modified rib operon. A chlorarnphenicol-resistance gene, cat, on a 1.6 kb XbaI restriction fragment, was subsequently introduced into pRF77 at the unique XbaI site, generating plasmid pRF78 (FIG. 14).

This prototype operon was further modified to contain an active ribP$^1$, promoter, and/or a second copy of the SPO1-15 promoter introduced downstream from ribP$_2$ within a intercistronic region between the rib coding regions ORF3 and ORF4, as described above. For example, plasmid pRF88, containing a derivative of the modified rib operon in pRF78 with an active ribP$_1$ promoter (FIG. 14) was constructed by the same procedure described above, using a recombinant phage containing the wild-type ribP$_1$ promoter. In other examples, a second copy of the SPO1-15 promoter, located downstream from ribP$_2$, was inserted into the existing modified rib operon-containing plasmids pRF78 and pRF88 by removing the 2.0 kb BglII fragment of either plasmid DNA and inserting the 2.4 kb BglII fragment of pRF66, generating plasmids pRF81 and pRF89 respectively (FIG. 14).

Construction of Ade$^+$ RB50 strains

It is important to use strains of bacteria that require as few components to be added to a fermentation medium as possible. Such strains are cheaper to ferment in order to produce riboflavin. To this end, adenine revertants which contained amplified modified rib operons were constructed. These revertants may not be true revertants of pur-60, but rather include mutations at another site which suppresses the requirement for adenine. As discussed below they produce about 25% more riboflavin than the non-reverted strains. Examples of such constructions are now described.

Plasmids pRF8, pRF40, pRF50, pRF69, pRF71, pRF78, pRF81, pRF88 and pRF89 were each transformed into RB50 (a RoF$^r$, deregulated B. subtilis strain) selecting for chloramphonicol resistance (Cm$^r$). A resistant colony was chosen for each strain. Ade$^+$ revertants of each strain was isolated by growing bacteria in RMM1 broth containing 10 μg/ml adenosine, and plating samples of the cultures onto minimal agar plates. One colony from each Ade$^+$ strain was selected and the vector DNA was amplified by selecting colonies that grow on increasingly higher levels of chloramphenicol, to a maximum level of 60 μg/ml.

Second site Integration

As described above, it is important to amplify an engineered rib operon in the B. subtilis chromosome to achieve high titers of riboflavin. It is also important to ensure that the number of DNA copies of the rib operon within a chromosome are not limiting to riboflavin production. Further amplification of the rib operon can be achieved by integrating and amplifying copies of the rib operon at more than one site in the B. subtilis chromosome to further increase riboflavin yield. One example of how such second site integration can be achieved is described below.

The above described vectors have all relied upon the cat gene to select for integration at the site of the rib operon. In order to insert the rib genes at a second site, it is preferable to have a different antibiotic resistance gene for use at that second site. For example, a tetracycline-resistance (tet) from B. subtilis can be used (Perkins and Youngman, J. Bacteriol., 155:607–615, 1983). Such tet genes are well known to those of ordinary skill in the art and are readily available to such persons. In one such construction, for example, pRF78 (FIG. 14), which contains a modified version of the rib operon, the plasmid can be cut with XbaI and ligated to a 2.4 XbaI fragment containing the tet gene. The resulting plasmid contains the tet gene at the XbaI site and is called pRF85 as shown in FIG. 16.

A strain which is deleted for the entire rib operon and which has a tet gene integrated at a second site is required to cause integration of pRF85 at that site. One such site is the bpr gene encoding bacillopeptidase F, a minor non-essentiall extracellular protease. An E. coli plasmid containing the bpr gene, pKT2, (Sloma et al., J. Bacteriol., 172:1470–1477, 1990) was digested with EcoRV. This EcoRV site is in the coding region of bpr. The DNA was then ligated to a 2.4 kb EcoRI fragment containing the tet gene that had been blunt-ended. The resulting plasmid (containing the tet gene at the EcoRV site of bpr) was called pKT2-tet. This DNA was linearized with EcoRI and then transformed into RB52, a strain deregulated for riboflavin synthesis. Tet$^r$ colonies resulted and one such colony was called RB54. The integrated tet gene at bpr will function as a homologous sequence for the integration of pRF85.

To ensure that the cloned riboflavin operon of pRF85 would be inserted at the second chromosomal site containing the tetracycline-resistance gene, a region containing the original riboflavin operon and flanking DNA, equalling that contained in pRF85, was deleted from the chromosome of RB54 by in vitro methods. Briefly, this involves first generating an E. coli recombinant plasmid where the cloned riboflavin operon and flanking regions between the NcoI and XbaI restriction sites are removed and replaced by a chloramphenicol-resistance gene, cat that is expressed in B. subtilis bacteria. This plasmid is then used to delete the chromosomal riboflavin operon by transforming RF54 with linearized plasmid molecules and selecting for chloramphenicol resistant (Cm$^r$) bacteria. Cm$^r$ bacteria result from a recombinant event (marker-replacment) which replaces the wild-type rib genes with the deleted copy containing the cat gene.

Specifically, plasmid pRF34 (see example 6) was used to generate an E. coli plasmid containing an in vitro-generated riboflavin operon deletion. This plasmid is derived from pRF2 where the riboflavin operon is flanked on either end by two unique XbaI sites (one site located upstream from the 5'-end of the rib operon next to the deleted 0.8 kb NcoI fragment and the second site located approximately 1.6 kb downstream from the end of the operon) and a cat gene is inserted outside of this region. By digesting pRF34 with XbaI and ligating the cut DNA molecules under dilute DNA concentrations, a recombinant plasmid, pRF82, was recovered where a 7.2 kb region containing the riboflavin operon is removed and essentially replaced with the cat gene. Plasmid pRF82 was linearized by restriction enzyme digestion and the cut DNA used to remove the chromosomal riboflavin operon of RB54 by DNA transformation, selecting for Cm$^r$ bacteria, resulting in marker replacement. Cm$^r$ colonies were screened for riboflavin auxotrophy and one Rib$^-$Cm$^r$ colony, RB55, was recovered for further investigation.

Plasmid pRF85 was transformed into strain RB55, selecting for Rib$^+$. One Rib$^+$ transformant was chosen and called RB58. This strain has the rib operon integrated at bpr by homologous recombination between the tet$^r$ genes in the plasmid and the chromosome. A transducing lysate of RB58 was prepared using standard techniques, and it was used to transduce RB50::[pRF69], selecting for Tet$^r$. These resistant colonies were found to have the modified rib operon integrated at the site of the rib operon and at bpr. One such Tc$^r$ colony RB50::[pRF69]$_{60}$::[pRF85]$_{120}$Ade$^+$ was recovered for further study. The rib operon integrated at rib was amplified by selecting for colonies that grow in the presence of increasing levels of chloramphenicol as described above, and the second copy of the rib operon was amplified by selecting colonies that grow on increasing levels of tetracycline to 120 μg/ml.

Example 9: Fermentative Production of Riboflavin

Evaluation of riboflavin-overproducing strains was conducted in Chemap 14-liter vessels in carbon-limited fed-batch fermentations, with riboflavin content measured by HPLC. Since enzymes encoded by the genes for riboflavin synthesis are rate-limiting, the rib genes, which were amplified, were maintained at high-copy number by the inclusion of 60 μg/ml chloramphenicol in the inoculum seed train, but not in the fermentor.

A culture of a riboflavin-overproducing strain such as *B. subtilis* RB50::[pRF69]$_{60}$Ade$^+$ was grown on Tryptose Blood Agar Base (TBAB Difco) containing 60 λg/ml of chloramphenicol (CAM). Colonies were transferred to 300 ml baffled flasks containing 25 ml of riboflavin minimal medium (RMM; containing sodium glutamate 2.0 g/l, Casamino acids (Difco) 0.2 g/l, Yeast extract (Difco) 0.2 g/l, KH2PO$_4$ 6.0 g/l, K$_2$HPO$_4$ 14.0 g/l, (NH$_4$)$_2$SO$_4$ 2.0 g/l, sodium citrate 1.0 g/l, MgSO$_4$.7H$_2$O 0.2 g/l, glucose 15.0 g/l, pH 7.0) with 60 μg/ml CAM. The inoculated flasks were incubated by shaking at 250 rpm and 37° C. After 8 hours, sterile glycerol was added to a final concentration of 15% and 1 ml aliquots were stored at −80° C.

In order to initiate a fermentation a frozen vial of the appropriate strain, e.g., RB50::[pRF69]$_{60}$Ade$^+$ was thawed at 37° C. and transferred into a 300 ml baffled flask with 25 ml of RMM with 60 μg/ml CAM and shaken at 250 rpm and 37° C. After 8 hours, 6 ml of the growing culture was used to inoculate 300 ml of fermentation medium (see Table VII below) in a series of 2 liter transfer flasks. Each flask contained 300 ml of fermentation medium to which had been added 90 ml of 15% glucose. Chloramphemnicol was added to a final concentration of 60 μg/ml. After incubation for 12 hours at 200 rpm on a shaker with a 2" diameter orbit at 37° C., the contents of each flask was transferred to 7 liters of fermentation medium in a 14 liter fermentation vessel.

During fermentation, the broth was continually monitored for pH and dissolved oxygen (DO$_2$). Off gas was continuously analyzed by quadrapole mass spectrometry and carbon dioxide evolution (CER) and oxygen uptake rates were recorded.

A comparison of several fermentations demonstrated the reproducibility of the control systems. The initial carbohydrate was exhausted from fermentation with RB50::[pRF8]$_{60}$ after 4 hours of growth, causing a rise in pH and a fall in CER. At that point, carbohydrate feeding was initiated and logarithmic growth resumed until DO$_2$ became limiting at 6 hours. The rate of carbohydrate feeding was computer-controlled to maintain the DO$_2$ between 10–20% of saturation throughout the remaining fermentation time.

Excess carbohydrate in the fermentors does lead to oxygen starvation and reduced riboflavin production. Oxygen transfer limitations determine the duration of logarithmic growth, final cell density and the riboflavin production rate. To increase the oxygen transfer rate, Chemap fermentors were run at 1000 rpm with a head pressure of 0.6 atmospheres.

Figure 11:
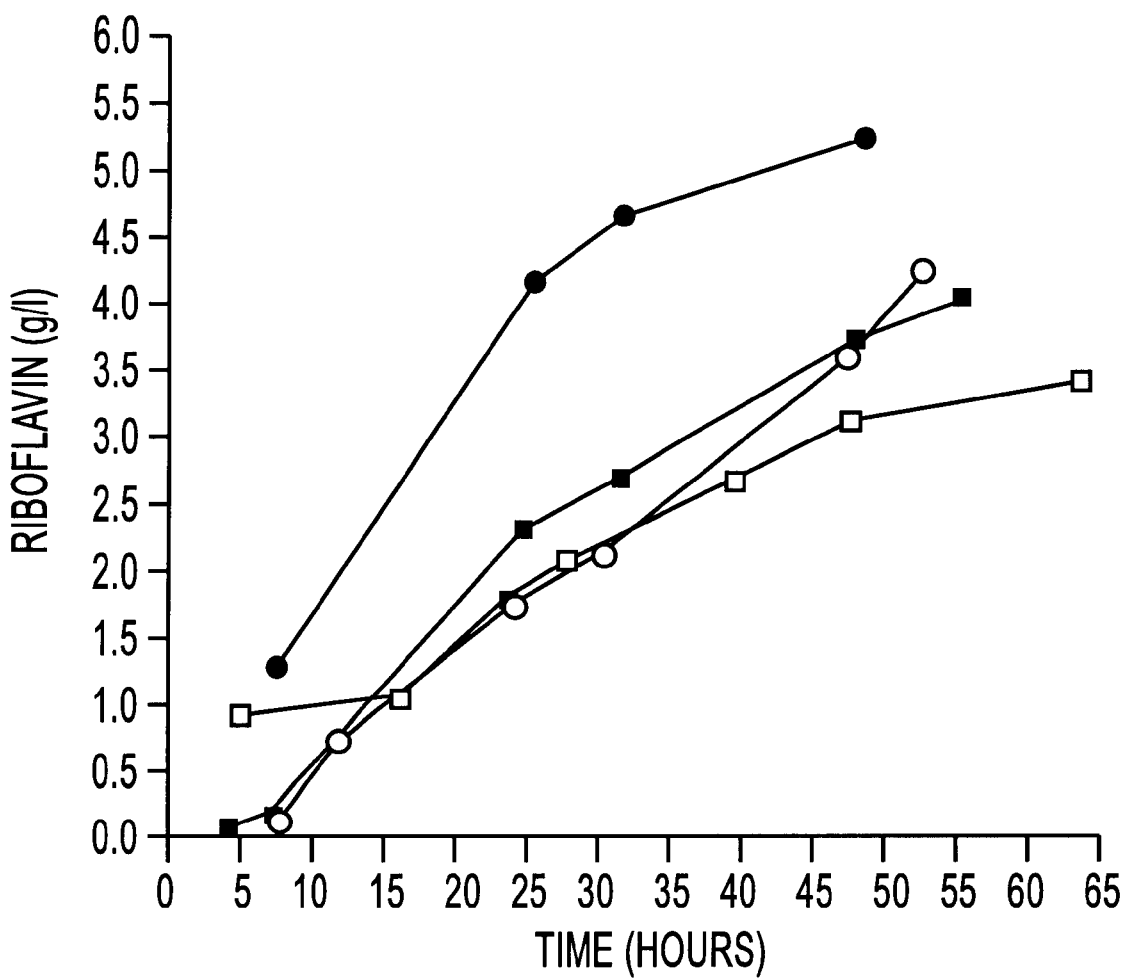
FIG. 11. Comparison of riboflavin production curves. Riboflavin production curves for various fermentation protocols are shown. Open squares: RBF-14 using RB50::[pRF8]$_{60}$ (Ade$^-$). Closed squares: RBF-22 using RB50::[pRF8]$_{60}$(Ade$^-$). Open circles: RBF-23 using RB50::[pRF8]$_{60}$(Ade$^-$). Closed circles: RBF-29 using RB50::[pRF8]$_{60}$ (Ade$^+$).

Supplementation of the medium carbohydrate feed with yeast extract led to an increase in riboflavin production as compared to media without supplementation (FIG. 11, open squares: RBF-14; Table VII). However, because of its high cost, the amount of yeast extract was systematically reduced by substituting less expensive, inorganic ingredients. Substitution of ammonium hydroxide for sodium hydroxide in pH control allowed a reduction of yeast extract in the feed and resulted in an increase in both cell mass and riboflavin titer (FIG. 11, closed squares: RBF-22; Table VII). Fermentation times were also reduced. In other fermentations, moreover, yeast extract was completely eliminated from the feed and replaced with a combination of inorganic salts of ammonium and phosphate, resulting in a further increase in riboflavin production and a reduction of process time (FIG. 11, open circles: RBF-23; Table VII).

The original RB50::[pRF8]$_{60}$ was auxotrophic for adenine because of its pur-60 mutation. When experiments were conducted to determine the minimum amount of adenosine required by the strain, in order to minimize its inhibition of earlier biosynthetic enzymes involved in the pathway leading to the riboflavin-precursor IMP (FIG. 2), RB50::[pRF8]$_{60}$ (and, in general, RB50 strains with a rib operon amplified within their chromosome) was found to be unstable in its adenosine requirement and prototrophic revertants (Ade$^+$) were produced at a fairly high frequency. In shake flasks, the Ade$^+$ revertants appeared to grow and produce riboflavin at least as well as the RB50::[pRF$^8$]$_{60}$ parent. When evaluated in fermentors, the revertant, RB50:: [pRF8]$_{60}$(Ade$^+$), did not require adenosine in the media formulation. More importantly, the revertant grew at a faster rate and produced 25% more riboflavin than its parent strain in less time. A titer of 5.4 g/l riboflavin was produced in 49 hours (FIG. 11, closed circles: RBF-29; Table VII). In additional fermentations, moreover, Hy Soy T was removed from the initial charge or medium and replaced with corn steep liquor, resulting in a further increase in riboflavin production to 6.3 g/l in 48 hours. (RBF-42, Table VII).

Under these fermentation conditions, further significant increases in riboflavin production were demonstrated using bacterial strains that contained engineered riboflavin operon DNA. Strains containing the wild-type riboflavin operon on a 6.5 kb EcoRI-XbaI restriction fragment, RB50::[pRF40]$_{60}$(Ade$^+$), produced 7.4 g/l of riboflavin in 48 hours. Moreover, strains containing a transcriptionally-modified rib operon where the ribP$_1$ promoter and regulatory region were replaced by the constitutive SPO1-15 promoter, RB50:: [pRF50]$_{60}$(Ade$^+$), produced 9.0 g/l of riboflavin in 48 hours. These results demonstrate that modification of the riboflavin operon through the removal of regulatory regions and/or through the introduction of stronger, constitutive exogenous promoters leads to increases in riboflavin titer.

TABLE VII

| Component | RBF-14 | RBF-22 | RBF-23 | RBF-29 | RBF-42 |
|---|---|---|---|---|---|
| Initial Charge (g/l) | | | | | |
| Glucose | 10.00 | 15.00 | 15.00 | 15.00 | 15.00 |
| Corn step liquor | — | — | — | — | 10.00 |
| Hy Soy T | 15.00 | 15.00 | 15.00 | 10.00 | — |
| Sodium glutamate | — | — | — | 5.00 | 5.00 |
| Amberex 500 | 15.00 | 15.00 | 20.00 | 20.00 | 20.00 |
| $KH_2PO_4$ | 5.00 | 5.00 | 7.50 | 7.50 | 7.50 |
| $MgCl_2 \cdot 6H_2O$ | 0.5 | 0.5 | 1.50 | 1.50 | 1.50 |
| $MnSO_4$ | 0.05 | 0.05 | 0.05 | 0.05 | 0.05 |
| Adenosine | 0.05 | 0.05 | 0.05 | — | — |
| MAZU DF37 | 2.50 | 2.50 | 2.50 | 2.50 | 2.50 |
| $FeCl_3$ | — | — | 0.025 | 0.02 | 0.02 |
| $CaCl_2$ | — | — | 0.50 | 0.50 | 0.50 |
| $ZnSO_4$ | — | — | 0.0005 | — | — |
| $CuCl_2$ | — | — | 0.001 | — | — |
| $CoCl_2$ | — | — | 0.0013 | — | — |
| Nutrient Feed (g/l) | | | | | |
| Amberex 500 | 160.00 | 120.00 | — | — | — |
| $NH_4Cl$ | — | — | 7.50 | 7.50 | 7.50 |
| $(NH_4)_2SO_4$ | — | — | 7.50 | 7.50 | 7.50 |
| $KH_2PO_4$ | — | — | 15.00 | 15.00 | 15.50 |
| $MgSO_4 \cdot 7H_2O$ | — | — | 2.50 | 2.50 | 2.50 |
| DL-70 syrup (as DS) | 600.00 | 600.00 | 600.00 | 660.00 | 600.00 |
| pH Control Range | | | | | |
| 6.6 | $H_2SO_4$ | $H_2SO_4$ | $H_2SO_4$ | $H_2SO_4$ | $H_2SO_4$ |
| 6.5 | NaOH | $NH_4OH$ | $NH_4OH$ | $NH_4OH$ | $NH_3$ |
| Conditions | | | | | |
| Air (vvm) | 1.0 | 1.5 | 1.5–2.0 | 1.5 | 1.50 |
| RPM | 1000.0 | 1000.0 | 1000.0 | 1000.0 | 1000.0 |
| Temp ° C. | 37.0 | 37.0 | 37.0 | 37.0 | 37.0 |
| Pressure (bar) | 0.5 | 0.5 | 0.5–0.75 | 0.6 | 0.6 |
| Riboflavin (g/l) 3.4 | 4.1 (64 hrs) | 4.3 (56 hrs) | 5.4 (53 hrs) | 6.3 (49 hrs) | (48 hrs) |
| Dry Weight (g/l) | 33.6 | 36.0 | 36.8 | ND | 44.6 |

The kinetics of riboflavin production in the various fermentations were analyzed using the Luedeking-Piret model. In all cases, the specific productivity declined from the conclusion of the exponential growth phase to the end of fermentation. Also, it was clear that riboflavin production was growth-associated under the fermentation conditions used.

We have discovered that the yield of riboflavin can be increased by changing the fermentation components and conditions. The yield of riboflavin can be increased compared to those conditions described above using those fermentation components and conditions shown in Table VIII.

TABLE VIII

| | RBF 150 (g/liter) | RBF 184 (g/liter) |
|---|---|---|
| Initial Batch | | |
| Yeast Extract | 20 | 20 |
| Glucose | 25 | 25 |
| $KH_2PO_4$ | 7.5 | 7.5 |
| $MgCl_2 \cdot H_2O$ | 1.5 | 1.5 |
| $CaCl_2 \cdot 2H_2O$ | 1.0 | 1.0 |
| $MnSO_4$ | 0.05 | 0.05 |
| $FeCl_3 \cdot 6H_2O$ | 0.025 | 0.025 |
| Mazu DF37C | 2.5 | 2.5 |
| Corn Steep Liquor | 10 | — |
| Sodium Glutamate | 5 | 5 |
| $(NH_4)_2SO_4$ | — | 0.3 |
| Feed Medium (3 liters total used) | | |
| Glucose | 583.3 | — |
| NaCitrate | 6.67 | 6.67 |
| $KH_2PO_4$ | 15 | 15 |
| Succinic Acid | 1.67 | 1.67 |
| $MgSO_4 \cdot 7H_2O$ | 1.67 | 1.67 |
| Corn Syrup Solids | — | 833 |

Briefly, in one such fermentation the startng material is 6.65 liters of batch medium and 0.35 liters of bacterial (RB50::[pRF50]$_{60}$Ade$^+$) inoculant. Oxygen levels are monitored with a Chemap polarographic dissolved oxygen electrode. Dissolved oxygen levels are maintained at 15%±5% by means of computer regulated addition of the feed medium. Total feed added is about 3.0 liters in 48–56 hours. Fermentation pH is maintained at 6.5±0.1 (using 1N $H_2SO_4$ and $NH_3$ gas), and fermenter pressure is maintained at 0.6 bars, temperature at 37° C., and air flow at 10.5 liters/min. Under these conditions, strain RB50::[pRF50]$_{60}$(Ade$^+$) produced 11.0 g/l riboflavin in 48 hours, which represents an improvement in production of approximately 20% compared to the previous fermentation conditions. An increase in riboflavin production was demonstrated (RBF150, Table VIII) using the bacterial strains RB50::[pRF69]$_{60}$(Ade$^+$) containing a transcriptionally-modified riboflavin operon containing two SPO1-15 promoters, one replacing ribP$_1$ and regulatory sequences, and a second inserted between ORF3 and ORF4. This strain produced 13.0–14.0 g/l riboflavin in 48 hours, and 15 g/l in 56 hours, demonstrating that increased transcription of the riboflavin operon using two strong exogeneous promoters increases production levels of riboflavin. Finally, a further increase in riboflavin production was demonstrated using the bacterial strain RB50::[pRF69]$_{60}$::[pRF85]$_{120}$Ade$^+$ containing two amplifiable rib loci as in Example 8. This strain was grown at pH 6.8 and 39° C. using the modified fermentation medium shown in Table VIII (RBF 184) and riboflavin was isolated.

Example 10
Construction of B. subtilis Strain RB50::[pFR69]::[pRF93]

The riboflavin producing strain RB50::[pRF69] is a genetically modified strain of B. subtilis. RB50 refers to the host strain of B. subtilis, which contains several mutations introduced to improve production of nucleotides and riboflavin. pRF69 refers to a rib operon modified by the introduction of strong phage promoters which was introduced at the rib locus of pRF50. The modified operon pRF69 can be amplified to high copy numbers. A detailed description of the strain RB50::[pRF69] is presented above. To further increase the number of rib operons, a second plasmid with a modified rib operon and a tetracycline resistance gene was introduced at the bpr locus (essentially as described in example 8, second site integration). This second plasmid, pRF93, was constructed from pRF89 (FIG. 14) by replacing the chloramphenicol resistance gene by a tetracyclin resistance gene (Example 8, second site integration). The resulting strain is RB 50::[pRF69]$_n$::[pRF93]$_m$ (n and m refer to the copy numbers of the modified operons).

Example 11
Cloning Vectors pDSNdeHis, pXI12 and pXI16

NdeI is a restriction enzyme with a 6 bp recognition site ending with ATG. It is therefore the enzyme of choice for the cloning of open reading frames (ORFs) which generally begin with1 the translation start codon ATG. The vectors pDSNdeHis, pXI12 and pXI16 all contain an NdeI cloning site. In the pXI vectors, the ATG of the NdeI site was positioned such that it corresponds to the translational start codon, whereas in pDSNdeHis, a histidine-tag is added at the amino-terminus of the expressed protein (see below).

Figures 19A, 19B:
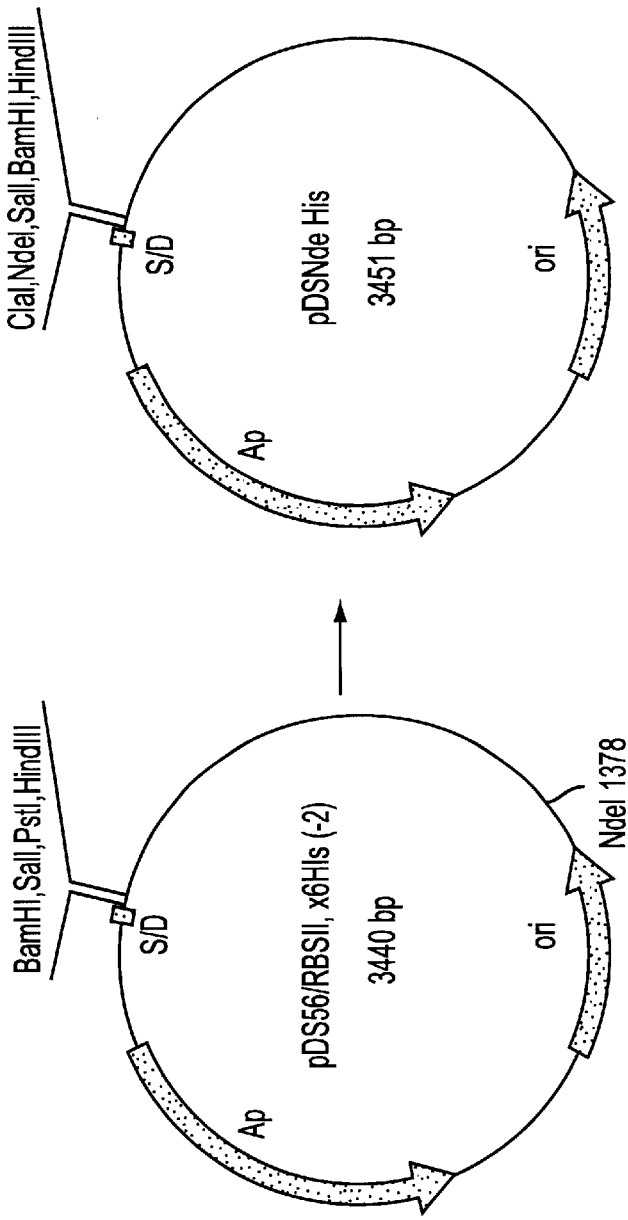
FIG. 19 (Parts A–B): The expression vector pDSNdeHis. A: construction of pDSNdeHis from the parent vector pDS/RBSII, 6xHis(-2). The existing NdeI site was eliminated by cutting, filling in of the sticky ends and religating. The resulting plasmid was cut with BamHI and HindIII and a synthetic poly-linker containing the restriction sites ClaI, NdeI, SalI, BamHI and HindIII was introduced. B: The sequence of pDSNdeHis from the Shine-Delgarno sequence (S/D box) to the multiple cloning sites and the peptide with the consecutive histidine residues for purification of recombinant proteins are shown (SEQ ID NO. 228).

Construction of pDSNdeHis The expression vector pDS/RBSII, 6×His(−2) (Stuiber, D., Matile, H. and Garotta, G., 1990. System for high-level production in *Escherichia coli* and rapid purification of recombinant proteins: application to epitope mapping, preparation of antibodies and structure-function analysis. Immunol. Meth. vol. IV, p. 121–152) was used as parent plasmid for the construction of pDSNdeHis. pDS/RBSII, 6×His(−2) is identical to pDS/RBSII, 6 His (Stulber et al. 1990; see also Accession No. DSM 5298) except for an additional G nucleotide in front of the BamHI site. An existing NdeI site in a non-essential region of the plasmid was eliminated by cutting, filling-in of the sticky ends and religating. The resulting plasmid was cut with BamHI and HindIII and a polylinker carrying sites for the restriction endonucleases ClaI, NdeI, SalI, BamHI and HindIII was introduced (FIG. 19). The proteins expressed from this vector possess an N-terminal extension containing six consecutive histidine residues which permit a one step purification (Stiber et al., 1990).

Figure 20:
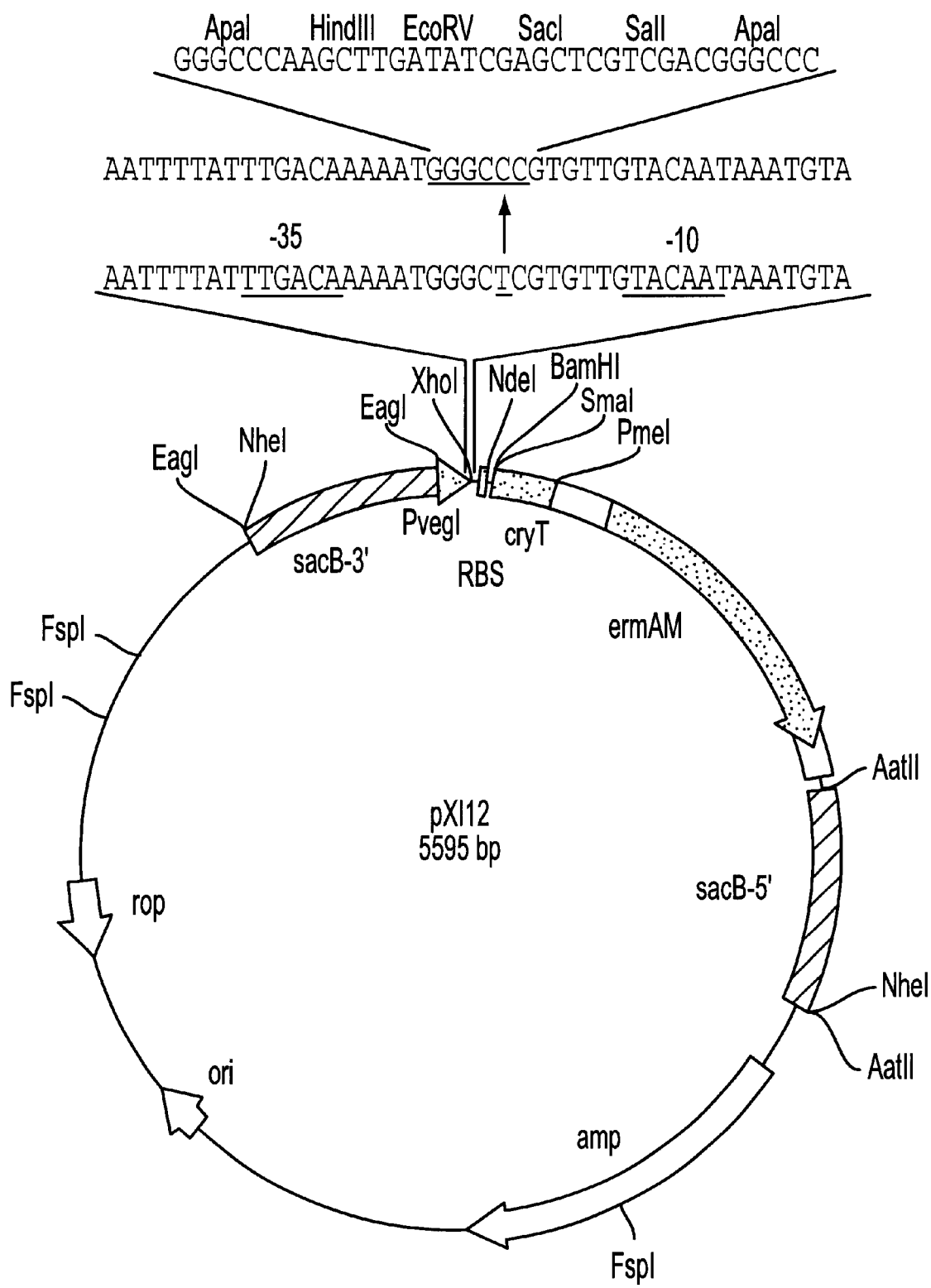
FIG. 20: Plasmids pXI12 and pXI16. The plasmid pXI12 is represented by a circle. The recognition sites for some restriction enzymes are indicated by standard abbreviations. The important elements of the vector are labelled as follows: PvegI: medium strenght, constitutive promoter from *B. subtilis*; RBS: synthetic ribosome binding site; cryT: transcriptional terminator from *B. thuringiensis*; ermAM: constitutively expressed erythromycin resistance gene; sacB-3' and sacB-5': homology regions for integration via homologous recombination, derived from the levansucrase gene of *B. subtilis*; amp: ampicillin resistance gene from pBR322; ori: origin of replication from pBR322; rop: rop gene from pBR322. The direction of some of the elements is indicated by arrows. Above the plasmid, the promoter with the −35 and −10 regions is shown. The arrow points to the T to C mutation which was introduced to create the ApaI site (box in middle line) in pXI16. The uppermost line shows the promoter interrupting sequence of pXI16 and the introduced restriction sites which is represented by SEQ ID NO. 229.

Construction of pXI12 (FIG. 20)

Figure 22A:
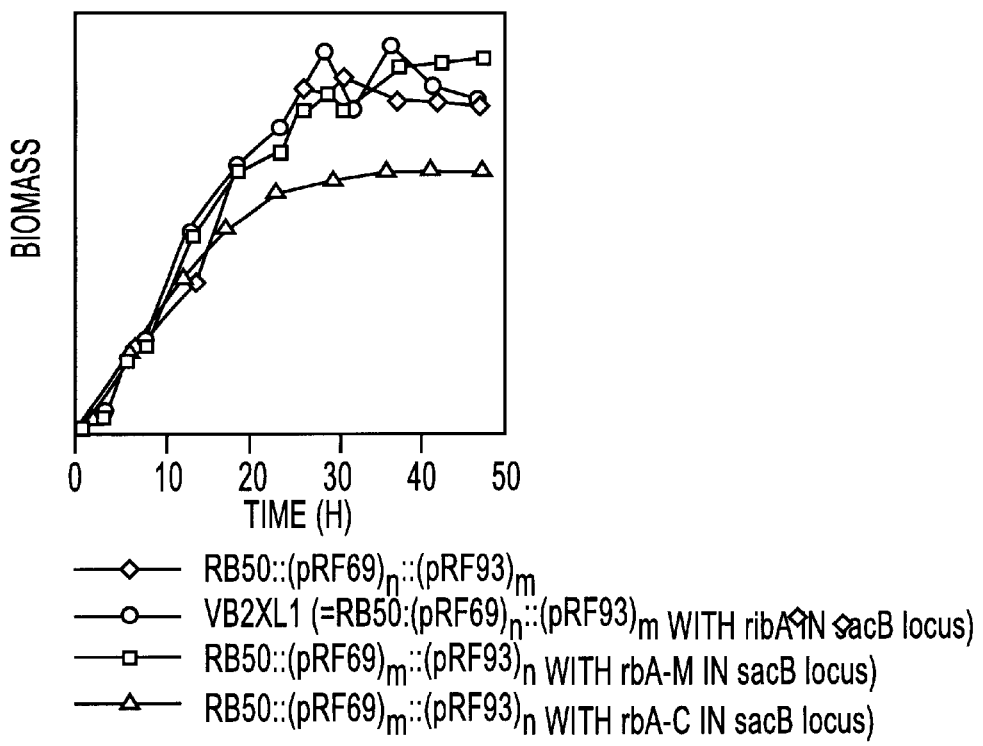
FIG. 22 (Parts A–B). Effect of the introduction of a ribA, ribA-M or ribA-C gene into the sacB locus of RB$^{50}$::(pRF69)$_n$::(pRF93)$_m$ on cell growth and riboflavin production. Fermentations were carried out with RB50::(pRF69)$_n$::(pRF93)$_m$ or its derivatives having the mutase encoding half of ribA (ribA-M), the cyclohydrolase II encoding half of ribA (ribA-C) or the entire ribA inserted in the sacB locus. The modified operons pRF69 and pRF93 of all strains were amplified. Panel A shows the OD$_{540}$ values of samples taken during the fermentations and the corresponding riboflavin titers are plotted in panel B.
Figure 22B:
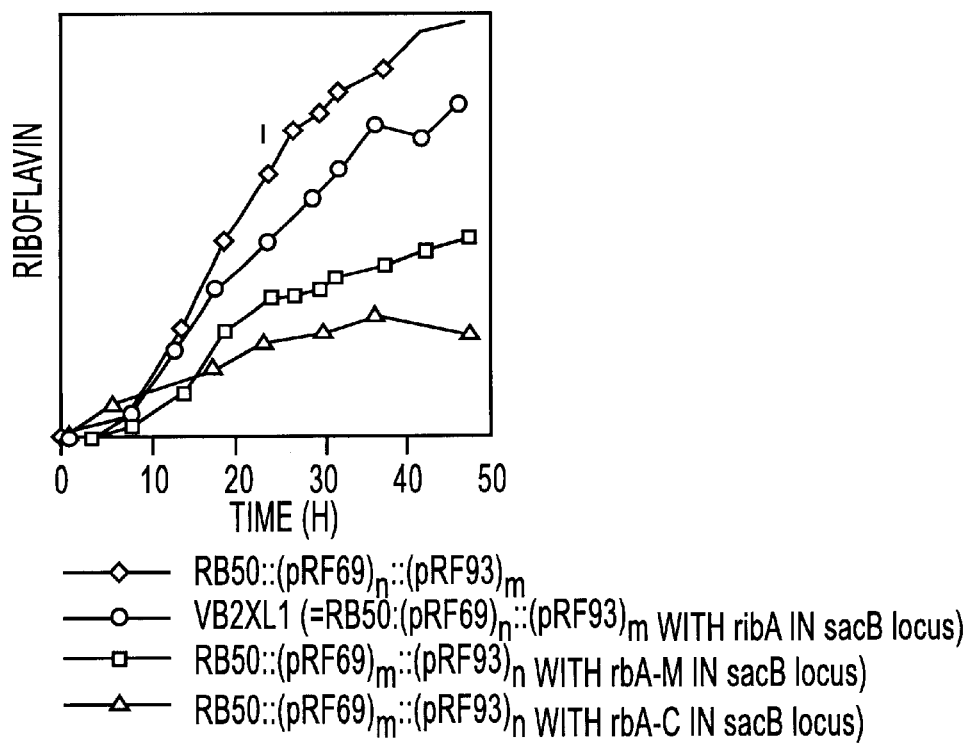

The backbone of the vector is the EagI-AatII fragment of pBR322 containing the ampicillin resistance gene, the origin of replication and the rop gene (Bolivar, F., Rodriguez, R. L., Greene, P. J., Betlach, M. C., Heynecker, H. L., Boyer, H. W., Crosa, J. H. and Falkow, S., 1977. Construction and characterization of new cloning vehicles. II. A multipurpose cloning system. Gene 2, 95–113). The pBR322 sequence is flanked by two sequences derived from the levansucrase gene (sacB) of *B. subtilis* which were obtained by polymerase chain reaction (PCR). The recognition sites for the restriction endonucleases AatII, EagI and NheI (FIG. 22) were introduced through the PCR primers. The sacB-5' sequence starts at position 729 of the levansucrase sequence (database accession number X02730 of the Genebank database or the database of the European Bioinformatics Institute, Hinxton Hall, Cambridge, GB) and ends at position 1266. The sacB-3' fragment includes the sequence between positions 1336 and 1794. As a selectable marker the erythromycine resistance gene ermAM from the plasmid pAMβ1 (accession number Y00116 of the Genebank database or the database of the European Bioinformatics Institute, Hinxton Hall, Cambridge, GB) was introduced. The sequence, also obtained by PCR, starts at position 107 of the sequence with the accession number Y00116 and ends at position 1091. The flanking AatII and PmeI sites originate from the PCR primers. The promoter driving the transcription of the cloned gene is the medium strength, constitutive vegI promoter from *B. subtilis* and corresponds to positions 30 to 101 of the published sequence (accession number J01552 of the Genebank database or the database of the European Bioinformatics Institute, Hinxton Hall, Cambridge, GB). The restriction sites EagI and XhoI which flank the promoter originate from the PCR primers. The cryT transcriptional terminator is from *B. thuringiensis* and corresponds to positions 268 to 380 of the sequence in accession number M13201 of the Genebank database or the database of the European Bioinformatics Institute, Hinxton Hall, Cambridge, GB. Again, the flanking PmeI and SmaI sites are primer derived. The ribosome binding site (underlined) and the polylinker stretch including the translational start site within the NdeI site (bold) was introduced as synthetic DNA with the sequence CTCGAGAA*TTAAAG-GAGGG*TTTCATATGAATTCGGATCCCGGG. (SEQ ID NO. 234) The sequences at the joints of the various elements are shown in table IX. The sequence shown in table IX column 1, line 1 is SEQ ID NO. 235. The sequence shown in table IX column 1, line 2 is SEQ ID NO. 236. The sequence shown in table IX column 1, line 3 is SEQ ID NO. 237. The sequence shown in table IX column 1, line 4 is SEQ ID NO. 238. The sequence shown in table IX column 1, line 5 is SEQ ID NO. 239. The sequence shown in table IX column 1, line 6 is SEQ ID NO. 240. The sequence shown in table IX column 1, line 7 is SEQ ID NO. 241. The sequence shown in table DC column 2, line 5 is SEQ ID NO. 242. The sequence shown in table IX column 2, lne 6 is SEQ ID NO. 243. The sequence shown in table IX column 3, fine 1 is SEQ ID NO. 244. The sequence shown in table IX column 3, line 2 is SEQ ID NO. 245. The sequence shown in table IX column 3, line 3 is SEQ ID NO. 246. The sequence shown in table IX column 3, line 4 is SEQ ID NO. 247. The sequence shown in table IX column 3, line 5 is SEQ ID NO. 248. The sequence shown in table I column 3, line 6 is SEQ ID NO. 249. The sequence shown in table IX column 3, fine 7 is SEQ ID NO. 250.

Construction of pXI16

The expression of the genes cloned in pXI12 might not be tolerated in *E. coli*. To avoid potential problems, a variant of pXI12 was created in which the veg promoter is interrupted by a short sequence. To construct this modified vector, named pXI16, a point mutation was introduced between the −35 and the −10 regions of the veg promoter to create an ApaI site and a 30 bp polylinker was then introduced (FIG. 20).

Example 12

Cloning of the ribA gene

The ribA gene was isolated from plasmid pRF2 (FIG. 6) with polymerase chain reaction (PCR) using the primers ribA5 and ribA3. This approach allowed the introduction of an NdeI restriction endonuclease site site at the start codon of the gene and a BambI site after the stop codon. The primers had the following sequence:

```
ribA5   5'GAAGATTcatATGTTTCATC    (SEQ ID NO.251)

ribA3   5'TATggaTccTTAGAAATGAA    (SEQ ID NO.252)
```

The underlined sequences correspond to the restriction endonuclease sites NdeI (CATATG) and BamHI (GGATCC), small caps indicate changed nucleotides as compared to the sequence of the *B. subtilis* rib operon and bold sequences mark the translational start codon (ATG) and the reverse complement of the stop codon (TTA).

The GeneAmp DNA amplification reagent kit from Perkin Elmer Cetus was used for PCR reactions following the instructions of the manufacturer. Reaction conditions were: 1 min 94° C., 1 min 45° C. and 2 min 72° C. for 25 cycles. The concentration of each primer was 1 $\mu$M and the template DNA was added at a concentration of about 1 pM. The PCR reaction product was separated from the primers by agarose gel electrophoresis and the PCR fragment containing ribA was isolated (Heery, D. M., Gannon, F. and Powell, R., 1990. A simple method for subcloning DNA fragments from gel slices. Trends in Genetics 6, 173; Vaux, D. L., 1992. Rapid recovery of DNA from agarose gels. Trends in Genetics 8, 81), cut with NdeI and BamHI and cloned into the vector pDSNdeHis, resulting in the plasmid pDSribA.

Example 13
Construction of the Strain VB2XL1

Figure 21:
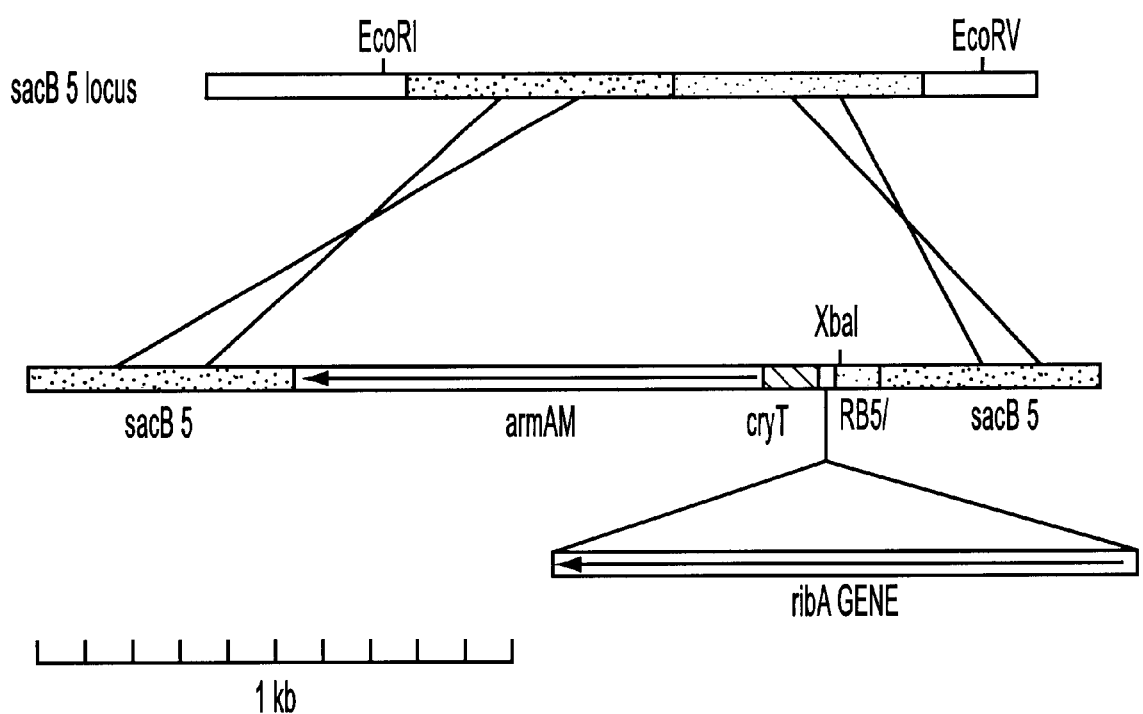
FIG. 21: Integration of the ribA gene into the sacB locus of *B. subtilis*. The sacB locus is schematically shown in the upper part. The sites for the restriction endonucleases EcoRI and EcoRV are indicated. The homology regions present in the pXI clones are represented as shaded boxes. The lower part shows the linearized pXI plasmid without the pBR322 derived section and the ribA gene cloned between the NdeI and BamHI sites. The integration of the pXI derived DNA via double cross-over is indicated.

The ribA gene was excised from pDSribA with NdeI and BamHI and subcloned into the NdeI-BamHI cleaved pXI16. After isolation of the plasmid from *E. coli* the DNA was cut with ApaI, the 30 bp insert was deleted and the veg promoter was reconstituted by ligation. The plasmid was then linearised by cutting with FspI which cleaves only in the pBR322 derived sequence (FIG. 20) and the cloned gene was introduced into transformation-competent *B. subtilis* cells following the described two-step procedure (Cutting, S. M. and Vander Horn, P. B., 1990. In: Molecular biological methods for Bacillus (Harwood and Cutting, eds.), p. 67–71, John Wiley & Sons Ltd., Chichester, England). Since the production strain RB50::[pRF69]::[pRF93] cannot be made competent for transformation *B. subtilis* strain 1012 (Saito, H., Shibata, T. and Ando, T., 1979. Mapping of genes determining nonpermissiveness and host-specific restriction to bacteriophages in *Bacillus subtilis* Marburg. Mol. Gen. Genet. 170, 117–122) was chosen as an intermediate host. Erythromycin resistant clones had the ribA gene and the erythromycin-resistance gene erMAM, inserted in the sacB locus by double cross-over in the homology regions sacB-3' and sacB-5' (FIG. 21). The modified sacB locus was then introduced into RB50::[pRF69]::[pRF93] by transduction with the phage PBS1 according to the liquid culture method as described (Cutting and Vander Horn, 1990).

Example 14
Construction of RB50::[pFR69]::[pRF93] Strains With ribA-M or ribA-C in the sacB Locus RibA encodes two enzymatic activities, the GTP cyclohydrolase II and the mutase (3,4-dihydroxy-2-butanone 4-phosphate synthase), which are encoded by two separate genes in *E. coli* (Richter, G., Ritz, H., Katzenmeier, G., Volk, R., Kohnle, A., Lottspeich, F., Allendorf, D. and Bacher, A., 1993. Biosynthesis of riboflavin: cloning, sequencing, mapping and expression of the gene coding for GTP cyclohydrolase II of *Escherichia coli*. J. Bact. 175, 4045–4051). The mutase activity is located in the amninoterminal half of the *B. subtilis* ribA and the GTP cyclohydrolase II activity resides in the carboxyterminal half. The mutase encoding portion of ribA, named ribA-M, was excised from pDSribA with NdeI and HincII and cloned into the NdeI and SmaI cleaved pXI16 vector. The single HincII site is conveniently located in the middle of ribA and cleavage occurs between two codons separating the two activities encoding halfs of the gene. The introduction of ribA-M into the sacB locus of RB50::[pRF69]::[pRF93] was done as described above. The GTP cyclohydrolase encoding portion of ribA, named ribA-C, was excised from pDSribA with HincII and BamHI and introduced into the HincII-BamHI cleaved pDSNdeHis. Note that the single HincII recognition site in pDSNdeHis is the same as the SalI site (GTCGAC, FIG. 19) and HincII cleavage results in a blunt end cut through the middle of the recognition site. The resulting plasmid was then cut with NdeI and BamHI and ribA-C was cloned into the NdeI BamHI cut pXI12. The introduction of ribA-C into the sacB locus of RB50:: [pRF69]::[pRF93] was done as described above except that the ApaI cleavage and religation step was omitted, since pXI12 with an uninterrupted veg promoter was used (FIG. 20).

Example 15
Amplification of the Modified Operons pRF69 and pRF93

Amplification of the modified operons is important for high riboflavin titers. The following amplification scheme was used: 30 µl of an overnight culture grown in VY (25 g/L veal infusion broth (Difco), 5 g/L yeast extract, 15 g/L glucose) with 20 4µg/ml tetracycline and 10 µg/ml chloramphenicol were used to inoculate three tubes containing 3 ml VY and 30, 60 or 75 µg/ml tetracycline. After 8–9 hours at 37° C. and 200 rpm, 30–50 µl of the culture with the highest tetracycline concentration still resulting in good growth was used to inoculate tubes containing 3 ml VY and 30, 45 or 60 µg/ml chloramphenicol. After overnight incubation at 37° C. and 200 rpm, 30–50 µl of the culture with the highest chloramphenicol concentration still resulting in good growth was used to inoculate tubes containing 3 ml VY and 60, 75, 90 or 120 µg/ml tetracycline. In the same manner growth continued in VY with 45, 60 or 80 µg/ml chloramphenicol, VY with 75, 90, 120 or 140 µg/ml tetracycline and VY with 60 or 80 µg/ml chloramphenicol. The last transfer was with 200 µl into two tubes containing 15 ml VY and 120 or 140 µg/ml tetracycline. The cells were grown to an $OD_{600}$ of about 0.8 and then distributed into 1 ml aliquots. Glycerol was added to a final concentration of 15% and the cells were stored at −70° C. The strain VB2XL1 reached the maximal antibiotic concentrations of 140 µg/ml tetracycline and 80 µg/ml chloramphenicol.

Fermentative Production of Riboflavin

Fermentative production of riboflavin was done by using the trans-formed *B.subtilis* strains as described above in glucose limited feedbatch as described hereinbelow. In general, bacteria that are prototrophic for riboflavin survive on minimal medium in the absence of riboflavin. Production of riboflavin can be detected and quantified by various methods. In a preferred embodiment, overproduction of riboflavin is readily observed when overproducing bacteria are exposed to UV light at 366 nm, as described infra, producing an observable, yellow fluorescence. For example, many of the engineered plasmids of the present invention are produced in *E. coli*. For some of these plasmids, overproduction of riboflavin has been confirmed by this method. The amount of riboflavin produced can be quantitated, e.g., with reverse-phase high performance liquid chromatography (HPLC). Cell-free supernatants from bacteria can be fractionated over an HPLC column, as described infra, and monitored for riboflavin at 254 nm. By extrapolation from a standard curve, the concentration of riboflavin can be determined by the area of the peak on the chromatogram.

Riboflavin can also be quantitated by fluorescence spectrophotometry. For example, samples containing riboflavin can be read in a fluorescence spectrophotometer set at an emission wavelength of 525 nm and an excitation wavelength of 450 nm.

In addition, other methods known in the art are available to detect or quantitate riboflavin based on its physical and biological properties.

Fermentation

Riboflavin overproducing bacteria can be grown in vessels ranging from shake flasks to large "batch" fermentors, by methods known in the art (see below). In a preferred embodiment, nutrient feed can be manipulated to maximize riboflavin production at the minimum cost by varying the nutrients in the medium.

In a specific embodiment, amplified bcontaining genes can be maintained at high-copy number in the bacterial chromosome by the inclusion of about 60 µg/ml chloramphenicol in the inoculum seed strain (but not necessarily in the fermentor). Chemap 14-liter fermentors can be used at 1000 rpm with a head pressure of 0.6 atmospheres.

The cells (especially recombinant bacteria as specifically mentioned herein) are grown under suitable growth conditions. Such suitable growth conditions are characterized by limiting the availability of a component of the growth medium and/or feed medium in such a way that aerobic conditions for the growth of said recombinant bacterium are maintained. Such conditions can be also characterized e.g. by maintaining a level of dissolved oxygen at a concentration between about 5% to 30%. One skilled in the art is familiar with the fact that such levels of dissolved oxygen can vary dependent on the specific technical equipment used for growing said recombinant bacteria and for measuring said dissolved oxygen concentration. Under anaerobic conditions the synthesis of riboflavin is reduced. In some embodiments, the limiting component is chosen from a carbon source, nitrogen source, or a component required by the cells (e.g., in the feed medium). For example, if the cells are auxotrophic, for example, for methionine, a limiting level of methionine may be provided in the growth medium. In another example, such component could be glucose or a carbonic acid, e.g. a citric acid cycle acid, such as citric acid or succinic acid, or an amino acid.

Example 16

Fourth Site Integration

The strain VB2XL3 is generically identical to VB2XL1 except that an additional ribA gene was introduced in the amyE locus to further increase the ribA level. VB2XL3 was constructed basically as described above for VB2XL1. In brief, the erythromycin marker in pXI6 (FIG. 20) was replaced by a neomycin resistance gene and the sacB homology regions were replaced by amyE homology sequences resulting in the vector pXI191. The neomycin resistance gene was obtained from the plasmid pBEST501 (M. Itaya et al., Nucl. Acids Res., 1989, p. 4410) and the inherent ApaI site was eliminated by a silent point mutation. The amyE homology regions were amplified with PCR from the *B. subtilis* genome with primers which were designed according to the known sequence (Accession number X02150). The ribA gene was then cloned in pXI191 and the resulting plasmid was used as a vehicle to introduce the ribA gene into the amyE locus of VB2XL1 essentially as described above. The new strain was named VB2XL3.

TABLE IX

Sequence in pXI12 at the joints of the various elements.

| sequence function and origin | synthetic linker | sequence function and origin |
|---|---|---|
| Pveg(Ac# J01552)* pos. 101<br>\|<br>AAATGTAGTG | XhoI<br>\|<br>CTCGAG | RBS snd polylinker (synthetic)<br>\|<br>AATTAAAGGA |
| RBS and polylinker (synthetic)<br>\|<br>GAATTCGGAT | SmaI<br>CCCGGG | pos. 268 cryT (Ac# M13201)<br>\|<br>TCCAAGAGCA |
| cryT (Ac# M13201) pos.380<br>\|<br>GTAATACATA | PmeI<br>GGTTTAAAC | pos. 107 ermAM (Ac# Y00116)<br>\|<br>AGCAAAGAAT |
| ermAM (Ac# Y00116) pos. 1091<br>\|<br>GCTTCCAAGG | AatII<br>GACGTC | pos. 1266 aacB-5' (Ac#X02730)<br>\|<br>TCAGTTCCAG |
| sacB-5'(Ac#X02730) pos. 729<br>\|<br>TTTTGTAATG | NheI + AatII<br>GCTAGCGACGTC | pos. 4283 pBR322(Ac#J01749)<br>\|<br>AGGTGGCACT |
| pBR322 (Ac#J01749) pos. 945<br>\|<br>CCCAGCGCGT | EagI + NheI<br>CGGCCGCTAGC | pos. 1794 sacB-3'(Ac#X02730)<br>\|<br>GCAAACGTTG |
| sacB-3'(Ac#X02730) pos. 1336<br>\|<br>ACTTTCTTGA | EagI<br>CGGCCG | pos. 30 Pveg (Ac#J01552)<br>\|<br>GTCTTATTAA |

*Ac#: GenBank (release 93.0) or EMBL database (release 46.0) accession numbers

SEQUENCE LISTING

<160> NUMBER OF SEQ ID NOS: 252

<210> SEQ ID NO 1
<211> LENGTH: 5567
<212> TYPE: DNA
<213> ORGANISM: Bacillus subtilis

<400> SEQUENCE: 1
ctgcaggtcg actctagagg atcccccatg gacagccgta acggccttgg cctcttcacg      60
aaaaaacaaa ttgcgggtac gtcaaagttt gttttctacc cgtttaacga aatgcgcaaa     120

-continued

```
acaaattagg atcaagcagc ttcccattgg ggctgctttt tttatatctt ttttacggtc    180
atcccctaaa aacagaacat aaattcgtat atctatagaa aagaaatttt tgcagaaatg    240
tgaaacatat tcccgttatg catcgttata ttaataattt acgagaattt acggtttttt    300
attcatgaaa aaaggaata actcatatga atgaatagat tcatattggc tggaggttta    360
gaaatgggaa gaataaaaac caagattacc attctgttag tgcttttgct tttacttgca    420
ggcggttata tgtacataaa tgatattgag ctgaaggatg ttccgacagc aattggacaa    480
accttgtcct cggaagaaga ggaatacacc atccaggaat ataaagtgac gaaaattgac    540
ggctcagagt atcatggagt agcagaaaac ggaacgaaaa tcatcttcaa cggaaaaaaa    600
ttaaatcagg atttatctga tataaaagaa ggtgacaaga ttaaggctta cttcagcaaa    660
tcaaagcgga tcgacggtta atcaaggttg caaagtgaa tgattaaaaa acatcacctt    720
tcggatcgaa gggtgatgtt ttgttttttct caaattgtaa gtttatttca ttgcgtactt    780
taaaaggat cgctataata accaataagg acaaatgaat aaagattgta tccttcgggg    840
cagggtggaa atcccgaccg gcggtagtaa agcacatttg cttagagcc cgtgacccgt    900
gtgcataagc acgcggtgga ttcagtttaa gctgaagccg acagtgaaag tctggatggg    960
agaaggatga tgagccgcta tgcaaaatgt ttaaaaatgc atagtgttat ttcctattgc   1020
gtaaaatacc taaagccccg aatttttttat aaattcgggg cttttttgac ggtaaataac   1080
aaaagagggg agggaaacaa atggaagagt attatatgaa gctggcctta gatcttgcga   1140
agcagggcga aggacagacc gaatccaatc cgctcgtcgg cgctgttgtc gtaaaggacg   1200
gacaaattgt cggaatgggc gcccatttaa aatatggtga agctcatgca gaagttcatg   1260
ccatccatat ggctggagca catgcagagg gtgccgacat ttacgttaca ctcgaaccgt   1320
gcagccatta cggaaaaaca ccgccatgtg cagaattgat tatcaactct ggtatcaaaa   1380
gagtgttcgt ggcgatgaga gatcctaatc cgcttgtggc tggaagaggg atcagcatga   1440
tgaaagaagc tggcattgag gtaagggaag gcatcctggc agaccaggcg gagaggctga   1500
atgaaaaatt tctgcacttt atgaggacag gccttccgta cgtcacgcta aaagcggctg   1560
ccagccttga cggcaagata gctaccagca cgggtgacag caaatggatc acgtcagagg   1620
ctgcaagaca ggatgctcag caatacagga aaacacacca aagcatttta gtcggagttg   1680
gcacagtgaa agccgacaat ccgagcttaa cctgcagact gccgaatgta acaaaacagc   1740
cggttcgggt catacttgat accgtactct cgattcctga ggacgctaaa gtgatttgcg   1800
atcaaatagc gccgacatgg atttttacga cggcacgcgc agacgaggaa aagaaaaaac   1860
ggctttcagc tttcggagtg aacatattta cacttgaaac cgagcgcatt caaattcctg   1920
atgttttgaa gatcctagcg gaagaaggca tcatgtcggt gtatgtggaa ggcggttcag   1980
ctgttcacgg aagctttgtc aaagaaggct gttttcaaga aatcatcttc tattttgccc   2040
ctaaactaat cggaggaacg catgctccca gcttaatctc cggtgaaggt tttcaatcaa   2100
tgaaagatgt cccctattta caattcactg atataaccca atcggccgt gatatcaaac   2160
tgacggcaaa accgacaaag gaataggatg gtgaccatgt ttacaggaat tatcgaagaa   2220
acaggcacaa tcgaatccat gaaaaagca gggcatgcaa tggccttaac tattaaatgc   2280
tcaaagattt tagaggatgt tcatcttggc gacagcattg cagtgaacgg catttgtctg   2340
actgtcactg atttttacaaa aaatcaattc acagtggatg ttatgcctga aacagtcaaa   2400
gctacgtcac tgaatgattt aacaaaagga agcaaagtaa atctggaaag agcgatggcg   2460
```

```
gcaaacggcc gtttcggagg ccatttcgtc tcaggccatg tcgacggaac tgcggaaatc    2520
acacgaattg aagagaaaag caacgcagtt tactatgatt taaaaatgga cccgtcatta    2580
acaaaaacat tggttttaaa gggatcaatt actgtggatg gcgtgagctt aaccatattc    2640
ggcctgacag aagacacagt gacgatctcc ttaataccgc atacgatcag cgaaacgatc    2700
ttttcagaaa aaacgatcgg ctctaaagtg aatatcgaat gcgatatgat cggaaaatat    2760
atgtatcgat ttttgcataa agccaatgaa ataagaccc aacaaaccat tacaaaagcc    2820
ttcttaagcg aaaacggctt ttagagagga agatttgcat gtttcatccg atagaagaag    2880
cactggacgc tttaaaaaaa ggcgaagtca tcatcgttgt agatgatgaa gacagagaaa    2940
atgaaggaga ctttgtggct cttgccgagc atgcaacgcc ggaagtcatt aactttatgg    3000
cgacacatgg gagaggactg atctgcacgc cgctcagtga ggaaatcgca gacaggcttg    3060
atcttcaccc tatggttgag cataatacag actctcacca cactgcattt accgtaagca    3120
tagaccatcg tgaaacgaag acaggtatca gcgctcaaga aagatctttt accgttcaag    3180
cattgctgga cagcaaatcc gtgccatctg atttttcagcg tccggggcac atttttccac    3240
tgattgcgaa aaaggaggt gtcctgaaaa gcgcgggcca tacagaagct gctgttgatc    3300
ttgctgaagc ttgcggatct ccaggagccg gcgtcatttg tgaaattatg aatgaagacg    3360
gaacgatggc gagagtgcct gagctcattg aaattgcgaa aaagcatcaa ttaaaaatga    3420
tcaccattaa ggatttgatt caataccgtt acaatctgac aacacttgtc gagcgtgaag    3480
ttgacattac gctgcctact gattttggga catttaaggt ttatggatac acaaatgagg    3540
tagatggaaa agagcatgtc gcatttgtga tgggagatgt gccgttcgga aagaaccgg    3600 tattggtccg ggtgcattca gaatgtctca caggtgacgt gtttggctct catcgctgtg    3660
attgcggacc gcagctgcac gccgcgctga accaaattgc cgcagaaggc cgtggagtgc    3720
tcctgtactt gcgccaagaa ggacgaggca tcggtttaat caataaatta aaagcttata    3780
agcttcagga acaaggctat gacaccgtag aagccaatga ggcgcttgga ttcttgccgg    3840
atcttcgcaa ctatgcatc ggagcacaaa ttttacgcga cctcggtgtc cggaatatga    3900
agcttttgac gaataatccg cgaaaaatcg caggccttga aggctacgga ctcagtattt    3960
cagaaagagt gccgcttcaa atggaggcga agaacacaca taaaaaatat ttgcaaacca    4020
aaatgaacaa gctaggtcat ttacttcatt tctaatcaca aatatcacaa aaaaggatgg    4080
gaatcatatg aatatcatac aaggaaattt agttggtaca ggtcttaaaa tcggaatcgt    4140
agtaggaaga tttaatgatt ttattacgag caagctgctg agcggagcag aagatgcgct    4200
gctcagacat ggcgtagaca caaatgacat tgatgtggct tgggttccag cgcatttga    4260 ataccgtttt gctgcgaaaa aaatggcgga acaaaaaaa tatgatgcta ttatcacatt    4320
gggcactgtc atcagaggcg caacgacaca ttacgattat gtctgcaatg aagctgcaaa    4380
aggcatcgcg caagcagcaa acactactgg tgtacctgtc atctttggaa ttgtaacaac    4440
tgaaaacatc gaacaggcta tcgagcgtgc cggcacaaaa gcgggcaaca aggtgtaga    4500 ttgtgctgtt tctgccattg aaatggcaaa tttaaaccgc tcatttgaat aatttgctga    4560
aaacagttta aaaatatggc gaaaatgata taatgtgaga aaacggatca cctattcgta    4620
tccgttaata gcagactgga catttggat atagagggt tttatgtta attcgttata    4680 aaaaatcgtt tgaaaagatt gcgatggggc ttctttcgtt tatgccgaat gaaaagacc    4740 ttaagcagct tcagcagaca attaaggact acgaaacgga tacagaccgc cagctctttc    4800
tttggaaaga ggacgaggat atcgtcggag caatcggagt cgaaaaaaag gattctgagg    4860
```

-continued

```
ttgagatccg gcatatcagt gtgaatcctt ctcatcgcca tcaaggaatc ggaaaacaga    4920
tgatggatgc tttaaagcat ttattcaaaa cgcaagtact ggttccaaat gaattaacgc    4980
agagcttttt cgaacgttgt caaggtcagc aggatcaaga catttcatac aataattaag    5040
cagaggctgt gatcagtctc tgctttttt tctgcgttct atttctttt cacgttcacg    5100 gatgacgtca gtccgatccc gcaaacggtg tttgtcgata agaaatatgt tgctgagtgc    5160
actgggctgc cccatgtat acttttttt cctgcattcg atcctgcatg cttcctccag    5220
tttctcatct ttgattggca gtaatgct tttataggga gagacggttt cgatttgttc    5280
gtaaaccgat tgcataagtt cgagcaaacg gccatgatca agccctaagt cttcgactgc    5340
ccggtgttct gcttgaagaa tccggatgct gttcgccatc agtcttttg ccccggctgt    5400 attctgcctt ctgtgatgat ataaagccac tgcaagctga ataaagccca cccaatagcg    5460
ttttcgtttc tttggcggat cttccttcca atattcttct aatatttcat ggcattcaaa    5520
ataatcccgt gtcgcatgaa actcaacgag ataatctata taagctt                   5567
```

<210> SEQ ID NO 2
<211> LENGTH: 42
<212> TYPE: PRT
<213> ORGANISM: Bacillus subtilis

<400> SEQUENCE: 2

Leu Gln Val Asp Ser Arg Gly Ser Pro Met Asp Ser Arg Asn Gly Leu
1               5                   10                  15

Gly Leu Phe Thr Lys Lys Gln Ile Ala Gly Thr Ser Lys Phe Val Phe
            20                  25                  30

Tyr Pro Phe Asn Glu Met Arg Lys Thr Asn
        35                  40

<210> SEQ ID NO 3
<211> LENGTH: 19
<212> TYPE: PRT
<213> ORGANISM: Bacillus subtilis

<400> SEQUENCE: 3

Asp Gln Ala Ala Ser His Trp Gly Cys Phe Phe Tyr Ile Phe Phe Thr
1               5                   10                  15

Val Ile Pro

<210> SEQ ID NO 4
<211> LENGTH: 17
<212> TYPE: PRT
<213> ORGANISM: Bacillus subtilis

<400> SEQUENCE: 4

Lys Gln Asn Ile Asn Ser Tyr Ile Tyr Arg Lys Glu Ile Phe Ala Glu
1               5                   10                  15

Met

<210> SEQ ID NO 5
<211> LENGTH: 25
<212> TYPE: PRT
<213> ORGANISM: Bacillus subtilis

<400> SEQUENCE: 5

Asn Ile Phe Pro Leu Cys Ile Val Ile Leu Ile Ile Tyr Glu Asn Leu
1               5                   10                  15

```
Arg Phe Phe Ile His Glu Lys Lys Glu
            20              25

<210> SEQ ID NO 6
<211> LENGTH: 116
<212> TYPE: PRT
<213> ORGANISM: Bacillus subtilis

<400> SEQUENCE: 6

Met Asn Arg Phe Ile Leu Ala Gly Gly Leu Glu Met Gly Arg Ile Lys
 1               5                  10                  15

Thr Lys Ile Thr Ile Leu Leu Val Leu Leu Leu Leu Ala Gly Gly
            20                  25                  30

Tyr Met Tyr Ile Asn Asp Ile Glu Leu Lys Asp Val Pro Thr Ala Ile
            35                  40                  45

Gly Gln Thr Leu Ser Ser Glu Glu Glu Tyr Thr Ile Gln Glu Tyr
        50                  55                  60

Lys Val Thr Lys Ile Asp Gly Ser Glu Tyr His Gly Val Ala Glu Asn
 65                  70                  75                  80

Gly Thr Lys Ile Ile Phe Asn Gly Lys Lys Leu Asn Gln Asp Leu Ser
                85                  90                  95

Asp Ile Lys Glu Gly Asp Lys Ile Lys Ala Tyr Phe Ser Lys Ser Lys
            100                 105                 110

Arg Ile Asp Gly
        115

<210> SEQ ID NO 7
<211> LENGTH: 5
<212> TYPE: PRT
<213> ORGANISM: Bacillus subtilis

<400> SEQUENCE: 7

Ser Arg Leu Gln Lys
 1               5

<210> SEQ ID NO 8
<211> LENGTH: 27
<212> TYPE: PRT
<213> ORGANISM: Bacillus subtilis

<400> SEQUENCE: 8

Met Ile Lys Lys His His Leu Ser Asp Arg Arg Val Met Phe Cys Phe
 1               5                  10                  15

Ser Gln Ile Val Ser Leu Phe His Cys Val Leu
            20                  25

<210> SEQ ID NO 9
<211> LENGTH: 4
<212> TYPE: PRT
<213> ORGANISM: Bacillus subtilis

<400> SEQUENCE: 9

Lys Gly Ser Leu
 1

<210> SEQ ID NO 10
<211> LENGTH: 6
<212> TYPE: PRT
<213> ORGANISM: Bacillus subtilis

<400> SEQUENCE: 10
```

```
Pro Ile Arg Thr Asn Glu
  1               5
```

<210> SEQ ID NO 11
<211> LENGTH: 14
<212> TYPE: PRT
<213> ORGANISM: Bacillus subtilis

<400> SEQUENCE: 11

```
Arg Leu Tyr Pro Ser Gly Gln Gly Gly Asn Pro Asp Arg Arg
  1               5                  10
```

<210> SEQ ID NO 12
<211> LENGTH: 19
<212> TYPE: PRT
<213> ORGANISM: Bacillus subtilis

<400> SEQUENCE: 12

```
Ser Thr Phe Ala Leu Glu Pro Val Thr Arg Val His Lys His Ala Val
  1               5                  10                  15

Asp Ser Val
```

<210> SEQ ID NO 13
<211> LENGTH: 62
<212> TYPE: PRT
<213> ORGANISM: Bacillus subtilis

<400> SEQUENCE: 13

```
Ala Glu Ala Asp Ser Glu Ser Leu Asp Gly Arg Arg Met Met Ser Arg
  1               5                  10                  15

Tyr Ala Lys Cys Leu Lys Met His Ser Val Ile Ser Tyr Cys Val Lys
                 20                  25                  30

Tyr Leu Lys Pro Arg Ile Phe Tyr Lys Phe Gly Ala Phe Leu Thr Val
            35                  40                  45

Asn Asn Lys Arg Gly Glu Gly Asn Lys Trp Lys Ser Ile Ile
        50                  55                  60
```

<210> SEQ ID NO 14
<211> LENGTH: 20
<212> TYPE: PRT
<213> ORGANISM: Bacillus subtilis

<400> SEQUENCE: 14

```
Ile Leu Arg Ser Arg Ala Lys Asp Arg Pro Asn Pro Ile Arg Ser Ser
  1               5                  10                  15

Ala Leu Leu Ser
            20
```

<210> SEQ ID NO 15
<211> LENGTH: 11
<212> TYPE: PRT
<213> ORGANISM: Bacillus subtilis

<400> SEQUENCE: 15

```
Arg Thr Asp Lys Leu Ser Glu Trp Ala Pro Ile
  1               5                  10
```

<210> SEQ ID NO 16
<211> LENGTH: 42
<212> TYPE: PRT
<213> ORGANISM: Bacillus subtilis

<400> SEQUENCE: 16

Asn Met Val Lys Leu Met Gln Lys Phe Met Pro Ser Ile Trp Leu Glu
 1               5                  10                  15

His Met Gln Arg Val Pro Thr Phe Thr Leu His Ser Asn Arg Ala Ala
            20                  25                  30

Ile Thr Glu Lys His Arg His Val Gln Asn
            35                  40

<210> SEQ ID NO 17
<211> LENGTH: 12
<212> TYPE: PRT
<213> ORGANISM: Bacillus subtilis

<400> SEQUENCE: 17

Leu Ser Thr Leu Val Ser Lys Glu Cys Ser Trp Arg
 1               5                  10

<210> SEQ ID NO 18
<211> LENGTH: 13
<212> TYPE: PRT
<213> ORGANISM: Bacillus subtilis

<400> SEQUENCE: 18

Glu Ile Leu Ile Arg Leu Trp Leu Glu Glu Gly Ser Ala
 1               5                  10

<210> SEQ ID NO 19
<211> LENGTH: 6
<212> TYPE: PRT
<213> ORGANISM: Bacillus subtilis

<400> SEQUENCE: 19

Lys Lys Leu Ala Leu Arg
 1               5

<210> SEQ ID NO 20
<211> LENGTH: 11
<212> TYPE: PRT
<213> ORGANISM: Bacillus subtilis

<400> SEQUENCE: 20

Gly Lys Ala Ser Trp Gln Thr Arg Arg Arg Gly
 1               5                  10

<210> SEQ ID NO 21
<211> LENGTH: 7
<212> TYPE: PRT
<213> ORGANISM: Bacillus subtilis

<400> SEQUENCE: 21

Met Lys Asn Phe Cys Thr Leu
 1               5

<210> SEQ ID NO 22
<211> LENGTH: 8
<212> TYPE: PRT
<213> ORGANISM: Bacillus subtilis

<400> SEQUENCE: 22

Gly Gln Ala Phe Arg Thr Ser Arg
 1               5

<210> SEQ ID NO 23
<211> LENGTH: 9

```
<212> TYPE: PRT
<213> ORGANISM: Bacillus subtilis

<400> SEQUENCE: 23

Lys Arg Leu Pro Ala Leu Thr Ala Arg
 1               5

<210> SEQ ID NO 24
<211> LENGTH: 29
<212> TYPE: PRT
<213> ORGANISM: Bacillus subtilis

<400> SEQUENCE: 24

Leu Pro Ala Arg Val Thr Ala Asn Gly Ser Arg Gln Arg Leu Gln Asp
 1               5                  10                  15

Arg Met Leu Ser Asn Thr Gly Lys His Thr Lys Ala Phe
            20                  25

<210> SEQ ID NO 25
<211> LENGTH: 5
<212> TYPE: PRT
<213> ORGANISM: Bacillus subtilis

<400> SEQUENCE: 25

Ser Glu Leu Ala Gln
 1               5

<210> SEQ ID NO 26
<211> LENGTH: 6
<212> TYPE: PRT
<213> ORGANISM: Bacillus subtilis

<400> SEQUENCE: 26

Lys Pro Thr Ile Arg Ala
 1               5

<210> SEQ ID NO 27
<211> LENGTH: 6
<212> TYPE: PRT
<213> ORGANISM: Bacillus subtilis

<400> SEQUENCE: 27

Pro Ala Asp Cys Arg Met
 1               5

<210> SEQ ID NO 28
<211> LENGTH: 20
<212> TYPE: PRT
<213> ORGANISM: Bacillus subtilis

<400> SEQUENCE: 28

Gln Asn Ser Arg Phe Gly Ser Tyr Leu Ile Pro Tyr Ser Arg Phe Leu
 1               5                  10                  15

Arg Thr Leu Lys
            20

<210> SEQ ID NO 29
<211> LENGTH: 4
<212> TYPE: PRT
<213> ORGANISM: Bacillus subtilis

<400> SEQUENCE: 29

Phe Ala Ile Lys
 1
```

<210> SEQ ID NO 30
<211> LENGTH: 23
<212> TYPE: PRT
<213> ORGANISM: Bacillus subtilis

<400> SEQUENCE: 30

Arg Arg His Gly Phe Leu Arg Arg His Ala Gln Thr Arg Lys Arg Lys
 1               5                  10                  15

Asn Gly Phe Gln Leu Ser Glu
            20

<210> SEQ ID NO 31
<211> LENGTH: 15
<212> TYPE: PRT
<213> ORGANISM: Bacillus subtilis

<400> SEQUENCE: 31

Thr Tyr Leu His Leu Lys Pro Ser Ala Phe Lys Phe Leu Met Phe
 1               5                  10                  15

<210> SEQ ID NO 32
<211> LENGTH: 36
<212> TYPE: PRT
<213> ORGANISM: Bacillus subtilis

<400> SEQUENCE: 32

Arg Lys Lys Ala Ser Cys Arg Cys Met Trp Lys Ala Val Gln Leu Phe
 1               5                  10                  15

Thr Glu Ala Leu Ser Lys Lys Ala Val Phe Lys Lys Ser Ser Ser Ile
            20                  25                  30

Leu Pro Leu Asn
        35

<210> SEQ ID NO 33
<211> LENGTH: 8
<212> TYPE: PRT
<213> ORGANISM: Bacillus subtilis

<400> SEQUENCE: 33

Ser Glu Glu Arg Met Leu Pro Ala
 1               5

<210> SEQ ID NO 34
<211> LENGTH: 8
<212> TYPE: PRT
<213> ORGANISM: Bacillus subtilis

<400> SEQUENCE: 34

Ser Pro Val Lys Val Phe Asn Gln
 1               5

<210> SEQ ID NO 35
<211> LENGTH: 10
<212> TYPE: PRT
<213> ORGANISM: Bacillus subtilis

<400> SEQUENCE: 35

Lys Met Ser Pro Tyr Tyr Asn Ser Leu Ile
 1               5                  10

<210> SEQ ID NO 36
<211> LENGTH: 8

```
<212> TYPE: PRT
<213> ORGANISM: Bacillus subtilis

<400> SEQUENCE: 36

Pro Lys Ser Ala Val Ile Ser Asn
 1               5

<210> SEQ ID NO 37
<211> LENGTH: 226
<212> TYPE: PRT
<213> ORGANISM: Bacillus subtilis

<400> SEQUENCE: 37

Arg Gln Asn Arg Gln Arg Asn Arg Met Val Thr Met Phe Thr Gly Ile
 1               5                  10                  15

Ile Glu Glu Thr Gly Thr Ile Glu Ser Met Lys Lys Ala Gly His Ala
            20                  25                  30

Met Ala Leu Thr Ile Lys Cys Ser Lys Ile Leu Glu Asp Val His Leu
        35                  40                  45

Gly Asp Ser Ile Ala Val Asn Gly Ile Cys Leu Thr Val Thr Asp Phe
    50                  55                  60

Thr Lys Asn Gln Phe Thr Val Asp Val Met Pro Glu Thr Val Lys Ala
65                  70                  75                  80

Thr Ser Leu Asn Asp Leu Thr Lys Gly Ser Lys Val Asn Leu Glu Arg
                85                  90                  95

Ala Met Ala Ala Asn Gly Arg Phe Gly Gly His Phe Val Ser Gly His
            100                 105                 110

Val Asp Gly Thr Ala Glu Ile Thr Arg Ile Glu Glu Lys Ser Asn Ala
        115                 120                 125

Val Tyr Tyr Asp Leu Lys Met Asp Pro Ser Leu Thr Lys Thr Leu Val
    130                 135                 140

Leu Lys Gly Ser Ile Thr Val Asp Gly Val Ser Leu Thr Ile Phe Gly
145                 150                 155                 160

Leu Thr Glu Asp Thr Val Thr Ile Ser Leu Ile Pro His Thr Ile Ser
                165                 170                 175

Glu Thr Ile Phe Ser Glu Lys Thr Ile Gly Ser Lys Val Asn Ile Glu
            180                 185                 190

Cys Asp Met Ile Gly Lys Tyr Met Tyr Arg Phe Leu His Lys Ala Asn
        195                 200                 205

Glu Asn Lys Thr Gln Gln Thr Ile Thr Lys Ala Phe Leu Ser Glu Asn
    210                 215                 220

Gly Phe
225

<210> SEQ ID NO 38
<211> LENGTH: 9
<212> TYPE: PRT
<213> ORGANISM: Bacillus subtilis

<400> SEQUENCE: 38

Arg Gly Arg Phe Ala Cys Phe Ile Arg
 1               5

<210> SEQ ID NO 39
<211> LENGTH: 6
<212> TYPE: PRT
<213> ORGANISM: Bacillus subtilis

<400> SEQUENCE: 39
```

```
Lys Lys His Trp Thr Leu
  1               5
```

<210> SEQ ID NO 40
<211> LENGTH: 8
<212> TYPE: PRT
<213> ORGANISM: Bacillus subtilis

<400> SEQUENCE: 40

```
Lys Lys Ala Lys Ser Ser Ser Leu
  1               5
```

<210> SEQ ID NO 41
<211> LENGTH: 32
<212> TYPE: PRT
<213> ORGANISM: Bacillus subtilis

<400> SEQUENCE: 41

```
Met Met Lys Thr Glu Lys Met Lys Glu Thr Leu Trp Leu Leu Pro Ser
  1               5                  10                  15

Met Gln Arg Arg Lys Ser Leu Thr Leu Trp Arg His Met Gly Glu Asp
             20                  25                  30
```

<210> SEQ ID NO 42
<211> LENGTH: 31
<212> TYPE: PRT
<213> ORGANISM: Bacillus subtilis

<400> SEQUENCE: 42

```
Ser Ala Arg Arg Ser Val Arg Lys Ser Gln Thr Gly Leu Ile Phe Thr
  1               5                  10                  15

Leu Trp Leu Ser Ile Ile Gln Thr Leu Thr Leu His Leu Pro
             20                  25                  30
```

<210> SEQ ID NO 43
<211> LENGTH: 39
<212> TYPE: PRT
<213> ORGANISM: Bacillus subtilis

<400> SEQUENCE: 43

```
Thr Ile Val Lys Arg Arg Gln Val Ser Ala Leu Lys Lys Asp Leu Leu
  1               5                  10                  15

Pro Phe Lys His Cys Trp Thr Ala Asn Pro Cys His Leu Ile Phe Ser
             20                  25                  30

Val Arg Gly Thr Phe Phe His
                 35
```

<210> SEQ ID NO 44
<211> LENGTH: 7
<212> TYPE: PRT
<213> ORGANISM: Bacillus subtilis

<400> SEQUENCE: 44

```
Leu Arg Lys Lys Glu Val Ser
  1               5
```

<210> SEQ ID NO 45
<211> LENGTH: 27
<212> TYPE: PRT
<213> ORGANISM: Bacillus subtilis

<400> SEQUENCE: 45

-continued

Lys Ala Arg Ala Ile Gln Lys Leu Leu Ile Leu Leu Lys Leu Ala
 1               5                  10                  15

Asp Leu Gln Glu Pro Ala Ser Phe Val Lys Leu
                20                  25

<210> SEQ ID NO 46
<211> LENGTH: 20
<212> TYPE: PRT
<213> ORGANISM: Bacillus subtilis

<400> SEQUENCE: 46

Met Lys Thr Glu Arg Trp Arg Glu Cys Leu Ser Ser Leu Lys Leu Arg
 1               5                  10                  15

Lys Ser Ile Asn
            20

<210> SEQ ID NO 47
<211> LENGTH: 5
<212> TYPE: PRT
<213> ORGANISM: Bacillus subtilis

<400> SEQUENCE: 47

Ser Pro Leu Arg Ile
 1               5

<210> SEQ ID NO 48
<211> LENGTH: 6
<212> TYPE: PRT
<213> ORGANISM: Bacillus subtilis

<400> SEQUENCE: 48

Phe Asn Thr Val Thr Ile
 1               5

<210> SEQ ID NO 49
<211> LENGTH: 27
<212> TYPE: PRT
<213> ORGANISM: Bacillus subtilis

<400> SEQUENCE: 49

Gln His Leu Ser Ser Val Lys Leu Thr Leu Arg Cys Leu Leu Ile Leu
 1               5                  10                  15

Gly His Leu Arg Phe Met Asp Thr Gln Met Arg
                20                  25

<210> SEQ ID NO 50
<211> LENGTH: 8
<212> TYPE: PRT
<213> ORGANISM: Bacillus subtilis

<400> SEQUENCE: 50

Met Glu Lys Ser Met Ser His Leu
 1               5

<210> SEQ ID NO 51
<211> LENGTH: 39
<212> TYPE: PRT
<213> ORGANISM: Bacillus subtilis

<400> SEQUENCE: 51

Trp Glu Met Cys Arg Ser Glu Lys Asn Arg Tyr Trp Ser Gly Cys Ile
 1               5                  10                  15

Gln Asn Val Ser Gln Val Thr Cys Leu Ala Leu Ile Ala Val Ile Ala

Asp Arg Ser Cys Thr Pro Arg
            35

<210> SEQ ID NO 52
<211> LENGTH: 22
<212> TYPE: PRT
<213> ORGANISM: Bacillus subtilis

<400> SEQUENCE: 52

Thr Lys Leu Pro Gln Lys Ala Val Glu Cys Ser Cys Thr Cys Ala Lys
 1               5                  10                  15

Lys Asp Glu Ala Ser Val
            20

<210> SEQ ID NO 53
<211> LENGTH: 12
<212> TYPE: PRT
<213> ORGANISM: Bacillus subtilis

<400> SEQUENCE: 53

Lys Leu Ile Ser Phe Arg Asn Lys Ala Met Thr Pro
 1               5                  10

<210> SEQ ID NO 54
<211> LENGTH: 29
<212> TYPE: PRT
<213> ORGANISM: Bacillus subtilis

<400> SEQUENCE: 54

Lys Pro Met Arg Arg Leu Asp Ser Cys Arg Ile Phe Ala Thr Met Ala
 1               5                  10                  15

Ser Glu His Lys Phe Tyr Ala Thr Ser Val Ser Gly Ile
            20                  25

<210> SEQ ID NO 55
<211> LENGTH: 38
<212> TYPE: PRT
<213> ORGANISM: Bacillus subtilis

<400> SEQUENCE: 55

Arg Ile Ile Arg Glu Lys Ser Gln Ala Leu Lys Ala Thr Asp Ser Val
 1               5                  10                  15

Phe Gln Lys Glu Cys Arg Phe Lys Trp Arg Arg Lys Asn Thr Ile Lys
            20                  25                  30

Asn Ile Cys Lys Pro Lys
            35

<210> SEQ ID NO 56
<211> LENGTH: 30
<212> TYPE: PRT
<213> ORGANISM: Bacillus subtilis

<400> SEQUENCE: 56

Val Ile Tyr Phe Ile Ser Asn His Lys Tyr His Lys Lys Gly Trp Glu
 1               5                  10                  15

Ser Tyr Glu Tyr His Thr Arg Lys Phe Ser Trp Tyr Arg Ser
            20                  25                  30

<210> SEQ ID NO 57
<211> LENGTH: 8
<212> TYPE: PRT

<213> ORGANISM: Bacillus subtilis

<400> SEQUENCE: 57

Asn Arg Asn Arg Ser Arg Lys Ile
 1               5

<210> SEQ ID NO 58
<211> LENGTH: 22
<212> TYPE: PRT
<213> ORGANISM: Bacillus subtilis

<400> SEQUENCE: 58

Phe Tyr Tyr Glu Gln Ala Ala Glu Arg Ser Arg Arg Cys Ala Ala Gln
 1               5                  10                  15

Thr Trp Arg Arg His Lys
            20

<210> SEQ ID NO 59
<211> LENGTH: 8
<212> TYPE: PRT
<213> ORGANISM: Bacillus subtilis

<400> SEQUENCE: 59

Cys Gly Leu Gly Ser Arg Arg Ile
 1               5

<210> SEQ ID NO 60
<211> LENGTH: 14
<212> TYPE: PRT
<213> ORGANISM: Bacillus subtilis

<400> SEQUENCE: 60

Asn Thr Val Cys Cys Glu Lys Asn Gly Gly Asn Lys Lys Ile
 1               5                  10

<210> SEQ ID NO 61
<211> LENGTH: 21
<212> TYPE: PRT
<213> ORGANISM: Bacillus subtilis

<400> SEQUENCE: 61

Cys Tyr Tyr His Ile Gly His Cys His Gln Arg Arg Asn Asp Thr Leu
 1               5                  10                  15

Arg Leu Cys Leu Gln
            20

<210> SEQ ID NO 62
<211> LENGTH: 23
<212> TYPE: PRT
<213> ORGANISM: Bacillus subtilis

<400> SEQUENCE: 62

Ser Cys Lys Arg His Arg Ala Ser Ser Lys His Tyr Trp Cys Thr Cys
 1               5                  10                  15

His Leu Trp Asn Cys Asn Asn
            20

<210> SEQ ID NO 63
<211> LENGTH: 25
<212> TYPE: PRT
<213> ORGANISM: Bacillus subtilis

<400> SEQUENCE: 63

```
Lys His Arg Thr Gly Tyr Arg Ala Cys Arg His Lys Ser Gly Gln Gln
 1               5                  10                  15

Arg Cys Arg Leu Cys Cys Phe Cys His
             20              25
```

<210> SEQ ID NO 64
<211> LENGTH: 8
<212> TYPE: PRT
<213> ORGANISM: Bacillus subtilis

<400> SEQUENCE: 64

```
Asn Gly Lys Phe Lys Pro Leu Ile
 1               5
```

<210> SEQ ID NO 65
<211> LENGTH: 10
<212> TYPE: PRT
<213> ORGANISM: Bacillus subtilis

<400> SEQUENCE: 65

```
Lys Gln Phe Lys Asn Met Ala Lys Met Ile
 1               5                  10
```

<210> SEQ ID NO 66
<211> LENGTH: 25
<212> TYPE: PRT
<213> ORGANISM: Bacillus subtilis

<400> SEQUENCE: 66

```
Cys Glu Lys Thr Asp His Leu Phe Val Ser Val Asn Ser Arg Leu Asp
 1               5                  10                  15

Ile Leu Asp Ile Glu Gly Phe Leu Cys
             20              25
```

<210> SEQ ID NO 67
<211> LENGTH: 70
<212> TYPE: PRT
<213> ORGANISM: Bacillus subtilis

<400> SEQUENCE: 67

```
Phe Val Ile Lys Asn Arg Leu Lys Arg Leu Arg Trp Gly Phe Phe Arg
 1               5                  10                  15

Leu Cys Arg Met Lys Lys Thr Leu Ser Ser Phe Ser Arg Gln Leu Arg
             20                  25                  30

Thr Thr Lys Arg Ile Gln Thr Ala Ser Ser Phe Phe Gly Lys Arg Thr
             35                  40                  45

Arg Ile Ser Ser Glu Gln Ser Gly Ser Lys Lys Arg Ile Leu Arg Leu
         50                  55                  60

Arg Ser Gly Ile Ser Val
 65                  70
```

<210> SEQ ID NO 68
<211> LENGTH: 12
<212> TYPE: PRT
<213> ORGANISM: Bacillus subtilis

<400> SEQUENCE: 68

```
Ile Leu Leu Ile Ala Ile Lys Glu Ser Glu Asn Arg
 1               5                  10
```

<210> SEQ ID NO 69
<211> LENGTH: 13

```
<212> TYPE: PRT
<213> ORGANISM: Bacillus subtilis

<400> SEQUENCE: 69

Ser Ile Tyr Ser Lys Arg Lys Tyr Trp Phe Gln Met Asn
 1               5                  10

<210> SEQ ID NO 70
<211> LENGTH: 24
<212> TYPE: PRT
<213> ORGANISM: Bacillus subtilis

<400> SEQUENCE: 70

Arg Arg Ala Phe Ser Asn Val Val Lys Val Ser Arg Ile Lys Thr Phe
 1               5                  10                  15

His Thr Ile Ile Lys Gln Arg Leu
                20

<210> SEQ ID NO 71
<211> LENGTH: 91
<212> TYPE: PRT
<213> ORGANISM: Bacillus subtilis

<400> SEQUENCE: 71

Ser Val Ser Ala Phe Phe Ser Ala Phe Tyr Phe Phe Phe Thr Phe Thr
 1               5                  10                  15

Asp Asp Val Ser Pro Ile Pro Gln Thr Val Phe Val Asp Lys Lys Tyr
                20                  25                  30

Val Ala Glu Cys Thr Gly Leu Pro Pro Cys Ile Leu Phe Phe Pro Ala
            35                  40                  45

Phe Asp Pro Ala Cys Phe Leu Gln Phe Leu Ile Phe Asp Trp Gln Tyr
        50                  55                  60

Asn Ala Phe Ile Gly Arg Asp Gly Phe Asp Leu Phe Val Asn Arg Leu
 65                 70                  75                  80

His Lys Phe Glu Gln Thr Ala Met Ile Lys Pro
                85                  90

<210> SEQ ID NO 72
<211> LENGTH: 31
<212> TYPE: PRT
<213> ORGANISM: Bacillus subtilis

<400> SEQUENCE: 72

Val Phe Asp Cys Pro Val Phe Cys Leu Lys Asn Pro Asp Ala Val Arg
 1               5                  10                  15

His Gln Ser Phe Cys Pro Gly Cys Ile Leu Pro Ser Val Met Ile
                20                  25                  30

<210> SEQ ID NO 73
<211> LENGTH: 25
<212> TYPE: PRT
<213> ORGANISM: Bacillus subtilis

<400> SEQUENCE: 73

Ser His Cys Lys Leu Asn Lys Ala His Pro Ile Ala Phe Ser Phe Leu
 1               5                  10                  15

Trp Arg Ile Phe Leu Pro Ile Phe Phe
                20                  25

<210> SEQ ID NO 74
<211> LENGTH: 21
```

-continued

```
<212> TYPE: PRT
<213> ORGANISM: Bacillus subtilis

<400> SEQUENCE: 74

Tyr Phe Met Ala Phe Lys Ile Ile Pro Cys Arg Met Lys Leu Asn Glu
  1               5                  10                  15

Ile Ile Tyr Ile Ser
            20

<210> SEQ ID NO 75
<211> LENGTH: 66
<212> TYPE: PRT
<213> ORGANISM: Bacillus subtilis

<400> SEQUENCE: 75

Cys Arg Ser Thr Leu Glu Asp Pro Pro Trp Thr Ala Val Thr Ala Leu
  1               5                  10                  15

Ala Ser Ser Arg Lys Asn Lys Leu Arg Val Arg Gln Ser Leu Phe Ser
             20                  25                  30

Thr Arg Leu Thr Lys Cys Ala Lys Gln Ile Arg Ile Lys Gln Leu Pro
         35                  40                  45

Ile Gly Ala Ala Phe Phe Ile Ser Phe Leu Arg Ser Ser Pro Lys Asn
     50                  55                  60

Arg Thr
 65

<210> SEQ ID NO 76
<211> LENGTH: 23
<212> TYPE: PRT
<213> ORGANISM: Bacillus subtilis

<400> SEQUENCE: 76

Ile Arg Ile Ser Ile Glu Lys Lys Phe Leu Gln Lys Cys Glu Thr Tyr
  1               5                  10                  15

Ser Arg Tyr Ala Ser Leu Tyr
            20

<210> SEQ ID NO 77
<211> LENGTH: 18
<212> TYPE: PRT
<213> ORGANISM: Bacillus subtilis

<400> SEQUENCE: 77

Phe Thr Arg Ile Tyr Gly Phe Leu Phe Met Lys Lys Arg Asn Asn Ser
  1               5                  10                  15

Tyr Glu

<210> SEQ ID NO 78
<211> LENGTH: 8
<212> TYPE: PRT
<213> ORGANISM: Bacillus subtilis

<400> SEQUENCE: 78

Ile Asp Ser Tyr Trp Leu Glu Val
  1               5

<210> SEQ ID NO 79
<211> LENGTH: 4
<212> TYPE: PRT
<213> ORGANISM: Bacillus subtilis

<400> SEQUENCE: 79
```

Lys Trp Glu Glu
 1

<210> SEQ ID NO 80
<211> LENGTH: 7
<212> TYPE: PRT
<213> ORGANISM: Bacillus subtilis

<400> SEQUENCE: 80

Lys Pro Arg Leu Pro Phe Cys
 1               5

<210> SEQ ID NO 81
<211> LENGTH: 12
<212> TYPE: PRT
<213> ORGANISM: Bacillus subtilis

<400> SEQUENCE: 81

Cys Phe Cys Phe Tyr Leu Gln Ala Val Ile Cys Thr
 1               5                  10

<210> SEQ ID NO 82
<211> LENGTH: 4
<212> TYPE: PRT
<213> ORGANISM: Bacillus subtilis

<400> SEQUENCE: 82

Met Ile Leu Ser
 1

<210> SEQ ID NO 83
<211> LENGTH: 24
<212> TYPE: PRT
<213> ORGANISM: Bacillus subtilis

<400> SEQUENCE: 83

Arg Met Phe Arg Gln Gln Leu Asp Lys Pro Cys Pro Arg Lys Lys Arg
 1               5                  10                  15

Asn Thr Pro Ser Arg Asn Ile Lys
             20

<210> SEQ ID NO 84
<211> LENGTH: 10
<212> TYPE: PRT
<213> ORGANISM: Bacillus subtilis

<400> SEQUENCE: 84

Arg Lys Leu Thr Ala Gln Ser Ile Met Glu
 1               5                  10

<210> SEQ ID NO 85
<211> LENGTH: 13
<212> TYPE: PRT
<213> ORGANISM: Bacillus subtilis

<400> SEQUENCE: 85

Gln Lys Thr Glu Arg Lys Ser Ser Ser Thr Glu Lys Asn
 1               5                  10

<210> SEQ ID NO 86
<211> LENGTH: 6
<212> TYPE: PRT
<213> ORGANISM: Bacillus subtilis

```
<400> SEQUENCE: 86

Ile Arg Ile Tyr Leu Ile
 1               5

<210> SEQ ID NO 87
<211> LENGTH: 25
<212> TYPE: PRT
<213> ORGANISM: Bacillus subtilis

<400> SEQUENCE: 87

Lys Lys Val Thr Arg Leu Arg Leu Thr Ser Ala Asn Gln Ser Gly Ser
 1               5                  10                  15

Thr Val Asn Gln Gly Cys Lys Ser Glu
            20                  25

<210> SEQ ID NO 88
<211> LENGTH: 10
<212> TYPE: PRT
<213> ORGANISM: Bacillus subtilis

<400> SEQUENCE: 88

Leu Lys Asn Ile Thr Phe Arg Ile Glu Gly
 1               5                  10

<210> SEQ ID NO 89
<211> LENGTH: 7
<212> TYPE: PRT
<213> ORGANISM: Bacillus subtilis

<400> SEQUENCE: 89

Cys Phe Val Phe Leu Lys Leu
 1               5

<210> SEQ ID NO 90
<211> LENGTH: 15
<212> TYPE: PRT
<213> ORGANISM: Bacillus subtilis

<400> SEQUENCE: 90

Val Tyr Phe Ile Ala Tyr Phe Lys Lys Asp Arg Tyr Asn Asn Gln
 1               5                  10                  15

<210> SEQ ID NO 91
<211> LENGTH: 25
<212> TYPE: PRT
<213> ORGANISM: Bacillus subtilis

<400> SEQUENCE: 91

Gly Gln Met Asn Lys Asp Cys Ile Leu Arg Gly Arg Val Glu Ile Pro
 1               5                  10                  15

Thr Gly Gly Ser Lys Ala His Leu Leu
            20                  25

<210> SEQ ID NO 92
<211> LENGTH: 24
<212> TYPE: PRT
<213> ORGANISM: Bacillus subtilis

<400> SEQUENCE: 92

Pro Val Cys Ile Ser Thr Arg Trp Ile Gln Phe Lys Leu Lys Pro Thr
 1               5                  10                  15

Val Lys Val Trp Met Gly Glu Gly
            20
```

<210> SEQ ID NO 93
<211> LENGTH: 6
<212> TYPE: PRT
<213> ORGANISM: Bacillus subtilis

<400> SEQUENCE: 93

Ala Ala Met Gln Asn Val
 1               5

<210> SEQ ID NO 94
<211> LENGTH: 9
<212> TYPE: PRT
<213> ORGANISM: Bacillus subtilis

<400> SEQUENCE: 94

Lys Cys Ile Val Leu Phe Pro Ile Ala
 1               5

<210> SEQ ID NO 95
<211> LENGTH: 11
<212> TYPE: PRT
<213> ORGANISM: Bacillus subtilis

<400> SEQUENCE: 95

Ser Pro Glu Phe Phe Ile Asn Ser Gly Leu Phe
 1               5                  10

<210> SEQ ID NO 96
<211> LENGTH: 54
<212> TYPE: PRT
<213> ORGANISM: Bacillus subtilis

<400> SEQUENCE: 96

Ile Thr Lys Glu Gly Arg Glu Thr Asn Gly Arg Val Leu Tyr Glu Ala
 1               5                  10                  15

Gly Leu Arg Ser Cys Glu Ala Gly Arg Arg Thr Asp Arg Ile Gln Ser
            20                  25                  30

Ala Arg Arg Arg Cys Cys Arg Lys Gly Arg Thr Asn Cys Arg Asn Gly
        35                  40                  45

Arg Pro Phe Lys Ile Trp
    50

<210> SEQ ID NO 97
<211> LENGTH: 55
<212> TYPE: PRT
<213> ORGANISM: Bacillus subtilis

<400> SEQUENCE: 97

Ser Ser Cys Arg Ser Ser Cys His Pro Tyr Gly Trp Ser Thr Cys Arg
 1               5                  10                  15

Gly Cys Arg His Leu Arg Tyr Thr Arg Thr Val Gln Pro Leu Arg Lys
            20                  25                  30

Asn Thr Ala Met Cys Arg Ile Asp Tyr Gln Leu Trp Tyr Gln Lys Ser
        35                  40                  45

Val Arg Gly Asp Glu Arg Ser
    50                  55

<210> SEQ ID NO 98
<211> LENGTH: 16
<212> TYPE: PRT
<213> ORGANISM: Bacillus subtilis

<400> SEQUENCE: 98

Ser Ala Cys Gly Trp Lys Arg Asp Gln His Asp Glu Arg Ser Trp His
1               5                   10                  15

<210> SEQ ID NO 99
<211> LENGTH: 14
<212> TYPE: PRT
<213> ORGANISM: Bacillus subtilis

<400> SEQUENCE: 99

Gly Lys Gly Arg His Pro Gly Arg Pro Gly Gly Glu Ala Glu
1               5                   10

<210> SEQ ID NO 100
<211> LENGTH: 21
<212> TYPE: PRT
<213> ORGANISM: Bacillus subtilis

<400> SEQUENCE: 100

Lys Ile Ser Ala Leu Tyr Glu Asp Arg Pro Ser Val Arg His Ala Lys
1               5                   10                  15

Ser Gly Cys Gln Pro
            20

<210> SEQ ID NO 101
<211> LENGTH: 8
<212> TYPE: PRT
<213> ORGANISM: Bacillus subtilis

<400> SEQUENCE: 101

Arg Gln Asp Ser Tyr Gln His Gly
1               5

<210> SEQ ID NO 102
<211> LENGTH: 53
<212> TYPE: PRT
<213> ORGANISM: Bacillus subtilis

<400> SEQUENCE: 102

Gln Gln Met Asp His Val Arg Gly Cys Lys Thr Gly Cys Ser Ala Ile
1               5                   10                  15

Gln Glu Asn Thr Pro Lys His Phe Ser Arg Ser Trp His Ser Glu Ser
            20                  25                  30

Arg Gln Ser Glu Leu Asn Leu Gln Thr Ala Glu Cys Asn Lys Thr Ala
        35                  40                  45

Gly Ser Gly His Thr
    50

<210> SEQ ID NO 103
<211> LENGTH: 6
<212> TYPE: PRT
<213> ORGANISM: Bacillus subtilis

<400> SEQUENCE: 103

Tyr Arg Thr Leu Asp Ser
1               5

<210> SEQ ID NO 104
<211> LENGTH: 35
<212> TYPE: PRT
<213> ORGANISM: Bacillus subtilis

<400> SEQUENCE: 104

Ser Asp Leu Arg Ser Asn Ser Ala Asp Met Asp Phe Tyr Asp Gly Thr
1               5                   10                  15

Arg Arg Arg Gly Lys Glu Lys Thr Ala Phe Ser Phe Ser Glu His
            20                  25                  30

Ile Tyr Thr
        35

<210> SEQ ID NO 105
<211> LENGTH: 7
<212> TYPE: PRT
<213> ORGANISM: Bacillus subtilis

<400> SEQUENCE: 105

Asn Arg Ala His Ser Asn Ser
1               5

<210> SEQ ID NO 106
<211> LENGTH: 40
<212> TYPE: PRT
<213> ORGANISM: Bacillus subtilis

<400> SEQUENCE: 106

Cys Phe Glu Asp Pro Ser Gly Arg Arg His His Val Gly Val Cys Gly
1               5                   10                  15

Arg Arg Phe Ser Cys Ser Arg Lys Leu Cys Gln Arg Arg Leu Phe Ser
            20                  25                  30

Arg Asn His Leu Leu Phe Cys Pro
        35                  40

<210> SEQ ID NO 107
<211> LENGTH: 13
<212> TYPE: PRT
<213> ORGANISM: Bacillus subtilis

<400> SEQUENCE: 107

Thr Asn Arg Arg Asn Ala Cys Ser Gln Leu Asn Leu Arg
1               5                   10

<210> SEQ ID NO 108
<211> LENGTH: 14
<212> TYPE: PRT
<213> ORGANISM: Bacillus subtilis

<400> SEQUENCE: 108

Arg Phe Ser Ile Asn Glu Arg Cys Pro Leu Ile Thr Ile His
1               5                   10

<210> SEQ ID NO 109
<211> LENGTH: 6
<212> TYPE: PRT
<213> ORGANISM: Bacillus subtilis

<400> SEQUENCE: 109

Tyr Asn Pro Asn Arg Pro
1               5

<210> SEQ ID NO 110
<211> LENGTH: 13
<212> TYPE: PRT
<213> ORGANISM: Bacillus subtilis

<400> SEQUENCE: 110

Tyr Gln Thr Asp Gly Lys Thr Asp Lys Gly Ile Gly Trp
1               5                   10

<210> SEQ ID NO 111
<211> LENGTH: 15
<212> TYPE: PRT
<213> ORGANISM: Bacillus subtilis

<400> SEQUENCE: 111

Pro Cys Leu Gln Glu Leu Ser Lys Lys Gln Ala Gln Ser Asn Pro
1               5                   10                  15

<210> SEQ ID NO 112
<211> LENGTH: 8
<212> TYPE: PRT
<213> ORGANISM: Bacillus subtilis

<400> SEQUENCE: 112

Lys Lys Gln Gly Met Gln Trp Pro
1               5

<210> SEQ ID NO 113
<211> LENGTH: 7
<212> TYPE: PRT
<213> ORGANISM: Bacillus subtilis

<400> SEQUENCE: 113

Leu Leu Asn Ala Gln Arg Phe
1               5

<210> SEQ ID NO 114
<211> LENGTH: 10
<212> TYPE: PRT
<213> ORGANISM: Bacillus subtilis

<400> SEQUENCE: 114

Arg Met Phe Ile Leu Ala Thr Ala Leu Gln
1               5                   10

<210> SEQ ID NO 115
<211> LENGTH: 4
<212> TYPE: PRT
<213> ORGANISM: Bacillus subtilis

<400> SEQUENCE: 115

Thr Ala Phe Val
1

<210> SEQ ID NO 116
<211> LENGTH: 23
<212> TYPE: PRT
<213> ORGANISM: Bacillus subtilis

<400> SEQUENCE: 116

Leu Ser Leu Ile Leu Gln Lys Ile Asn Ser Gln Trp Met Leu Cys Leu
1               5                   10                  15

Lys Gln Ser Lys Leu Arg His
            20

<210> SEQ ID NO 117
<211> LENGTH: 5
<212> TYPE: PRT
<213> ORGANISM: Bacillus subtilis

```
<400> SEQUENCE: 117

Gln Lys Glu Ala Lys
 1               5

<210> SEQ ID NO 118
<211> LENGTH: 40
<212> TYPE: PRT
<213> ORGANISM: Bacillus subtilis

<400> SEQUENCE: 118

Ile Trp Lys Glu Arg Trp Arg Gln Thr Ala Val Ser Glu Ala Ile Ser
 1               5                  10                  15

Ser Gln Ala Met Ser Thr Glu Leu Arg Lys Ser His Glu Leu Lys Arg
            20                  25                  30

Lys Ala Thr Gln Phe Thr Met Ile
        35                  40

<210> SEQ ID NO 119
<211> LENGTH: 5
<212> TYPE: PRT
<213> ORGANISM: Bacillus subtilis

<400> SEQUENCE: 119

Lys Trp Thr Arg His
 1               5

<210> SEQ ID NO 120
<211> LENGTH: 5
<212> TYPE: PRT
<213> ORGANISM: Bacillus subtilis

<400> SEQUENCE: 120

Gln Lys His Trp Phe
 1               5

<210> SEQ ID NO 121
<211> LENGTH: 8
<212> TYPE: PRT
<213> ORGANISM: Bacillus subtilis

<400> SEQUENCE: 121

Arg Asp Gln Leu Leu Trp Met Ala
 1               5

<210> SEQ ID NO 122
<211> LENGTH: 4
<212> TYPE: PRT
<213> ORGANISM: Bacillus subtilis

<400> SEQUENCE: 122

Pro Tyr Ser Ala
 1

<210> SEQ ID NO 123
<211> LENGTH: 4
<212> TYPE: PRT
<213> ORGANISM: Bacillus subtilis

<400> SEQUENCE: 123

Gln Lys Thr Gln
 1

<210> SEQ ID NO 124
```

```
<211> LENGTH: 18
<212> TYPE: PRT
<213> ORGANISM: Bacillus subtilis

<400> SEQUENCE: 124

Tyr Arg Ile Arg Ser Ala Lys Arg Ser Phe Gln Lys Lys Arg Ser Ala
 1               5                  10                  15
Leu Lys

<210> SEQ ID NO 125
<211> LENGTH: 5
<212> TYPE: PRT
<213> ORGANISM: Bacillus subtilis

<400> SEQUENCE: 125

Ile Ser Asn Ala Ile
 1               5

<210> SEQ ID NO 126
<211> LENGTH: 25
<212> TYPE: PRT
<213> ORGANISM: Bacillus subtilis

<400> SEQUENCE: 126

Ser Glu Asn Ile Cys Ile Asp Phe Cys Ile Lys Pro Met Lys Ile Arg
 1               5                  10                  15
Pro Asn Lys Pro Leu Gln Lys Pro Ser
            20                  25

<210> SEQ ID NO 127
<211> LENGTH: 32
<212> TYPE: PRT
<213> ORGANISM: Bacillus subtilis

<400> SEQUENCE: 127

Ala Lys Thr Ala Phe Arg Glu Glu Asp Leu His Val Ser Ser Asp Arg
 1               5                  10                  15
Arg Ser Thr Gly Arg Phe Lys Lys Arg Arg Ser His His Arg Cys Arg
            20                  25                  30

<210> SEQ ID NO 128
<211> LENGTH: 4
<212> TYPE: PRT
<213> ORGANISM: Bacillus subtilis

<400> SEQUENCE: 128

Arg Gln Arg Lys
 1

<210> SEQ ID NO 129
<211> LENGTH: 15
<212> TYPE: PRT
<213> ORGANISM: Bacillus subtilis

<400> SEQUENCE: 129

Arg Arg Leu Cys Gly Ser Cys Arg Ala Cys Asn Ala Gly Ser His
 1               5                  10                  15

<210> SEQ ID NO 130
<211> LENGTH: 15
<212> TYPE: PRT
<213> ORGANISM: Bacillus subtilis

<400> SEQUENCE: 130
```

```
Leu Tyr Gly Asp Thr Trp Glu Arg Thr Asp Leu His Ala Ala Gln
 1               5                  10                  15
```

<210> SEQ ID NO 131
<211> LENGTH: 6
<212> TYPE: PRT
<213> ORGANISM: Bacillus subtilis

<400> SEQUENCE: 131

```
Gly Asn Arg Arg Gln Ala
 1               5
```

<210> SEQ ID NO 132
<211> LENGTH: 5
<212> TYPE: PRT
<213> ORGANISM: Bacillus subtilis

<400> SEQUENCE: 132

```
Ser Ser Pro Tyr Gly
 1               5
```

<210> SEQ ID NO 133
<211> LENGTH: 15
<212> TYPE: PRT
<213> ORGANISM: Bacillus subtilis

<400> SEQUENCE: 133

```
Tyr Arg Leu Ser Pro His Cys Ile Tyr Arg Lys His Arg Pro Ser
 1               5                  10                  15
```

<210> SEQ ID NO 134
<211> LENGTH: 25
<212> TYPE: PRT
<213> ORGANISM: Bacillus subtilis

<400> SEQUENCE: 134

```
Asn Glu Asp Arg Tyr Gln Arg Ser Arg Lys Ile Phe Tyr Arg Ser Ser
 1               5                  10                  15

Ile Ala Gly Gln Gln Ile Arg Ala Ile
            20                  25
```

<210> SEQ ID NO 135
<211> LENGTH: 28
<212> TYPE: PRT
<213> ORGANISM: Bacillus subtilis

<400> SEQUENCE: 135

```
Phe Ser Ala Ser Gly Ala His Phe Ser Thr Asp Cys Glu Lys Arg Arg
 1               5                  10                  15

Cys Pro Glu Lys Arg Gly Pro Tyr Arg Ser Cys Cys
            20                  25
```

<210> SEQ ID NO 136
<211> LENGTH: 11
<212> TYPE: PRT
<213> ORGANISM: Bacillus subtilis

<400> SEQUENCE: 136

```
Ser Leu Arg Ile Ser Arg Ser Arg Arg His Leu
 1               5                  10
```

<210> SEQ ID NO 137
<211> LENGTH: 8

-continued

```
<212> TYPE: PRT
<213> ORGANISM: Bacillus subtilis

<400> SEQUENCE: 137

Arg Arg Asn Asp Gly Glu Ser Ala
 1               5

<210> SEQ ID NO 138
<211> LENGTH: 12
<212> TYPE: PRT
<213> ORGANISM: Bacillus subtilis

<400> SEQUENCE: 138

Asn Cys Glu Lys Ala Ser Ile Lys Asn Asp His His
 1               5                  10

<210> SEQ ID NO 139
<211> LENGTH: 15
<212> TYPE: PRT
<213> ORGANISM: Bacillus subtilis

<400> SEQUENCE: 139

Gly Phe Asp Ser Ile Pro Leu Gln Ser Asp Asn Thr Cys Arg Ala
 1               5                  10                  15

<210> SEQ ID NO 140
<211> LENGTH: 5
<212> TYPE: PRT
<213> ORGANISM: Bacillus subtilis

<400> SEQUENCE: 140

His Tyr Ala Ala Tyr
 1               5

<210> SEQ ID NO 141
<211> LENGTH: 4
<212> TYPE: PRT
<213> ORGANISM: Bacillus subtilis

<400> SEQUENCE: 141

Phe Trp Asp Ile
 1

<210> SEQ ID NO 142
<211> LENGTH: 6
<212> TYPE: PRT
<213> ORGANISM: Bacillus subtilis

<400> SEQUENCE: 142

Gly Leu Trp Ile His Lys
 1               5

<210> SEQ ID NO 143
<211> LENGTH: 32
<212> TYPE: PRT
<213> ORGANISM: Bacillus subtilis

<400> SEQUENCE: 143

Gly Arg Trp Lys Arg Ala Cys Arg Ile Cys Asp Gly Arg Cys Ala Val
 1               5                  10                  15

Arg Arg Arg Thr Gly Ile Gly Pro Gly Ala Phe Arg Met Ser His Arg
                20                  25                  30

<210> SEQ ID NO 144
```

<210> SEQ ID NO 144
<211> LENGTH: 7
<212> TYPE: PRT
<213> ORGANISM: Bacillus subtilis

<400> SEQUENCE: 144

Arg Val Trp Leu Ser Ser Leu
 1               5

<210> SEQ ID NO 145
<211> LENGTH: 34
<212> TYPE: PRT
<213> ORGANISM: Bacillus subtilis

<400> SEQUENCE: 145

Leu Arg Thr Ala Ala Ala Arg Arg Ala Glu Pro Asn Cys Arg Arg
 1               5                  10                  15

Pro Trp Ser Ala Pro Val Leu Ala Pro Arg Arg Thr Arg His Arg Phe
             20                  25                  30

Asn Gln

<210> SEQ ID NO 146
<211> LENGTH: 4
<212> TYPE: PRT
<213> ORGANISM: Bacillus subtilis

<400> SEQUENCE: 146

Ile Lys Ser Leu
 1

<210> SEQ ID NO 147
<211> LENGTH: 6
<212> TYPE: PRT
<213> ORGANISM: Bacillus subtilis

<400> SEQUENCE: 147

Ala Ser Gly Thr Arg Leu
 1               5

<210> SEQ ID NO 148
<211> LENGTH: 5
<212> TYPE: PRT
<213> ORGANISM: Bacillus subtilis

<400> SEQUENCE: 148

His Arg Arg Ser Gln
 1               5

<210> SEQ ID NO 149
<211> LENGTH: 31
<212> TYPE: PRT
<213> ORGANISM: Bacillus subtilis

<400> SEQUENCE: 149

Gly Ala Trp Ile Leu Ala Gly Ser Ser Gln Leu Trp His Arg Ser Thr
 1               5                  10                  15

Asn Phe Thr Arg Pro Arg Cys Pro Glu Tyr Glu Ala Phe Asp Glu
             20                  25                  30

<210> SEQ ID NO 150
<211> LENGTH: 7
<212> TYPE: PRT
<213> ORGANISM: Bacillus subtilis

<400> SEQUENCE: 150

-continued

Ser Ala Lys Asn Arg Arg Pro
 1               5

<210> SEQ ID NO 151
<211> LENGTH: 20
<212> TYPE: PRT
<213> ORGANISM: Bacillus subtilis

<400> SEQUENCE: 151

Arg Leu Arg Thr Gln Tyr Phe Arg Lys Ser Ala Ala Ser Asn Gly Gly
 1               5                  10                  15

Glu Arg Thr Gln
            20

<210> SEQ ID NO 152
<211> LENGTH: 182
<212> TYPE: PRT
<213> ORGANISM: Bacillus subtilis

<400> SEQUENCE: 152

Lys Ile Phe Ala Asn Gln Asn Glu Gln Ala Arg Ser Phe Thr Ser Phe
 1               5                  10                  15

Leu Ile Thr Asn Ile Thr Lys Lys Asp Gly Asn His Met Asn Ile Ile
            20                  25                  30

Gln Gly Asn Leu Val Gly Thr Gly Leu Lys Ile Gly Ile Val Val Gly
         35                  40                  45

Arg Phe Asn Asp Phe Ile Thr Ser Lys Leu Leu Ser Gly Ala Glu Asp
    50                  55                  60

Ala Leu Leu Arg His Gly Val Asp Thr Asn Asp Ile Asp Val Ala Trp
65                  70                  75                  80

Val Pro Gly Ala Phe Glu Ile Pro Phe Ala Ala Lys Lys Met Ala Glu
                85                  90                  95

Thr Lys Lys Tyr Asp Ala Ile Ile Thr Leu Gly Thr Val Ile Arg Gly
            100                 105                 110

Ala Thr Thr His Tyr Asp Tyr Val Cys Asn Glu Ala Ala Lys Gly Ile
        115                 120                 125

Ala Gln Ala Ala Asn Thr Thr Gly Val Pro Val Ile Phe Gly Ile Val
    130                 135                 140

Thr Thr Glu Asn Ile Glu Gln Ala Ile Glu Arg Ala Gly Thr Lys Ala
145                 150                 155                 160

Gly Asn Lys Gly Val Asp Cys Ala Val Ser Ala Ile Glu Met Ala Asn
                165                 170                 175

Leu Asn Arg Ser Phe Glu
            180

<210> SEQ ID NO 153
<211> LENGTH: 11
<212> TYPE: PRT
<213> ORGANISM: Bacillus subtilis

<400> SEQUENCE: 153

Phe Ala Glu Asn Ser Leu Lys Ile Trp Arg Lys
 1               5                  10

<210> SEQ ID NO 154
<211> LENGTH: 21
<212> TYPE: PRT
<213> ORGANISM: Bacillus subtilis -continued

```
<400> SEQUENCE: 154

Tyr Asn Val Arg Lys Arg Ile Thr Tyr Ser Tyr Pro Leu Ile Ala Asp
1               5                   10                  15
Trp Thr Phe Trp Ile
            20

<210> SEQ ID NO 155
<211> LENGTH: 8
<212> TYPE: PRT
<213> ORGANISM: Bacillus subtilis

<400> SEQUENCE: 155

Arg Gly Phe Tyr Val Asn Ser Leu
1               5

<210> SEQ ID NO 156
<211> LENGTH: 12
<212> TYPE: PRT
<213> ORGANISM: Bacillus subtilis

<400> SEQUENCE: 156

Lys Asp Cys Asp Gly Ala Ser Phe Val Tyr Ala Glu
1               5                   10

<210> SEQ ID NO 157
<211> LENGTH: 6
<212> TYPE: PRT
<213> ORGANISM: Bacillus subtilis

<400> SEQUENCE: 157

Ala Ala Ser Ala Asp Asn
1               5

<210> SEQ ID NO 158
<211> LENGTH: 30
<212> TYPE: PRT
<213> ORGANISM: Bacillus subtilis

<400> SEQUENCE: 158

Gly Leu Arg Asn Gly Tyr Arg Pro Pro Ala Leu Ser Leu Glu Arg Gly
1               5                   10                  15
Arg Gly Tyr Arg Arg Ser Asn Arg Ser Arg Lys Lys Gly Phe
            20                  25                  30

<210> SEQ ID NO 159
<211> LENGTH: 35
<212> TYPE: PRT
<213> ORGANISM: Bacillus subtilis

<400> SEQUENCE: 159

Asp Pro Ala Tyr Gln Cys Glu Ser Phe Ser Pro Ser Arg Asn Arg
1               5                   10                  15
Lys Thr Asp Asp Gly Cys Phe Lys Ala Phe Ile Gln Asn Ala Ser Thr
            20                  25                  30
Gly Ser Lys
        35

<210> SEQ ID NO 160
<211> LENGTH: 20
<212> TYPE: PRT
<213> ORGANISM: Bacillus subtilis

<400> SEQUENCE: 160
```

Ile Asn Ala Glu Leu Phe Arg Thr Leu Ser Arg Ser Ala Gly Ser Arg
1               5                   10                  15

His Phe Ile Gln
            20

<210> SEQ ID NO 161
<211> LENGTH: 73
<212> TYPE: PRT
<213> ORGANISM: Bacillus subtilis

<400> SEQUENCE: 161

Leu Ser Arg Gly Cys Asp Gln Ser Leu Leu Phe Phe Leu Arg Ser Ile
1               5                   10                  15

Ser Phe Ser Arg Ser Arg Met Thr Ser Val Arg Ser Arg Lys Arg Cys
                20                  25                  30

Leu Ser Ile Arg Asn Met Leu Leu Ser Ala Leu Gly Cys Pro His Val
            35                  40                  45

Tyr Phe Phe Leu His Ser Ile Leu His Ala Ser Ser Ser Phe Ser
        50                  55                  60

Ser Leu Ile Gly Ser Ile Met Leu Leu
65                  70

<210> SEQ ID NO 162
<211> LENGTH: 8
<212> TYPE: PRT
<213> ORGANISM: Bacillus subtilis

<400> SEQUENCE: 162

Ala Glu Thr Val Ser Ile Cys Ser
1               5

<210> SEQ ID NO 163
<211> LENGTH: 10
<212> TYPE: PRT
<213> ORGANISM: Bacillus subtilis

<400> SEQUENCE: 163

Thr Asp Cys Ile Ser Ser Ser Lys Arg Pro
1               5                   10

<210> SEQ ID NO 164
<211> LENGTH: 12
<212> TYPE: PRT
<213> ORGANISM: Bacillus subtilis

<400> SEQUENCE: 164

Ser Ser Pro Lys Ser Ser Thr Ala Arg Cys Ser Ala
1               5                   10

<210> SEQ ID NO 165
<211> LENGTH: 19
<212> TYPE: PRT
<213> ORGANISM: Bacillus subtilis

<400> SEQUENCE: 165

Arg Ile Arg Met Leu Phe Ala Ile Ser Leu Phe Ala Pro Ala Val Phe
1               5                   10                  15

Cys Leu Leu

<210> SEQ ID NO 166
<211> LENGTH: 6

```
<212> TYPE: PRT
<213> ORGANISM: Bacillus subtilis

<400> SEQUENCE: 166

Tyr Lys Ala Thr Ala Ser
 1               5

<210> SEQ ID NO 167
<211> LENGTH: 5
<212> TYPE: PRT
<213> ORGANISM: Bacillus subtilis

<400> SEQUENCE: 167

Ile Lys Pro Thr Gln
 1               5

<210> SEQ ID NO 168
<211> LENGTH: 21
<212> TYPE: PRT
<213> ORGANISM: Bacillus subtilis

<400> SEQUENCE: 168

Arg Phe Arg Phe Phe Gly Gly Ser Ser Phe Gln Tyr Ser Ser Asn Ile
 1               5                  10                  15

Ser Trp His Ser Lys
             20

<210> SEQ ID NO 169
<211> LENGTH: 4
<212> TYPE: PRT
<213> ORGANISM: Bacillus subtilis

<400> SEQUENCE: 169

Ser Arg Val Ala
 1

<210> SEQ ID NO 170
<211> LENGTH: 4
<212> TYPE: PRT
<213> ORGANISM: Bacillus subtilis

<400> SEQUENCE: 170

Asn Ser Thr Arg
 1

<210> SEQ ID NO 171
<211> LENGTH: 4
<212> TYPE: PRT
<213> ORGANISM: Bacillus subtilis

<400> SEQUENCE: 171

Ala Gly Arg Leu
 1

<210> SEQ ID NO 172
<211> LENGTH: 7
<212> TYPE: PRT
<213> ORGANISM: Bacillus subtilis

<400> SEQUENCE: 172

Arg Ile Pro His Gly Gln Pro
 1               5

<210> SEQ ID NO 173
```

<211> LENGTH: 21
<212> TYPE: PRT
<213> ORGANISM: Bacillus subtilis

<400> SEQUENCE: 173

Arg Pro Trp Pro Leu His Glu Lys Thr Asn Cys Gly Tyr Val Lys Val
 1               5                  10                  15

Cys Phe Leu Pro Val
            20

<210> SEQ ID NO 174
<211> LENGTH: 36
<212> TYPE: PRT
<213> ORGANISM: Bacillus subtilis

<400> SEQUENCE: 174

Arg Asn Ala Gln Asn Lys Leu Gly Ser Ser Phe Pro Leu Gly Leu
 1               5                  10                  15

Leu Phe Leu Tyr Leu Phe Tyr Gly His Pro Leu Lys Thr Glu His Lys
            20                  25                  30

Phe Val Tyr Leu
        35

<210> SEQ ID NO 175
<211> LENGTH: 29
<212> TYPE: PRT
<213> ORGANISM: Bacillus subtilis

<400> SEQUENCE: 175

Lys Arg Asn Phe Cys Arg Asn Val Lys His Ile Pro Val Met His Arg
 1               5                  10                  15

Tyr Ile Asn Asn Leu Arg Glu Phe Thr Val Phe Tyr Ser
            20                  25

<210> SEQ ID NO 176
<211> LENGTH: 9
<212> TYPE: PRT
<213> ORGANISM: Bacillus subtilis

<400> SEQUENCE: 176

Lys Lys Gly Ile Thr His Met Asn Glu
 1               5

<210> SEQ ID NO 177
<211> LENGTH: 34
<212> TYPE: PRT
<213> ORGANISM: Bacillus subtilis

<400> SEQUENCE: 177

Ile His Ile Gly Trp Arg Phe Arg Asn Gly Lys Asn Lys Asn Gln Asp
 1               5                  10                  15

Tyr His Ser Val Ser Ala Phe Ala Phe Thr Cys Arg Arg Leu Tyr Val
            20                  25                  30

His Lys

<210> SEQ ID NO 178
<211> LENGTH: 24
<212> TYPE: PRT
<213> ORGANISM: Bacillus subtilis

<400> SEQUENCE: 178

Ala Glu Gly Cys Ser Asp Ser Asn Trp Thr Asn Leu Val Leu Gly Arg

-continued

```
                1               5              10              15
Arg Gly Ile His His Pro Gly Ile
                               20
```

<210> SEQ ID NO 179
<211> LENGTH: 4
<212> TYPE: PRT
<213> ORGANISM: Bacillus subtilis

<400> SEQUENCE: 179

```
Ser Asp Glu Asn
 1
```

<210> SEQ ID NO 180
<211> LENGTH: 26
<212> TYPE: PRT
<213> ORGANISM: Bacillus subtilis

<400> SEQUENCE: 180

```
Arg Leu Arg Val Ser Trp Ser Ser Arg Lys Arg Asn Glu Asn His Leu
 1               5                  10                  15
Gln Arg Lys Lys Ile Lys Ser Gly Phe Ile
                20                  25
```

<210> SEQ ID NO 181
<211> LENGTH: 4
<212> TYPE: PRT
<213> ORGANISM: Bacillus subtilis

<400> SEQUENCE: 181

```
Tyr Lys Arg Arg
 1
```

<210> SEQ ID NO 182
<211> LENGTH: 20
<212> TYPE: PRT
<213> ORGANISM: Bacillus subtilis

<400> SEQUENCE: 182

```
Gly Leu Leu Gln Gln Ile Lys Ala Asp Arg Arg Leu Ile Lys Val Ala
 1               5                  10                  15
Lys Val Asn Asp
                20
```

<210> SEQ ID NO 183
<211> LENGTH: 36
<212> TYPE: PRT
<213> ORGANISM: Bacillus subtilis

<400> SEQUENCE: 183

```
Lys Thr Ser Pro Phe Gly Ser Lys Gly Asp Val Leu Phe Phe Ser Asn
 1               5                  10                  15
Cys Lys Phe Ile Ser Leu Arg Thr Leu Lys Arg Ile Ala Ile Ile Thr
                20                  25                  30
Asn Lys Asp Lys
                35
```

<210> SEQ ID NO 184
<211> LENGTH: 29
<212> TYPE: PRT
<213> ORGANISM: Bacillus subtilis

<400> SEQUENCE: 184

```
Ile Lys Ile Val Ser Phe Gly Ala Gly Trp Lys Ser Arg Pro Ala Val
 1               5                  10                  15

Val Lys His Ile Cys Phe Arg Ala Arg Asp Pro Cys Ala
                20                  25
```

<210> SEQ ID NO 185
<211> LENGTH: 8
<212> TYPE: PRT
<213> ORGANISM: Bacillus subtilis

<400> SEQUENCE: 185

```
Ala Arg Gly Gly Phe Ser Leu Ser
 1               5
```

<210> SEQ ID NO 186
<211> LENGTH: 18
<212> TYPE: PRT
<213> ORGANISM: Bacillus subtilis

<400> SEQUENCE: 186

```
Lys Ser Gly Trp Glu Lys Asp Asp Glu Pro Leu Cys Lys Met Phe Lys
 1               5                  10                  15

Asn Ala
```

<210> SEQ ID NO 187
<211> LENGTH: 15
<212> TYPE: PRT
<213> ORGANISM: Bacillus subtilis

<400> SEQUENCE: 187

```
Cys Tyr Phe Leu Leu Arg Lys Ile Pro Lys Ala Pro Asn Phe Leu
 1               5                  10                  15
```

<210> SEQ ID NO 188
<211> LENGTH: 8
<212> TYPE: PRT
<213> ORGANISM: Bacillus subtilis

<400> SEQUENCE: 188

```
Ile Arg Gly Phe Phe Asp Gly Lys
 1               5
```

<210> SEQ ID NO 189
<211> LENGTH: 368
<212> TYPE: PRT
<213> ORGANISM: Bacillus subtilis

<400> SEQUENCE: 189

```
Gln Lys Arg Gly Gly Lys Gln Met Glu Glu Tyr Tyr Met Lys Leu Ala
 1               5                  10                  15

Leu Asp Leu Ala Lys Gln Gly Glu Gly Gln Thr Glu Ser Asn Pro Leu
                20                  25                  30

Val Gly Ala Val Val Lys Asp Gly Gln Ile Val Gly Met Gly Ala
                35                  40                  45

His Leu Lys Tyr Gly Glu Ala His Ala Glu Val His Ala Ile His Met
         50                  55                  60

Ala Gly Ala His Ala Glu Gly Ala Asp Ile Tyr Val Thr Leu Glu Pro
 65                  70                  75                  80

Cys Ser His Tyr Gly Lys Thr Pro Pro Cys Ala Glu Leu Ile Ile Asn
                85                  90                  95
```

```
Ser Gly Ile Lys Arg Val Phe Val Ala Met Arg Asp Pro Asn Pro Leu
            100                 105                 110

Val Ala Gly Arg Gly Ile Ser Met Met Lys Glu Ala Gly Ile Glu Val
        115                 120                 125

Arg Glu Gly Ile Leu Ala Asp Gln Ala Glu Arg Leu Asn Glu Lys Phe
    130                 135                 140

Leu His Phe Met Arg Thr Gly Leu Pro Tyr Val Thr Leu Lys Ala Ala
145                 150                 155                 160

Ala Ser Leu Asp Gly Lys Ile Ala Thr Ser Thr Gly Asp Ser Lys Trp
                165                 170                 175

Ile Thr Ser Glu Ala Ala Arg Gln Asp Ala Gln Gln Tyr Arg Lys Thr
            180                 185                 190

His Gln Ser Ile Leu Val Gly Val Gly Thr Val Lys Ala Asp Asn Pro
        195                 200                 205

Ser Leu Thr Cys Arg Leu Pro Asn Val Thr Lys Gln Pro Val Arg Val
    210                 215                 220

Ile Leu Asp Thr Val Leu Ser Ile Pro Glu Asp Ala Lys Val Ile Cys
225                 230                 235                 240

Asp Gln Ile Ala Pro Thr Trp Ile Phe Thr Thr Ala Arg Ala Asp Glu
                245                 250                 255

Glu Lys Lys Lys Arg Leu Ser Ala Phe Gly Val Asn Ile Phe Thr Leu
            260                 265                 270

Glu Thr Glu Arg Ile Gln Ile Pro Asp Val Leu Lys Ile Leu Ala Glu
        275                 280                 285

Glu Gly Ile Met Ser Val Tyr Val Glu Gly Gly Ser Ala Val His Gly
    290                 295                 300

Ser Phe Val Lys Glu Gly Cys Phe Gln Glu Ile Ile Phe Tyr Phe Ala
305                 310                 315                 320

Pro Lys Leu Ile Gly Gly Thr His Ala Pro Ser Leu Ile Ser Gly Glu
                325                 330                 335

Gly Phe Gln Ser Met Lys Asp Val Pro Leu Leu Gln Phe Thr Asp Ile
            340                 345                 350

Thr Gln Ile Gly Arg Asp Ile Lys Leu Thr Ala Lys Pro Thr Lys Glu
        355                 360                 365

<210> SEQ ID NO 190
<211> LENGTH: 29
<212> TYPE: PRT
<213> ORGANISM: Bacillus subtilis

<400> SEQUENCE: 190

Asp Gly Asp His Val Tyr Arg Asn Tyr Arg Arg Asn Arg His Asn Arg
1               5                   10                  15

Ile His Glu Lys Ser Arg Ala Cys Asn Gly Leu Asn Tyr
            20                  25

<210> SEQ ID NO 191
<211> LENGTH: 24
<212> TYPE: PRT
<213> ORGANISM: Bacillus subtilis

<400> SEQUENCE: 191

Met Leu Lys Asp Phe Arg Gly Cys Ser Ser Trp Arg Gln His Cys Ser
1               5                   10                  15

Glu Arg His Leu Ser Asp Cys His
            20
```

<210> SEQ ID NO 192
<211> LENGTH: 12
<212> TYPE: PRT
<213> ORGANISM: Bacillus subtilis

<400> SEQUENCE: 192

Phe Tyr Lys Lys Ser Ile His Ser Gly Cys Tyr Ala
 1               5                  10

<210> SEQ ID NO 193
<211> LENGTH: 8
<212> TYPE: PRT
<213> ORGANISM: Bacillus subtilis

<400> SEQUENCE: 193

Asn Ser Gln Ser Tyr Val Thr Glu
 1               5

<210> SEQ ID NO 194
<211> LENGTH: 37
<212> TYPE: PRT
<213> ORGANISM: Bacillus subtilis

<400> SEQUENCE: 194

Phe Asn Lys Arg Lys Gln Ser Lys Ser Gly Lys Ser Asp Gly Gly Lys
 1               5                  10                  15

Arg Pro Phe Arg Arg Pro Phe Arg Leu Arg Pro Cys Arg Arg Asn Cys
                20                  25                  30

Gly Asn His Thr Asn
            35

<210> SEQ ID NO 195
<211> LENGTH: 8
<212> TYPE: PRT
<213> ORGANISM: Bacillus subtilis

<400> SEQUENCE: 195

Arg Glu Lys Gln Arg Ser Leu Leu
 1               5

<210> SEQ ID NO 196
<211> LENGTH: 55
<212> TYPE: PRT
<213> ORGANISM: Bacillus subtilis

<400> SEQUENCE: 196

Phe Lys Asn Gly Pro Val Ile Asn Lys Asn Ile Gly Phe Lys Gly Ile
 1               5                  10                  15

Asn Tyr Cys Gly Trp Arg Glu Leu Asn His Ile Arg Pro Asp Arg Arg
                20                  25                  30

His Ser Asp Asp Leu Leu Asn Thr Ala Tyr Asp Gln Arg Asn Asp Leu
            35                  40                  45

Phe Arg Lys Asn Asp Arg Leu
        50                  55

<210> SEQ ID NO 197
<211> LENGTH: 17
<212> TYPE: PRT
<213> ORGANISM: Bacillus subtilis

<400> SEQUENCE: 197

Ser Glu Tyr Arg Met Arg Tyr Asp Arg Lys Ile Tyr Val Ser Ile Phe
 1               5                  10                  15

```
               1               5              10              15
Ala

<210> SEQ ID NO 198
<211> LENGTH: 419
<212> TYPE: PRT
<213> ORGANISM: Bacillus subtilis

<400> SEQUENCE: 198

Asp Pro Thr Asn His Tyr Lys Ser Leu Leu Lys Arg Lys Arg Leu Leu
  1               5                  10                  15

Glu Arg Lys Ile Cys Met Phe His Pro Ile Glu Glu Ala Leu Asp Ala
                 20                  25                  30

Leu Lys Lys Gly Glu Val Ile Val Val Asp Asp Glu Asp Arg Glu
             35                  40                  45

Asn Glu Gly Asp Phe Val Ala Leu Ala Glu His Ala Thr Pro Glu Val
         50                  55                  60

Ile Asn Phe Met Ala Thr His Gly Arg Gly Leu Ile Cys Thr Pro Leu
 65                  70                  75                  80

Ser Glu Glu Ile Ala Asp Arg Leu Asp Leu His Pro Met Val Glu His
                 85                  90                  95

Asn Thr Asp Ser His His Thr Ala Phe Thr Val Ser Ile Asp His Arg
                100                 105                 110

Glu Thr Lys Thr Gly Ile Ser Ala Gln Glu Arg Ser Phe Thr Val Gln
             115                 120                 125

Ala Leu Leu Asp Ser Lys Ser Val Pro Ser Asp Phe Gln Arg Pro Gly
        130                 135                 140

His Ile Phe Pro Leu Ile Ala Lys Lys Gly Val Leu Lys Ser Ala
145                 150                 155                 160

Gly His Thr Glu Ala Ala Val Asp Leu Ala Glu Ala Cys Gly Ser Pro
                165                 170                 175

Gly Ala Gly Val Ile Cys Glu Ile Met Asn Glu Asp Gly Thr Met Ala
            180                 185                 190

Arg Val Pro Glu Leu Ile Glu Ile Ala Lys Lys His Gln Leu Lys Met
        195                 200                 205

Ile Thr Ile Lys Asp Leu Ile Gln Tyr Arg Tyr Asn Leu Thr Thr Leu
    210                 215                 220

Val Glu Arg Glu Val Asp Ile Thr Leu Pro Thr Asp Phe Gly Thr Phe
225                 230                 235                 240

Lys Val Tyr Gly Tyr Thr Asn Glu Val Asp Gly Lys Glu His Val Ala
                245                 250                 255

Phe Val Met Gly Asp Val Pro Phe Gly Glu Pro Val Leu Val Arg
            260                 265                 270

Val His Ser Glu Cys Leu Thr Gly Asp Val Phe Gly Ser His Arg Cys
        275                 280                 285

Asp Cys Gly Pro Gln Leu His Ala Ala Leu Asn Gln Ile Ala Ala Glu
    290                 295                 300

Gly Arg Gly Val Leu Leu Tyr Leu Arg Gln Glu Gly Arg Gly Ile Gly
305                 310                 315                 320

Leu Ile Asn Lys Leu Lys Ala Tyr Lys Leu Gln Glu Gln Gly Tyr Asp
                325                 330                 335

Thr Val Glu Ala Asn Glu Ala Leu Gly Phe Leu Pro Asp Leu Arg Asn
            340                 345                 350

Tyr Gly Ile Gly Ala Gln Ile Leu Arg Asp Leu Gly Val Arg Asn Met
```

-continued

```
                 355                 360                 365
Lys Leu Leu Thr Asn Asn Pro Arg Lys Ile Ala Gly Leu Glu Gly Tyr
            370                 375                 380

Gly Leu Ser Ile Ser Glu Arg Val Pro Leu Gln Met Glu Ala Lys Glu
385                 390                 395                 400

His Asn Lys Lys Tyr Leu Gln Thr Lys Met Asn Lys Leu Gly His Leu
                405                 410                 415

Leu His Phe

<210> SEQ ID NO 199
<211> LENGTH: 11
<212> TYPE: PRT
<213> ORGANISM: Bacillus subtilis

<400> SEQUENCE: 199

Ser Gln Ile Ser Gln Lys Arg Met Gly Ile Ile
1               5                   10

<210> SEQ ID NO 200
<211> LENGTH: 6
<212> TYPE: PRT
<213> ORGANISM: Bacillus subtilis

<400> SEQUENCE: 200

Ile Ser Tyr Lys Glu Ile
1               5

<210> SEQ ID NO 201
<211> LENGTH: 9
<212> TYPE: PRT
<213> ORGANISM: Bacillus subtilis

<400> SEQUENCE: 201

Leu Val Gln Val Leu Lys Ser Glu Ser
1               5

<210> SEQ ID NO 202
<211> LENGTH: 11
<212> TYPE: PRT
<213> ORGANISM: Bacillus subtilis

<400> SEQUENCE: 202

Glu Asp Leu Met Ile Leu Leu Arg Ala Ser Cys
1               5                   10

<210> SEQ ID NO 203
<211> LENGTH: 11
<212> TYPE: PRT
<213> ORGANISM: Bacillus subtilis

<400> SEQUENCE: 203

Ala Glu Gln Lys Met Arg Cys Ser Asp Met Ala
1               5                   10

<210> SEQ ID NO 204
<211> LENGTH: 72
<212> TYPE: PRT
<213> ORGANISM: Bacillus subtilis

<400> SEQUENCE: 204

Thr Gln Met Thr Leu Met Trp Leu Gly Phe Gln Ala His Leu Lys Tyr
1               5                   10                  15
```

-continued

Arg Leu Leu Arg Lys Lys Trp Arg Lys Gln Lys Asn Met Met Leu Leu
                20                  25                  30

Ser His Trp Ala Leu Ser Ser Glu Ala Gln Arg His Ile Thr Ile Met
        35                  40                  45

Ser Ala Met Lys Leu Gln Lys Ala Ser Arg Lys Gln Gln Thr Leu Leu
    50                  55                  60

Val Tyr Leu Ser Ser Leu Glu Leu
65                  70

<210> SEQ ID NO 205
<211> LENGTH: 20
<212> TYPE: PRT
<213> ORGANISM: Bacillus subtilis

<400> SEQUENCE: 205

Gln Leu Lys Thr Ser Asn Arg Leu Ser Ser Val Pro Ala Gln Lys Arg
1               5                   10                  15

Ala Thr Lys Val
            20

<210> SEQ ID NO 206
<211> LENGTH: 11
<212> TYPE: PRT
<213> ORGANISM: Bacillus subtilis

<400> SEQUENCE: 206

Ile Val Leu Phe Leu Pro Leu Lys Trp Gln Ile
1               5                   10

<210> SEQ ID NO 207
<211> LENGTH: 11
<212> TYPE: PRT
<213> ORGANISM: Bacillus subtilis

<400> SEQUENCE: 207

Thr Ala His Leu Asn Asn Leu Leu Lys Thr Val
1               5                   10

<210> SEQ ID NO 208
<211> LENGTH: 8
<212> TYPE: PRT
<213> ORGANISM: Bacillus subtilis

<400> SEQUENCE: 208

Lys Tyr Gly Glu Asn Asp Ile Met
1               5

<210> SEQ ID NO 209
<211> LENGTH: 9
<212> TYPE: PRT
<213> ORGANISM: Bacillus subtilis

<400> SEQUENCE: 209

Glu Asn Gly Ser Pro Ile Arg Ile Arg
1               5

<210> SEQ ID NO 210
<211> LENGTH: 135
<212> TYPE: PRT
<213> ORGANISM: Bacillus subtilis

<400> SEQUENCE: 210

Gln Thr Gly His Phe Gly Tyr Arg Gly Val Phe Met Leu Ile Arg Tyr

```
               1               5                  10                 15
           Lys Lys Ser Phe Glu Lys Ile Ala Met Gly Leu Leu Ser Phe Met Pro
                          20                 25                 30

Asn Glu Lys Asp Leu Lys Gln Leu Gln Gln Thr Ile Lys Asp Tyr Glu
                          35                 40                 45

Thr Asp Thr Asp Arg Gln Leu Phe Leu Trp Lys Glu Asp Glu Asp Ile
                    50                 55                 60

Val Gly Ala Ile Gly Val Glu Lys Lys Asp Ser Glu Val Glu Ile Arg
            65                 70                 75                 80

His Ile Ser Val Asn Pro Ser Arg His Gln Gly Ile Gly Lys Gln
                          85                 90                 95

Met Met Asp Ala Leu Lys His Leu Phe Lys Thr Gln Val Leu Val Pro
                         100                105                110

Asn Glu Leu Thr Gln Ser Phe Phe Glu Arg Cys Gln Gly Gly Gln Asp
                         115                120                125

Gln Asp Ile Ser Tyr Asn Asn
                         130                135

<210> SEQ ID NO 211
           <211> LENGTH: 21
           <212> TYPE: PRT
           <213> ORGANISM: Bacillus subtilis

<400> SEQUENCE: 211

Ala Glu Ala Val Ile Ser Leu Cys Phe Phe Cys Val Leu Phe Leu
            1               5                  10                 15

Phe His Val His Gly
                          20

<210> SEQ ID NO 212
           <211> LENGTH: 11
           <212> TYPE: PRT
           <213> ORGANISM: Bacillus subtilis

<400> SEQUENCE: 212

Arg Gln Ser Asp Pro Ala Asn Gly Val Cys Arg
            1               5                  10

<210> SEQ ID NO 213
           <211> LENGTH: 4
           <212> TYPE: PRT
           <213> ORGANISM: Bacillus subtilis

<400> SEQUENCE: 213

Glu Ile Cys Cys
            1

<210> SEQ ID NO 214
           <211> LENGTH: 25
           <212> TYPE: PRT
           <213> ORGANISM: Bacillus subtilis

<400> SEQUENCE: 214

Val His Trp Ala Ala Pro Met Tyr Thr Phe Phe Ser Cys Ile Arg Ser
            1               5                  10                 15

Cys Met Leu Pro Pro Val Ser His Leu
                          20                 25

<210> SEQ ID NO 215
           <211> LENGTH: 16
```

```
<212> TYPE: PRT
<213> ORGANISM: Bacillus subtilis

<400> SEQUENCE: 215

Cys Phe Tyr Arg Gln Arg Arg Phe Arg Phe Val Arg Lys Pro Ile Ala
 1               5                  10                  15

<210> SEQ ID NO 216
<211> LENGTH: 48
<212> TYPE: PRT
<213> ORGANISM: Bacillus subtilis

<400> SEQUENCE: 216

Val Arg Ala Asn Gly His Asp Gln Ala Leu Ser Leu Arg Leu Pro Gly
 1               5                  10                  15

Val Leu Leu Glu Glu Ser Gly Cys Cys Ser Pro Ser Val Phe Leu Pro
                20                  25                  30

Arg Leu Tyr Ser Ala Phe Cys Asp Asp Ile Lys Pro Leu Gln Ala Glu
            35                  40                  45

<210> SEQ ID NO 217
<211> LENGTH: 41
<212> TYPE: PRT
<213> ORGANISM: Bacillus subtilis

<400> SEQUENCE: 217

Ser Pro Pro Asn Ser Val Phe Val Ser Leu Ala Asp Leu Pro Ser Asn
 1               5                  10                  15

Ile Leu Leu Ile Phe His Gly Ile Gln Asn Asn Pro Val Ser His Glu
                20                  25                  30

Thr Gln Arg Asp Asn Leu Tyr Lys Leu
            35                  40

<210> SEQ ID NO 218
<211> LENGTH: 42
<212> TYPE: DNA
<213> ORGANISM: Bacillus subtilis

<400> SEQUENCE: 218
aaaaacatca cctttcggat cgaagggtga tgttttgttt tt                    42

<210> SEQ ID NO 219
<211> LENGTH: 36
<212> TYPE: DNA
<213> ORGANISM: Bacillus subtilis

<400> SEQUENCE: 219
aaagccccga atttttttata aattcggggc tttttt                          36

<210> SEQ ID NO 220
<211> LENGTH: 35
<212> TYPE: DNA
<213> ORGANISM: Bacillus subtilis

<400> SEQUENCE: 220
taagcagagg ctgtgatcag tctctgcttt ttttt                            35

<210> SEQ ID NO 221
<211> LENGTH: 116
<212> TYPE: DNA
<213> ORGANISM: Artificial Sequence
<220> FEATURE:
<223> OTHER INFORMATION: Description of Artificial Sequence: A
```

```
                synthetically-generated DNA oligomer containing a
                combination of restriction enzymes sites,
                5'-EcoRI-SmaI-BamHI-3', flanked on either side by
                additional sequence

<400> SEQUENCE: 221
tgattaaaaa acatcacctt tcggatcgaa ggggtgatgt tttgttttc tcgaattccc      60 gggatccaaa ttgtaagttt atttcattgc gtactttaaa aaggatcgct ataata        116

<210> SEQ ID NO 222
<211> LENGTH: 80
<212> TYPE: DNA
<213> ORGANISM: Artificial Sequence
<220> FEATURE:
<223> OTHER INFORMATION: Description of Artificial Sequence: Recreation
        of the  DNA sequence 5' to the BglII site

<400> SEQUENCE: 222
aattcatgca tggatccgac ggtaaataac aaaagagggg agggaaacaa atggaagagt     60
attatatgaa gctggcctta                                                80

<210> SEQ ID NO 223
<211> LENGTH: 80
<212> TYPE: DNA
<213> ORGANISM: Artificial Sequence
<220> FEATURE:
<223> OTHER INFORMATION: Description of Artificial Sequence:Recreation
        of the  DNA sequence 5' to the BglII site

<400> SEQUENCE: 223
gatctaaggc cagcttcata taatactctt ccatttgttt ccctcccctc ttttgttatt    60
taccgtcgga tccatgcatg                                                80

<210> SEQ ID NO 224
<211> LENGTH: 66
<212> TYPE: DNA
<213> ORGANISM: Artificial Sequence
<220> FEATURE:
<223> OTHER INFORMATION: Description of Artificial Sequence: Recreation
        of the sequence from the  above-mentioned DraI site
        past the start of ORF3

<400> SEQUENCE: 224
tcgacggatc cttttagaga ggaagatttg catgtttcat ccgatagaag aagcactgga    60
cgcttt                                                               66

<210> SEQ ID NO 225
<211> LENGTH: 62
<212> TYPE: DNA
<213> ORGANISM: Artificial Sequence
<220> FEATURE:
<223> OTHER INFORMATION: Description of Artificial Sequence: Recreation
        of the sequence from the  above-mentioned DraI site
        past the start of ORF3

<400> SEQUENCE: 225
aaagcgtcca gtgcttcttc tatcggatga acatgcaaa tcttcctctc taaaaggatc     60
cg                                                                   62

<210> SEQ ID NO 226
<211> LENGTH: 78
<212> TYPE: DNA
<213> ORGANISM: Artificial Sequence
<220> FEATURE:
```

```
<223> OTHER INFORMATION: Description of Artificial Sequence: Recreation
      of the sequence from the ClaI site past the end of ORF4

<400> SEQUENCE: 226 cgattttgc ataaagccaa tgaaaataag acccaacaaa ccattacaaa agccttctta      60
agcgaaaacg gcttttag                                                   78

<210> SEQ ID NO 227
<211> LENGTH: 80
<212> TYPE: DNA
<213> ORGANISM: Artificial Sequence
<220> FEATURE:
<223> OTHER INFORMATION: Description of Artificial Sequence: Recreation
      of the sequence from the ClaI site past the end of ORF4

<400> SEQUENCE: 227
aattctaaaa gccgttttcg cttaagaagg cttttgtaat ggtttgttgg gtcttatttt      60
cattggcttt atgcaaaaat                                                 80

<210> SEQ ID NO 228
<211> LENGTH: 83
<212> TYPE: DNA
<213> ORGANISM: Artificial Sequence
<220> FEATURE:
<223> OTHER INFORMATION: Description of Artificial Sequence:Synthetic
      polylinker containing a variety of restriction
      sites.

<400> SEQUENCE: 228
aggagaaatt aactatgaga ggatctcatc accatcacca tcacgggatc gatcatatgg      60
tcgacggatc caagcttaat tag                                             83

<210> SEQ ID NO 229
<211> LENGTH: 68
<212> TYPE: DNA
<213> ORGANISM: Artificial Sequence
<220> FEATURE:
<223> OTHER INFORMATION: Description of Artificial Sequence: The
      promoter interrupting sequence of pXI16 and the introduced
      restriction sites

<400> SEQUENCE: 229
aattttattt gacaaaaatg ggaagcttga tatcgagctc gtcgacccg tgttgtacaa       60 taaatgta                                                              68

<210> SEQ ID NO 230
<211> LENGTH: 54
<212> TYPE: DNA
<213> ORGANISM: Artificial Sequence
<220> FEATURE:
<223> OTHER INFORMATION: Description of Artificial Sequence: A
      synthetic, 54-base oligonucleotide probe used for screening

<400> SEQUENCE: 230
ggagctacaa cacattatga ttatgtttgc aatgaagctg ctaaaggaat tgct           54

<210> SEQ ID NO 231
<211> LENGTH: 29
<212> TYPE: DNA
<213> ORGANISM: Bacillus subtilis
<220> FEATURE:
<221> NAME/KEY: -35_signal
<222> LOCATION: (1)..(6)
<220> FEATURE:
<221> NAME/KEY: -10_signal
```

```
<222> LOCATION: (24)..(29)
<220> FEATURE:
<221> NAME/KEY: variation
<222> LOCATION: (7)..(23)
<223> OTHER INFORMATION: Region can be variable.

<400> SEQUENCE: 231
ttgcgtnnnn nnnnnnnnnn nnntataat                              29

<210> SEQ ID NO 232
<211> LENGTH: 29
<212> TYPE: DNA
<213> ORGANISM: Bacillus subtilis
<220> FEATURE:
<221> NAME/KEY: -35_signal
<222> LOCATION: (1)..(6)
<220> FEATURE:
<221> NAME/KEY: -10_signal
<222> LOCATION: (24)..(29)
<220> FEATURE:
<221> NAME/KEY: variation
<222> LOCATION: (7)..(23)
<223> OTHER INFORMATION: Region can be variable.

<400> SEQUENCE: 232
ttgaagnnnn nnnnnnnnnn nnntactat                              29

<210> SEQ ID NO 233
<211> LENGTH: 30
<212> TYPE: DNA
<213> ORGANISM: Bacillus subtilis
<220> FEATURE:
<221> NAME/KEY: -35_signal
<222> LOCATION: (1)..(6)
<220> FEATURE:
<221> NAME/KEY: -10_signal
<222> LOCATION: (25)..(30)
<220> FEATURE:
<221> NAME/KEY: variation
<222> LOCATION: (7)..(24)
<223> OTHER INFORMATION: Region can be variable.

<400> SEQUENCE: 233
ttgaatnnnn nnnnnnnnnn nnnntaaaaa                             30

<210> SEQ ID NO 234
<211> LENGTH: 43
<212> TYPE: DNA
<213> ORGANISM: Artificial Sequence
<220> FEATURE:
<223> OTHER INFORMATION: Description of Artificial Sequence: Ribosome
      binding site and the polylinker stretch including
      the translational start site within the NdeI site

<400> SEQUENCE: 234
ctcgagaatt aaaggagggt ttcatatgaa ttcggatccc ggg              43

<210> SEQ ID NO 235
<211> LENGTH: 10
<212> TYPE: DNA
<213> ORGANISM: Ac# J01522

<400> SEQUENCE: 235
aaatgtagtg                                                   10

<210> SEQ ID NO 236
<211> LENGTH: 10
<212> TYPE: DNA
<213> ORGANISM: Artificial Sequence
```

```
<220> FEATURE:
<223> OTHER INFORMATION: Description of Artificial Sequence:RBS and
      polylinker

<400> SEQUENCE: 236
gaattcggat                                                                10

<210> SEQ ID NO 237
<211> LENGTH: 10
<212> TYPE: DNA
<213> ORGANISM: Ac# M13201

<400> SEQUENCE: 237
gtaatacata                                                                10

<210> SEQ ID NO 238
<211> LENGTH: 10
<212> TYPE: DNA
<213> ORGANISM: Ac# Y00116

<400> SEQUENCE: 238
gcttccaagg                                                                10

<210> SEQ ID NO 239
<211> LENGTH: 10
<212> TYPE: DNA
<213> ORGANISM: Ac# X02730

<400> SEQUENCE: 239
ttttgtaatg                                                                10

<210> SEQ ID NO 240
<211> LENGTH: 10
<212> TYPE: DNA
<213> ORGANISM: Ac# J01749

<400> SEQUENCE: 240
cccagcgcgt                                                                10

<210> SEQ ID NO 241
<211> LENGTH: 10
<212> TYPE: DNA
<213> ORGANISM: Ac# X02730

<400> SEQUENCE: 241
actttcttga                                                                10

<210> SEQ ID NO 242
<211> LENGTH: 12
<212> TYPE: DNA
<213> ORGANISM: Artificial Sequence
<220> FEATURE:
<223> OTHER INFORMATION: Description of Artificial Sequence:Synthetic
      Linker

<400> SEQUENCE: 242
gctagcgacg tc                                                             12

<210> SEQ ID NO 243
<211> LENGTH: 11
<212> TYPE: DNA
<213> ORGANISM: Artificial Sequence
<220> FEATURE:
<223> OTHER INFORMATION: Description of Artificial Sequence:Synthetic
      Linker
```

```
<400> SEQUENCE: 243
cggccgctag c                                                    11

<210> SEQ ID NO 244
<211> LENGTH: 10
<212> TYPE: DNA
<213> ORGANISM: Artificial Sequence
<220> FEATURE:
<223> OTHER INFORMATION: Description of Artificial Sequence:Synthetic
      polylinker

<400> SEQUENCE: 244
aattaaagga                                                      10

<210> SEQ ID NO 245
<211> LENGTH: 10
<212> TYPE: DNA
<213> ORGANISM: Ac# M13201

<400> SEQUENCE: 245
tccaagagca                                                      10

<210> SEQ ID NO 246
<211> LENGTH: 10
<212> TYPE: DNA
<213> ORGANISM: Ac# Y00116

<400> SEQUENCE: 246
agcaaagaat                                                      10

<210> SEQ ID NO 247
<211> LENGTH: 10
<212> TYPE: DNA
<213> ORGANISM: Ac# X02730

<400> SEQUENCE: 247
tcagttccag                                                      10

<210> SEQ ID NO 248
<211> LENGTH: 10
<212> TYPE: DNA
<213> ORGANISM: Ac# J01749

<400> SEQUENCE: 248
aggtggcact                                                      10

<210> SEQ ID NO 249
<211> LENGTH: 10
<212> TYPE: DNA
<213> ORGANISM: Ac# 1360836

<400> SEQUENCE: 249
gcaaacgttg                                                      10

<210> SEQ ID NO 250
<211> LENGTH: 10
<212> TYPE: DNA
<213> ORGANISM: Ac# J01552

<400> SEQUENCE: 250
gtcttattaa                                                      10
```

-continued

```
<210> SEQ ID NO 251
<211> LENGTH: 20
<212> TYPE: DNA
<213> ORGANISM: Bacillus subtilis

<400> SEQUENCE: 251
gaagattcat atgtttcatc                                              20

<210> SEQ ID NO 252
<211> LENGTH: 20
<212> TYPE: DNA
<213> ORGANISM: Bacillus subtilis

<400> SEQUENCE: 252
tatggatcct tagaaatgaa                                              20
```

What is claimed is:

1. A recombinant gram positive bacterium selected from the group consisting of Corynebacter, Streptococcus, Staphylococcus, Lactococcus, and Bacillus which has been transformed by one or more copies of three exogenous DNA sequences, the first and second of said exogenous DNA sequences each comprising a DNA sequence coding for the riboflavin synthesizing enzymatic activities of *Bacillus subtilis* or a DNA sequence which encodes a polypeptide having riboflavin synthesizing enzymatic activity from *Bacillus subtilis* and one or more transcription elements and a third exogenous DNA sequence coding for the ribA gene product of *Bacillus subtilis* or a DNA sequence which encodes a polypeptide having GTP cyclohydrolase II or 3,4-dihydroxy-2-butanone 4-phosphate synthetase activity from *Bacillus subtilis* and one or more transcription elements wherein one or a plurality of copies of each of the first, second and third exogenous DNA sequences have been integrated at three different sites within its chromosome.

2. The recombinant bacterium according to claim 1 wherein the first and second exogenous DNA sequences further comprise two transcription elements each.

3. The recombinant bacterium according to claim 1 whereby the first and second exogenous DNA sequences which comprise the DNA sequence coding for the riboflavin synthesizing enzymatic activities of *Bacillus subtilis* have been integrated at two different sites of the chromosome each in a plurality of copies and the third exogenous DNA sequence has been integrated at a third site as a single copy.

4. The recombinant bacterium according to claim 1 wherein said bacterium is *Bacillus subtilis*.

5. A process for the production of riboflavin comprising growing the recombinant bacterium according to claim 1 under suitable growth conditions and isolating the riboflavin secreted into the medium.

6. The recombinant bacterium according to claim 2, wherein said transcription elements of the first, second and third exogenous DNA sequences are promoters.

7. The recombinant bacterium according to claim 2 whereby the first and second exogenous DNA sequences which comprise the DNA sequence coding for the riboflavin synthesizing enzymatic activities of *Bacillus subtilis* have been integrated at two different sites of the chromosome each in a plurality of copies and the third exogenous DNA sequence has been integrated at a third site as a single copy.

8. The recombinant bacterium according to claim 6 whereby the first and second exogenous DNA sequences which comprise the DNA sequence coding for the riboflavin synthesizing enzymatic activities of *Bacillus subtilis* have been integrated at two different sites of the chromosomes each in a plurality of copies and the third exogenous DNA sequence has been integrated at a third site as a single copy.

9. The recombinant bacterium according to claim 2 wherein said bacterium is *Bacillus subtilis*.

10. A process for the production of riboflavin comprising growing the recombinant bacterium according to claim 2 under suitable growth conditions and isolating the riboflavin secreted into the medium.

11. The recombinant bacterium according to claim 6 wherein said bacterium is *Bacillus subtilis*.

12. A process for the production of riboflavin comprising growing the recombinant bacterium according to claim 6 under suitable growth conditions and isolating the riboflavin secreted into the medium.

13. The recombinant bacterium according to claim 3 wherein said bacterium is *Bacillus subtilis*.

14. A process for the production of riboflavin comprising growing the recombinant bacterium according to claim 3 under suitable growth conditions and isolating the riboflavin secreted into the medium.

15. The recombinant bacterium according to claim 7 wherein said bacterium is *Bacillus subtilis*.

16. The recombinant bacterium according to claim 8 wherein said bacterium is *Bacillus subtilis*.

17. A process for the production of riboflavin comprising growing the recombinant bacterium according to claim 5 under suitable growth conditions and isolating the riboflavin secreted into the medium.

18. A process for the production of riboflavin comprising growing the recombinant bacterium according to claim 4 under suitable growth conditions and isolating the riboflavin secreted into the medium.

19. A recombinant *E. coli* bacterium which has been transformed by one or more copies of three exogenous DNA sequences, the first and second of said exogenous sequences each comprising a DNA sequence coding for the riboflavin synthesizing enzymatic activities of *Bacillus subtilis* or a DNA sequence which encodes a polypeptide having riboflavin synthesizing enzymatic activity from *Bacillus subtilis* and one or more transcription elements and a third exogenous DNA sequence coding for the ribA gene product of *Bacillus subtilis* or a DNA sequence which encodes a polypeptide having GTP cyclohydrolase II or 3,4-dihydroxy-2-butanone 4-phosphate synthetase activity from *Bacillus subtilis* and one or more transcription elements wherein one or a plurality of copies of each of the first, second and third exogenous DNA sequences have been integrated at three different sites within its chromosome.

20. The recombinant *E. coli* bacterium according to claim 19 wherein the first and second exogenous DNA sequences further comprise two transcription elements each.

21. A recombinant *E. coli* bacterium according to claim 19 whereby the first and second exogenous DNA sequences which comprise the DNA sequence coding for the riboflavin synthesizing enzymatic activities of *Bacillus subtilis* have been integrated at two different sites of the chromosome each in a plurality of copies and the third exogenous DNA sequence has been integrated at a third site as a single copy.

22. The recombinant *E. coli* bacterium according to claim 20, wherein said transciption elements of the first, second and third exogenous DNA sequences are promoters.

23. A recombinant *E. coli* bacterium according to claim 20 whereby the first and second exogenous DNA sequences which comprise the DNA sequence coding for the riboflavin synthesizing enzymatic activities of *Bacillus subtilis* have been integrated at two different sites of the chromosome each in a plurality of copies and the third exogenous DNA sequence has been integrated at a third site as a single copy.

24. A recombinant *E. coli* bacterium according to claim 22 whereby the first and second exogenous DNA sequences which comprise the DNA sequence coding for the riboflavin synthesizing enzymatic activities of *Bacillus subtilis* have been integrated at two different sites of the chromosome each in a plurality of copies and the third exogenous DNA sequence has been integrated at a third site as a single copy.

* * * * *